US 8,105,290 B2

(12) United States Patent
Wright et al.

(10) Patent No.: US 8,105,290 B2
(45) Date of Patent: Jan. 31, 2012

(54) UNIVERSAL CATHETER SECUREMENT DEVICE

(75) Inventors: Clifford A. Wright, San Diego, CA (US); Thomas Jackson, La Jolla, CA (US); Robert F. Eisele, Carlsbad, CA (US); Tom Lorenzana, Spring Valley, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

(21) Appl. No.: 12/601,360

(22) PCT Filed: May 30, 2008

(86) PCT No.: PCT/US2008/065364
§ 371 (c)(1),
(2), (4) Date: Nov. 23, 2009

(87) PCT Pub. No.: WO2008/151047
PCT Pub. Date: Dec. 11, 2008

(65) Prior Publication Data
US 2010/0179482 A1    Jul. 15, 2010

Related U.S. Application Data

(60) Provisional application No. 60/941,647, filed on Jun. 1, 2007.

(51) Int. Cl.
*A61M 5/32* (2006.01)
(52) U.S. Cl. ......... 604/174; 604/175; 604/177; 604/178
(58) Field of Classification Search ............... 604/96.01, 604/164.01, 174, 175, 177, 178, 179; 606/1, 606/108, 144
See application file for complete search history.

(56) References Cited

U.S. PATENT DOCUMENTS

| 2,525,398 A | 10/1950 | Collins |
| 2,533,961 A | 12/1950 | Rousseau et al. |
| 2,707,953 A | 5/1955 | Ryan |
| 3,059,645 A | 10/1962 | Hasbrouck et al. |
| 3,064,648 A | 11/1962 | Bujan |
| 3,482,569 A | 12/1969 | Raffaelli |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |

(Continued)

FOREIGN PATENT DOCUMENTS
EP          0064284 A2    11/1982
(Continued)

*Primary Examiner* — Kevin C Sirmons
*Assistant Examiner* — Bradley Thomas, Jr.
(74) *Attorney, Agent, or Firm* — Knobbe Martens Olson & Bear, LLP

(57) ABSTRACT

A universal device for securing a catheter on a patient includes a base which optionally has one or more locating elements for positioning or securing a catheter or catheter fitting of various shapes or sizes. The base optionally includes a recessed or flat receiving area defined by locating elements arranged in any configuration suitable to hold or receive a catheter or catheter fitting, e.g., in a tapering or V shaped formation. Additional locating elements may be positioned elsewhere on the base for receiving or holding a flange or wing of a catheter fitting and preventing its movement in various directions. The base optionally has an angled surface to maintain the desired angle for catheters or catheter fittings in a patient. A cover is removably or permanently connected to the base and may optionally have one or more top openings for receiving tabs or extensions of a catheter fitting.

19 Claims, 58 Drawing Sheets

U.S. PATENT DOCUMENTS

| | | |
|---|---|---|
| 3,766,915 A | 10/1973 | Rychlik |
| 3,834,380 A | 9/1974 | Boyd |
| 3,856,020 A | 12/1974 | Kovac |
| 3,896,527 A * | 7/1975 | Miller et al. .............. 24/499 |
| 3,906,946 A | 9/1975 | Nordström |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,129,128 A | 12/1978 | McFarlane |
| 4,142,527 A | 3/1979 | Garcia |
| 4,161,177 A | 7/1979 | Fuchs |
| 4,165,748 A | 8/1979 | Johnson |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,275,721 A | 6/1981 | Olson |
| 4,284,076 A | 8/1981 | Hall |
| 4,316,461 A | 2/1982 | Marais et al. |
| 4,326,519 A | 4/1982 | D'Alo et al. |
| 4,333,468 A | 6/1982 | Geist |
| 4,362,156 A | 12/1982 | Feller et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,480,639 A | 11/1984 | Peterson et al. |
| 4,627,842 A | 12/1986 | Katz |
| 4,683,882 A | 8/1987 | Laird |
| 4,711,636 A | 12/1987 | Bierman |
| 4,737,143 A | 4/1988 | Russell |
| 4,742,824 A | 5/1988 | Payton et al. |
| 4,792,163 A | 12/1988 | Kulle |
| 4,808,162 A | 2/1989 | Oliver |
| 4,822,342 A | 4/1989 | Brawner |
| 4,832,019 A | 5/1989 | Weinstein et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,700 A | 12/1990 | Tollini |
| 4,986,815 A | 1/1991 | Schneider |
| 5,037,397 A | 8/1991 | Kalt et al. |
| 5,069,206 A | 12/1991 | Crosbie |
| 5,073,170 A | 12/1991 | Schneider |
| 5,084,026 A | 1/1992 | Shapiro |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,236,421 A | 8/1993 | Becher |
| 5,266,401 A | 11/1993 | Tollini |
| 5,267,967 A | 12/1993 | Schneider |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman et al. |
| 5,322,097 A | 6/1994 | Wright |
| 5,338,308 A | 8/1994 | Wilk |
| 5,342,317 A | 8/1994 | Claywell |
| 5,344,406 A | 9/1994 | Spooner |
| 5,352,211 A | 10/1994 | Merskelly |
| 5,354,282 A | 10/1994 | Bierman |
| 5,372,589 A | 12/1994 | Davis |
| 5,380,293 A | 1/1995 | Grant |
| 5,380,395 A | 1/1995 | Uchida |
| 5,382,239 A | 1/1995 | Orr et al. |
| 5,402,776 A | 4/1995 | Islava |
| 5,403,285 A | 4/1995 | Roberts |
| 5,413,562 A | 5/1995 | Swauger |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| 5,549,567 A | 8/1996 | Wolman |
| D375,355 S | 11/1996 | Bierman |
| 5,578,013 A | 11/1996 | Bierman |
| 5,593,395 A | 1/1997 | Martz |
| 5,637,098 A | 6/1997 | Bierman |
| 5,685,859 A | 11/1997 | Kornerup |
| 5,693,032 A | 12/1997 | Bierman |
| 5,722,959 A | 3/1998 | Bierman |
| 5,755,225 A | 5/1998 | Hutson |
| 5,810,781 A | 9/1998 | Bierman |
| 5,833,666 A | 11/1998 | Davis et al. |
| 5,911,707 A | 6/1999 | Wolvek et al. |
| 6,067,985 A | 5/2000 | Islava |
| 6,132,399 A | 10/2000 | Shultz |
| 6,213,979 B1 | 4/2001 | Bierman |
| 6,228,064 B1 | 5/2001 | Abita et al. |
| 6,283,945 B1 | 9/2001 | Bierman |
| 6,287,281 B1 | 9/2001 | Nishtala et al. |
| 6,428,515 B1 | 8/2002 | Bierman et al. |
| 6,482,183 B1 * | 11/2002 | Pausch et al. ................. 604/174 |
| 6,488,664 B1 | 12/2002 | Solomon et al. |
| 6,491,664 B2 | 12/2002 | Bierman |
| 6,582,403 B1 | 6/2003 | Bierman et al. |
| 7,413,561 B2 | 8/2008 | Raulerson et al. |
| 2005/0107738 A1 * | 5/2005 | Slater et al. ................. 604/96.01 |
| 2006/0089600 A1 * | 4/2006 | Bierman et al. .............. 604/175 |
| 2006/0161087 A1 * | 7/2006 | Carter et al. ..................... 602/32 |
| 2006/0247661 A1 * | 11/2006 | Richards et al. .............. 606/108 |
| 2006/0293643 A1 * | 12/2006 | Wallace et al. .................... 606/1 |
| 2007/0043385 A1 * | 2/2007 | Nobles et al. ................. 606/144 |
| 2007/0060890 A1 * | 3/2007 | Cuppy ..................... 604/164.01 |
| 2007/0173766 A1 | 7/2007 | Bierman |
| 2009/0254040 A1 | 10/2009 | Bierman et al. |

FOREIGN PATENT DOCUMENTS

| | | |
|---|---|---|
| EP | 356683 A1 | 3/1990 |
| FR | 2381529 | 2/1978 |
| GB | 2086466 | 5/1982 |
| GB | 2211417 | 7/1989 |
| WO | WO 80/01458 | 7/1980 |
| WO | WO 92/19309 | 11/1992 |
| WO | WO 94/12231 | 6/1994 |
| WO | WO 97/15342 | 5/1997 |

* cited by examiner

FIG. 18
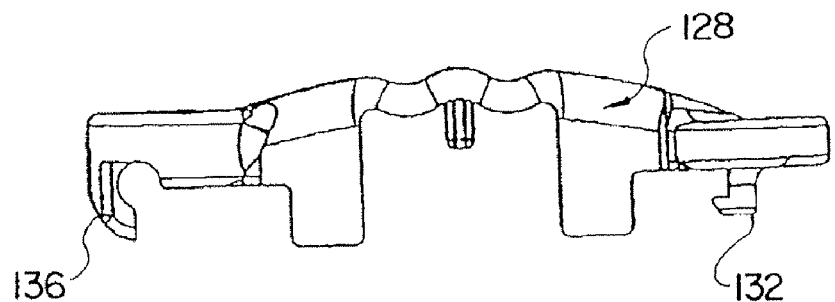
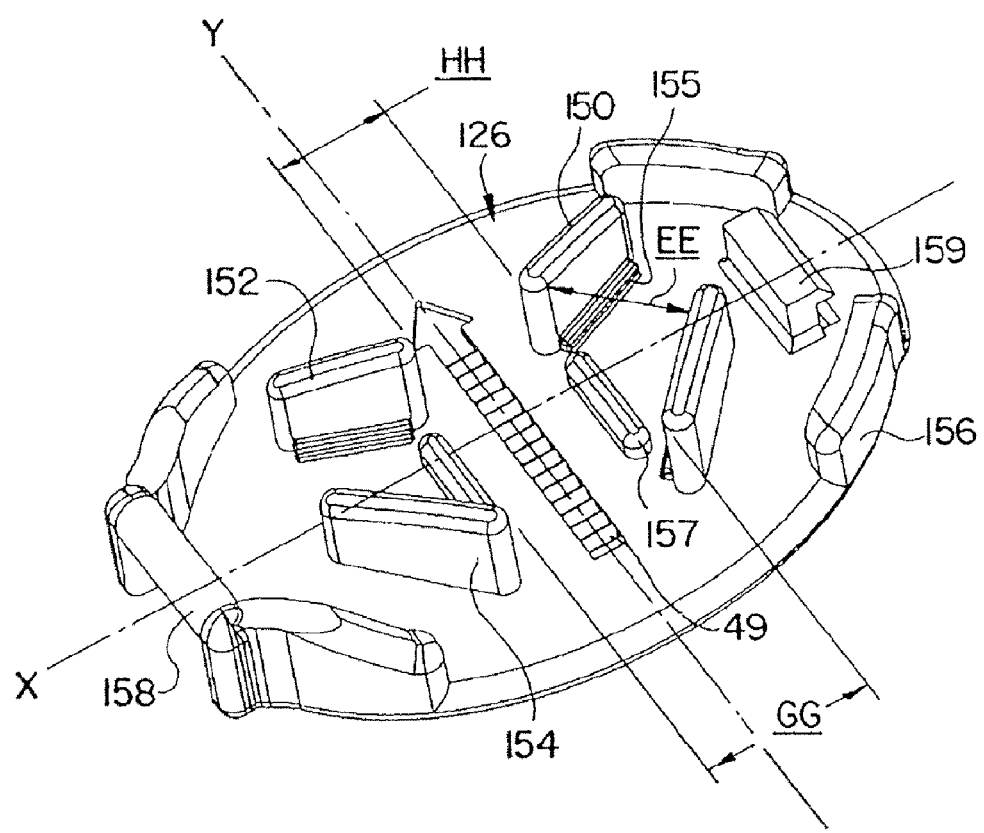
FIG. 19

UNIVERSAL CATHETER SECUREMENT DEVICE

PRIORITY CLAIM

This application is the National Stage of International Application No. PCT/US2008/065364, filed on May 30, 2008, entitled UNIVERSAL CATHETER SECUREMENT DEVICE, which claims the benefit of U.S. Provisional Patent Application No. 60/941,647, filed June 1, 2007, both of which are hereby expressly incorporated by reference in their entireties.

BACKGROUND

It is often necessary to introduce fluids and liquid medications directly into a blood vessel of a patient. Various types of catheters are often used in combination with connectors and syringes. A catheter is essentially a tube inserted through an incision in the skin into a blood vessel in the patient's body, generally without surgery. A simple intravenous (IV) line is usually acceptable for introduction of fluids and liquid medications into a blood vessel for short term general use. IV lines are typically inserted into a patient's arm by inserting a catheter that contains a needle which pierces the skin. The needle is then removed and discarded while the soft catheter stays in the blood vessel. The external portion of the catheter is usually taped in place or secured with a self-adhesive dressing to the patient's arm. This external portion often consists of flexible tubing and a locking hub. For longer term and more specialized needs, different types of catheters or other devices are used. Peripherally inserted central catheters (PICCs) are frequently used to provide medications or fluids to home care patients over longer periods of time. PICCs may also be used for frequent blood sampling.

IV lines commonly remain in patients for days at a time, while a PICC line and similar catheters may remain in place in a patient for several weeks or months. In both cases it is important that movement of the catheter be minimized. If the catheter is not secured in place, it may be inadvertently displaced from the intended location. Consequently, medication delivered through an IV or PICC line may then be released at an incorrect position within the blood vessel. Repeated back and forth catheter movement, or pistoning, can cause irritation of the blood vessel, disrupt proper introduction of medications to the patient, and increase the potential for bleeding or infection at the catheter incision site. If extensive movement occurs, the IV or PICC line could even come out of the patient, interrupting delivery of medication and requiring re-insertion, often with hospitalization.

In the past, catheters were simply taped into place on the patient's skin. However, taping is time consuming and labor intensive. Tape also collects bacteria and must be frequently removed and replaced. More importantly, taping is not necessarily effective in securing a catheter in place. Sutures have also been used to attach a catheter to a patient. With sutures, the catheter is stitched onto the skin. Sutures, however, can also be a source of infection, can cause pain and inflammation, and can make it more difficult to clean around the incision site. Sutures also require time and skill to place, and can cause scarring.

More recently, manufactured catheter anchors or securing devices have become widely used. These devices are designed to secure specific catheters in place. While various designs have been used, these devices generally have an adhesive-backed pad that bonds to the skin over a large area. The catheter is secured into or onto a catheter anchor designed for holding the catheter. However, engineering design challenges remain in providing reliable, secure and efficient anchoring devices. Further, because existing anchoring devices are generally designed for a specific type of catheter, multiple anchors may be needed to accommodate use of different types of catheters in hospitals, clinical settings, or other arenas. This adds to the cost and complexity of sourcing, inventory, storage, and selection of the anchoring devices. Accordingly, improved anchoring devices are needed.

SUMMARY

A universal device for securing a catheter on a patient includes a base which optionally has one or more locating elements for positioning or securing a catheter or catheter fitting of various shapes or sizes. The base optionally includes a recessed or flat receiving area defined by locating elements arranged in any configuration suitable to hold or receive a catheter or catheter fitting, e.g., in a tapering or V shaped formation. Additional locating elements may be positioned elsewhere on the base for receiving or holding a flange or wing or other part of a catheter fitting and preventing movement of the catheter fitting in various directions. The base optionally has an angled surface to maintain the desired angle of catheters or catheter fittings in a patient, e.g., in IV use. A cover is removably or permanently connected to the base and may optionally have one or more top openings for receiving tabs or extensions of a catheter fitting. The cover may optionally include one or more capture ridges for restraining a catheter or catheter fitting of various shapes or sizes on the base or on a retention plate. The cover may also include one or more tabs or contact bars for holding catheter fittings of various designs in place. One or more latching elements for securing the base to the cover in a closed position may optionally be included on either or both the cover and the base.

The base optionally has an opening and one or more restraining elements positioned on a surface of the base and extending over a portion of the opening. A retention plate having one or more locating elements for positioning or securing a catheter or catheter fitting of various shapes or sizes on the retention plate may be positioned in the opening of the base. Optionally, the retention plate may be movable in one or more directions. A support plate or similar device attached to the base holds the retention plate between the restraining elements and the support plate. The base or support plate may be attached to an adhesive pad for attachment to a patient.

Other features and advantages will appear hereinafter. The features described above and below can be used separately or together, or in various combinations of one or more of them.

BRIEF DESCRIPTION OF THE DRAWINGS

In the drawings, the same element number indicates the same element in each of the views.

FIG. 18 is a side view of the cover shown in FIG. 16.

FIG. 19 is a top perspective view of a base for attachment to the cover of FIGS. 16-18.

DETAILED DESCRIPTION OF THE DRAWINGS

Figure 1:
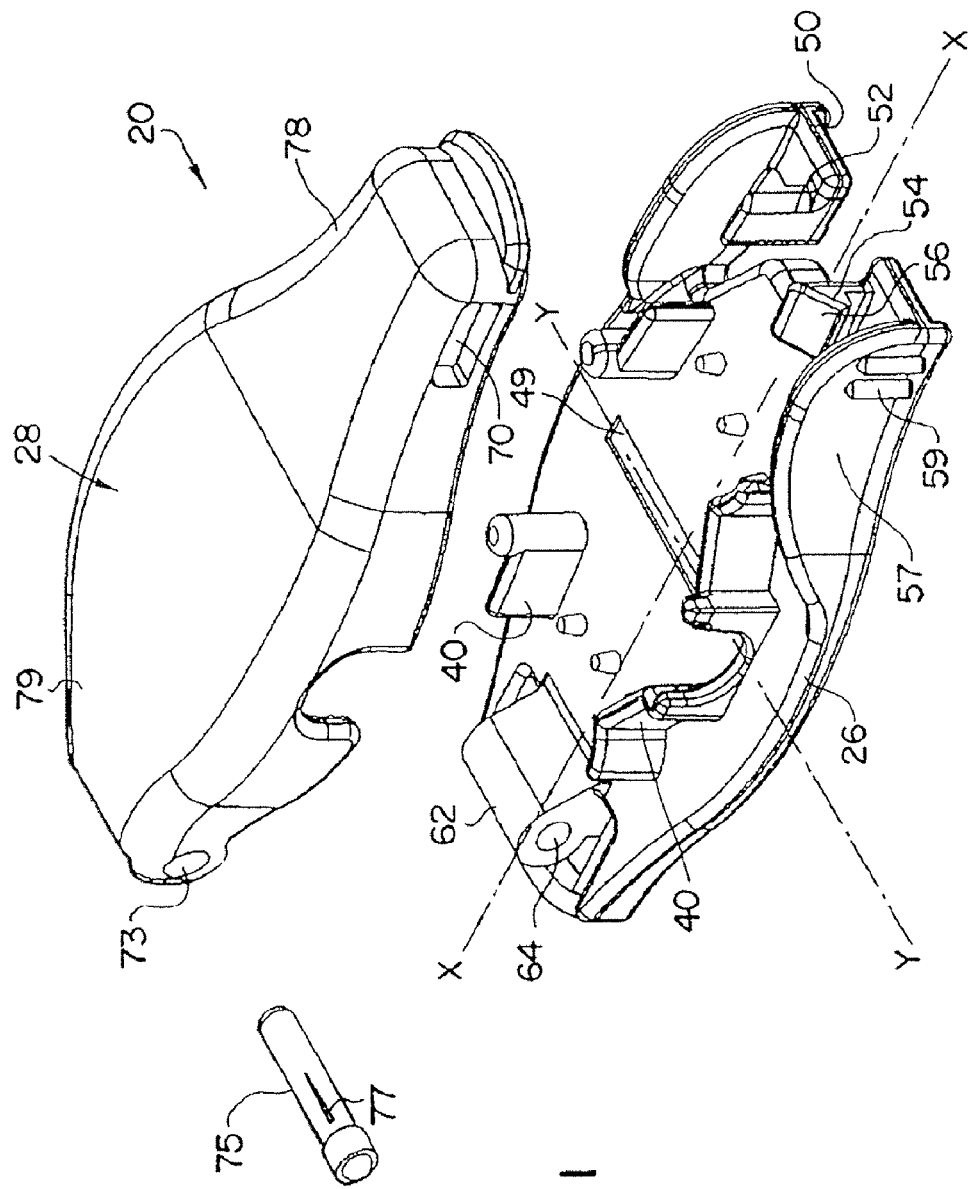
FIG. 1 is an exploded perspective view of a securing device.

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

A universal securing device for holding catheters or catheter fittings of various designs, shapes, or sizes may include a base and a cover. The cover may be connected to the base by a hinge which allows the cover to be lifted open or pushed down into a closed position, to secure a catheter fitting or similar device. The base and/or cover have locating elements configured and arranged to fit around catheters and catheter fittings of various shapes and sizes. The catheter fitting is placed into or onto the base from above. The locating elements prevent substantial movement of a catheter and/or catheter fitting in multiple dimensions.

A catheter fitting to be held by and of the devices described herein includes any type of catheter fitting, attachment, accessory, connector, etc., whether integral with the catheter or as a separate piece from the catheter. A catheter may also refer to a catheter alone or in combination with any type of catheter fitting.

Latching elements, which may be located on squeezing arms, hold the cover onto the base. Capture elements may be located on the under side of the cover to compress a catheter fitting, securely holding it in place against the base, in the closed position. The catheter may be held securely in place on a patient once the securing device is attached to the patient. The catheter can be removed from the base by disengaging the latching elements, for example, here by squeezing the squeezing arms toward each other. Thus, a catheter and catheter fitting of various shapes and sizes can be securely held by a single securing device and can be quickly and easily attached to or removed from the patient.

The devices described herein may be used with, e.g., PICC lines, IV catheters, Foley catheters, heart catheters, J-loops, epidural lines or catheters, arterial lines or catheters, and various others. In addition to a catheter, the securing devices herein may be used to secure other tubes, cables, wires, and various other medical devices as well.

Figure 2:
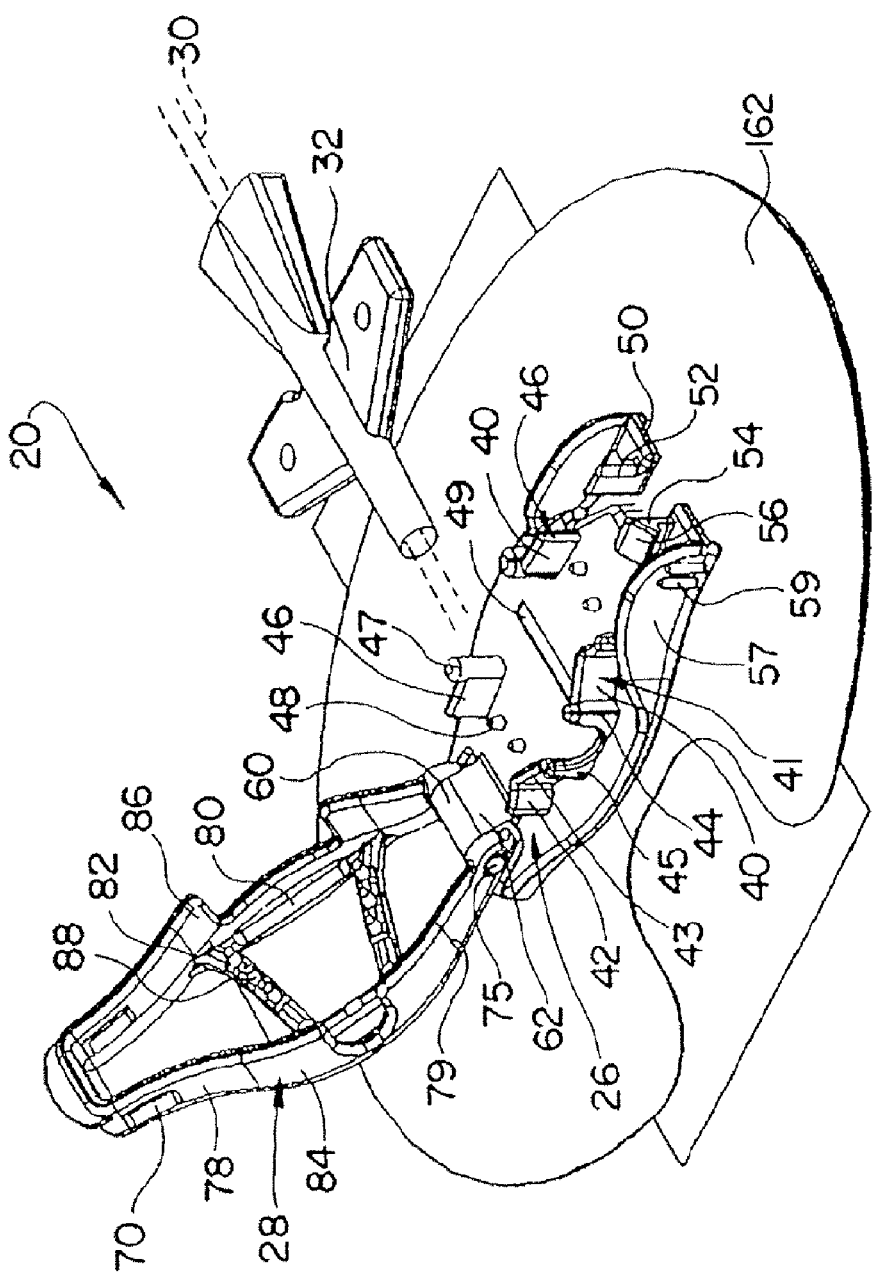
FIG. 2 is a top and front perspective view of the device shown in FIG. 1, with the cover lifted in an open position and base attached to an adhesive pad.

Turning now to the drawings, as shown in FIGS. 1-9, a securing device 20 has a base 26. As shown in FIG. 2, the base 26 may be contoured and may have one or more locating elements 40 which are shaped and dimensioned to be positioned around and hold catheters and catheter fittings of various shapes and sizes, such as catheter fitting 32 and catheter 30. In FIGS. 2-5 and 8-9, the locating elements 40 include rectangular shaped walls, however, locating elements may be round, square, hexagonal, etc. and they may take on various forms in addition to walls such as pegs, columns, etc. The base may vary in size and typically is about 2-3 inches long and about 1-2 inches wide.

Figure 3:
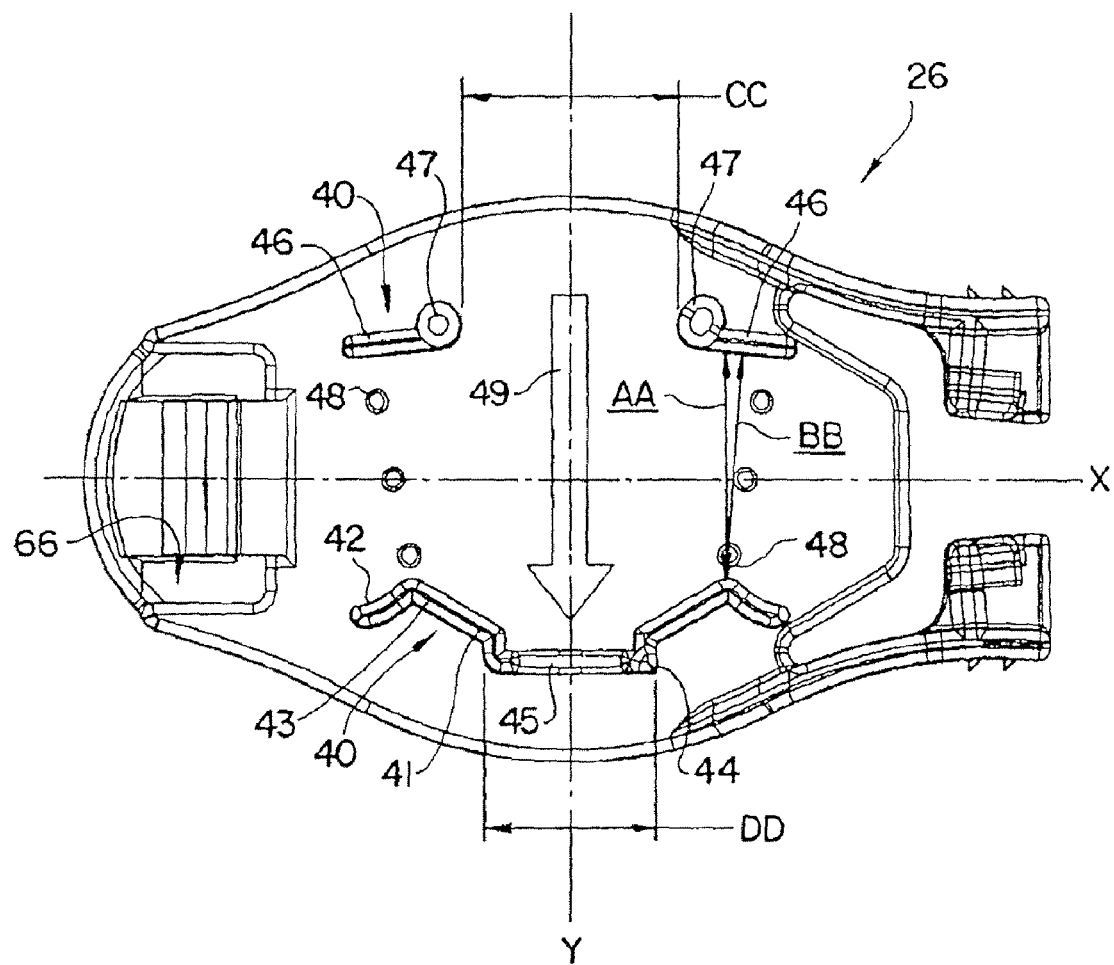
FIG. 3 is a plan view of the top surface of the base and locating elements of a securing device shown in FIGS. 1-2.
Figure 4:
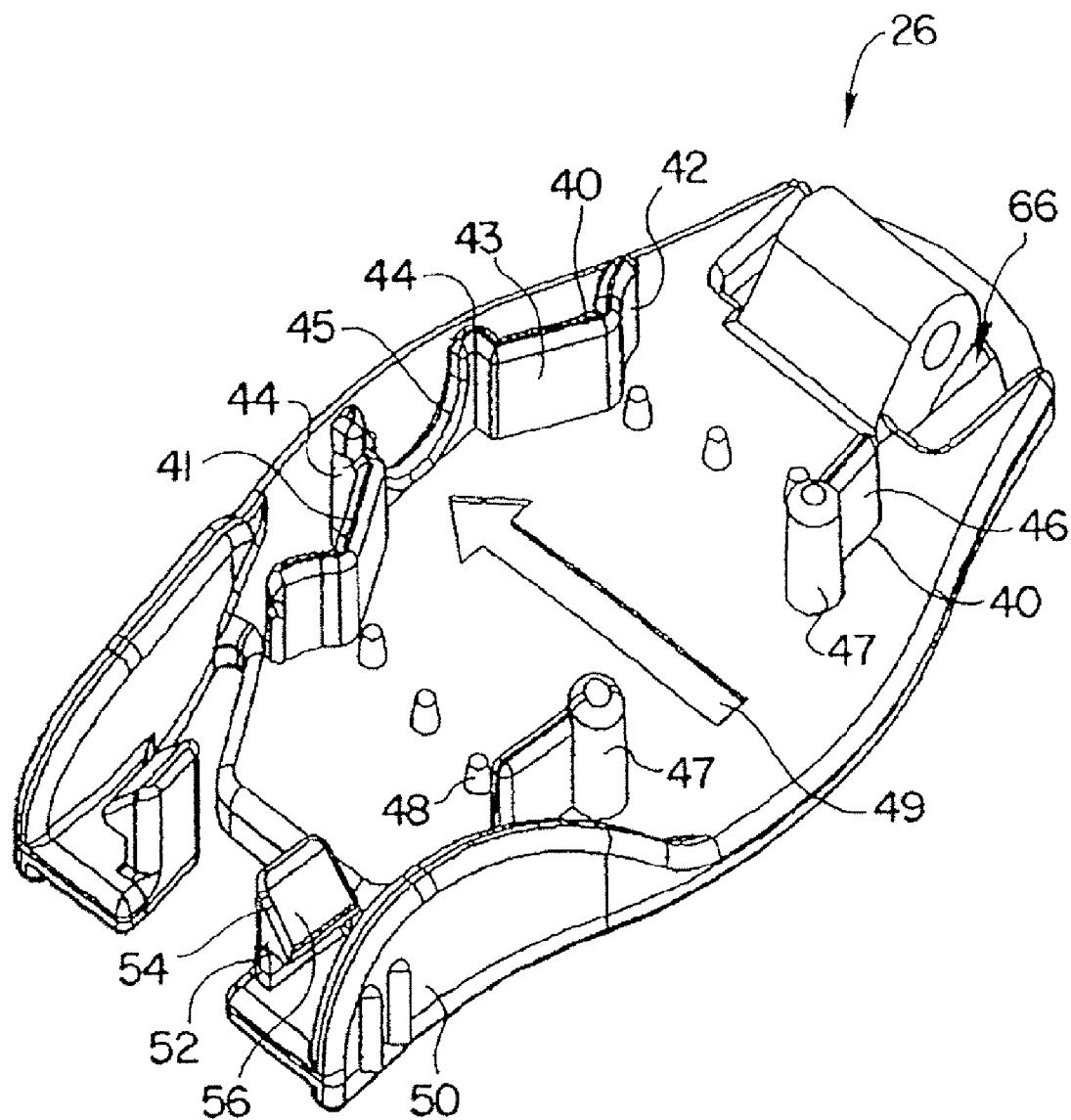
FIG. 4 is top and front perspective view of the base shown in FIGS. 1-3.
Figure 5:
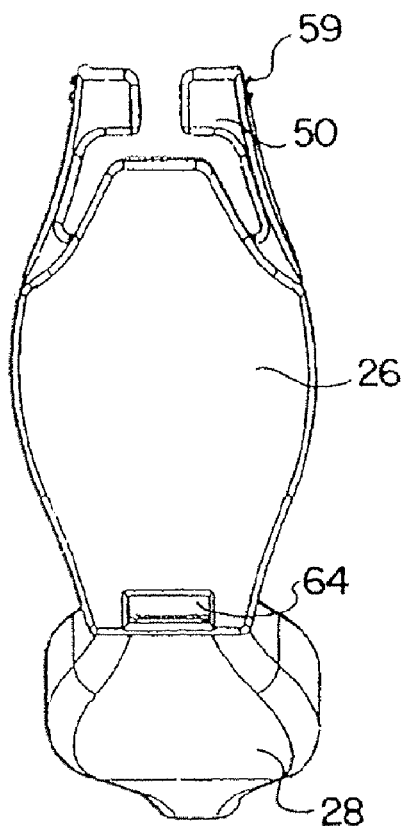
FIG. 5 is a back perspective view showing the bottom surface of the base shown in FIG. 4.

Referring to FIGS. 3-4, the locating elements 40 extend up from the base 26. In this particular embodiment, the locating elements include at least one front wall 41 and a pair of back walls 46. The front and back walls are spaced apart in a front to back direction as indicated by arrow 49, which runs along a longitudinal axis identified by the imaginary line marked Y shown in FIG. 3. A front wall 41 shown in FIGS. 3-4 is made up of at least one curved end wall 42, at least one angled front wall 43, at least one elbow 44. A semicircular trough 45 may be positioned slightly forward of the angled front wall 43 as indicated by arrow 49 and may be connected to the elbow 44. A raised post may extend up from at least one elbow 44. The back walls 46 are preferably angled and are each connected to a post 47. The first and second posts 47 connected to either back wall 46, can be the same size or they may differ in size. In general, the locating elements 40 may be substantially symmetrical side-to-side about the longitudinal axis or centerline Y. The locating elements 40 are arranged and positioned to allow PICCs and other catheters of various shapes and sizes to be placed onto the base 26 and held within the securing device 20. The locating elements 40 are arranged in a manner to help position catheters and catheter fittings of various shapes and sizes and prevent substantial movement of a catheter and catheter fitting in various dimensions relative to the base, e.g., side-to-side and back-to-front, axial movement, as well as rotational movement.

Referring to FIGS. 3-4, in one embodiment the locating elements 40 are arranged such that a front wall 41 is separated from the back wall 46 by a dimension AA which extends straight back, parallel to the longitudinal Y axis, from the rear most tip of curved end wall 42 of front wall 41 to the back wall 46. The front wall 41 may also be separated from the back wall 46 by a dimension BB which extends from the rear most tip of curved end wall 42 of front wall 41, straight back and perpendicular to the back wall 46. Also, the inner edge of the first or left post 47 may be separated from the inner edge of the second or right post 47 by a dimension CC running generally parallel to a lateral axis X. Also, the first or left elbow 44 may be separated from the second or right elbow 44 by a dimension DD running parallel to dimension CC.

In one embodiment, dimension AA may be less than dimension BB. Also, dimension CC may be greater than dimension DD. In another embodiment dimension AA may measure about 0.34 to 0.38 inches, preferably 0.35 to 0.37 inches, or more preferably 0.36 inches in length. Dimension BB may measure about 0.37 to 0.41 inches, preferably 0.38 to 0.40 inches, or more preferably 0.39 inches in length. Also, dimension CC may measure about 0.35 to 0.39 inches, preferably 0.36 to 0.38 inches, or more preferably 0.37 inches in length and dimension DD may be about 0.28 to 0.32 inches, preferably 0.29 to 0.31 inches, or more preferably 0.30 inches in length. In another embodiment, dimension CC may be about 130 to 170% of dimension DD or more preferably about 140 to 160% of dimension DD.

Referring to FIGS. 3-4, the base may also include one or more spikes 48 extending up from the base. In one embodiment, a line of posts or spikes 48, are located on a line between front wall 41 and back wall 46, on both sides of axis Y. The line of posts or spikes 48 may be generally parallel to each other and to the longitudinal axis Y or at an angle of, e.g., 1-45° to the longitudinal axis Y. The spikes 48 may extend up from the surface of the base or from capture elements running generally parallel to each other and to the longitudinal axis Y or at an angle of, e.g., 1-45° to the longitudinal axis Y, on both sides of axis Y between a front wall 41 and a back wall 46.

Referring to FIG. 1, the base 26 may have two squeezing arms 50 or optionally the base 26 may have one arm 50 that is resilient and flexible and a second arm 50 which is generally fixed and rigid. The base 26 may also have a hinge block 62 located on the base 26 at an opposite end from the squeezing arms 50. The squeezing arms 50 are flexible and have latching elements 52 and sidewalls 57. An angled surface 56 may be provided at the end 54 of each of the latching elements 52 facing the inner surface of a squeezing arm wall 57, with grip ribs 59 on the outside of each squeezing arm wall 57. As shown in FIG. 3-4, a through hole 66 may be provided, if desired, in the base 26, behind the hinge block 62. An arrow symbol 49 may be printed, molded or otherwise provided on the base 26 and/or the cover 28, running along a longitudinal Y axis, as shown in FIG. 3. The arrow indicates in which direction the catheter should be installed into the universal securing device 20.

As shown in FIG. 1, the cover 28 has latch holes 70, and hinge pinholes 73 located at opposite ends of the cover 28. Ridges 71, each having an angled surface 72, may optionally be provided below the latch holes 70, as shown, e.g., in the embodiment of FIG. 10. As shown in FIG. 2, the cover 28 is connected to the base 26 by a hinge 60. FIG. 1 shows that the hinge may be provided by pressing a hinge pin 75 through hinge pinholes 73 and through an aligned hinge pin slot 64 which runs through the hinge block 62. The hinge pin 75 may have a round diameter and may include one or more, preferably four, raised crush ribs 77 which serve to hold the hinge pin 75 in place by friction after being press fit through the hinge pinholes 73 and hinge pin slot 64. The hinge may also take various other forms, for example, a hinge may be formed by tongue and groove elements. A hinge may also be formed by a snap fitting mechanism between a latch or snap hinge and snap hinge base. Various types of hinges or pivot joints may be used. Most designs will have a hinge at one side of the device and a latching element at the other side, with the cover pivoting open and closed. However, an alternative design may have a separate snap on cover having a latch or lock element at either end of the cover.

Figure 6:
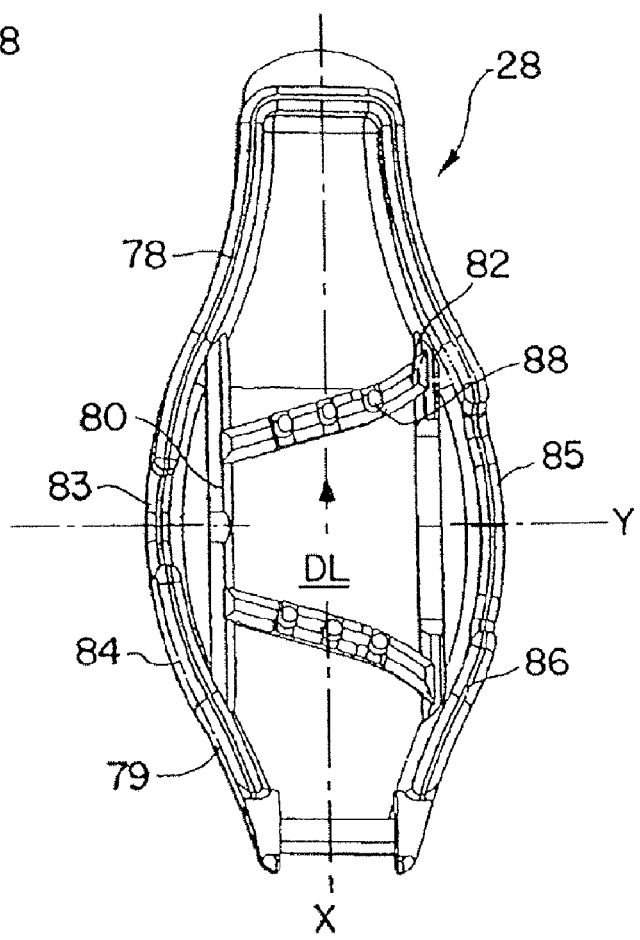
FIG. 6 is a plan view of the under side of the cover shown in FIGS. 1-2 and 5.
Figure 7:
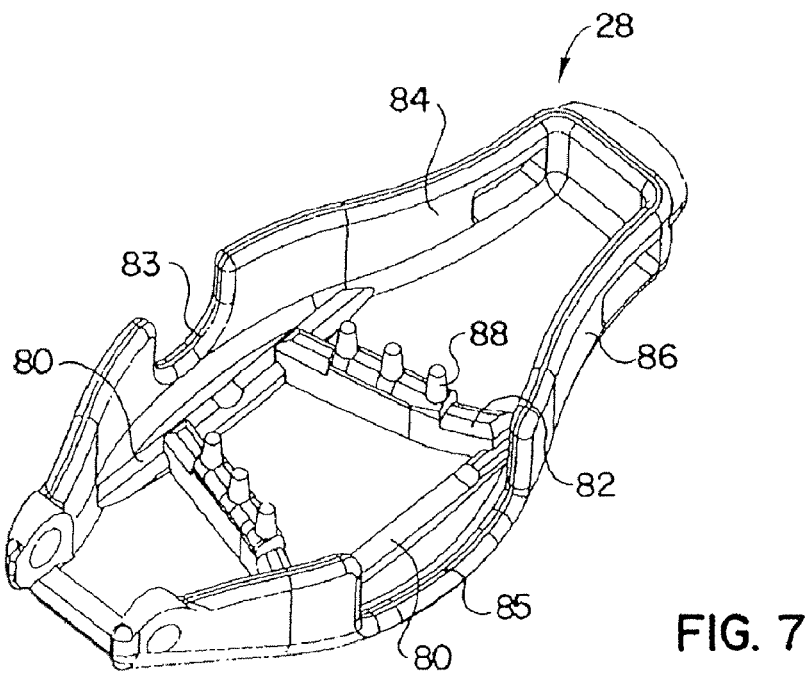
FIG. 7 is a top and back perspective view of the under side of the cover shown in FIGS. 1-2 and 5.
Figure 8:
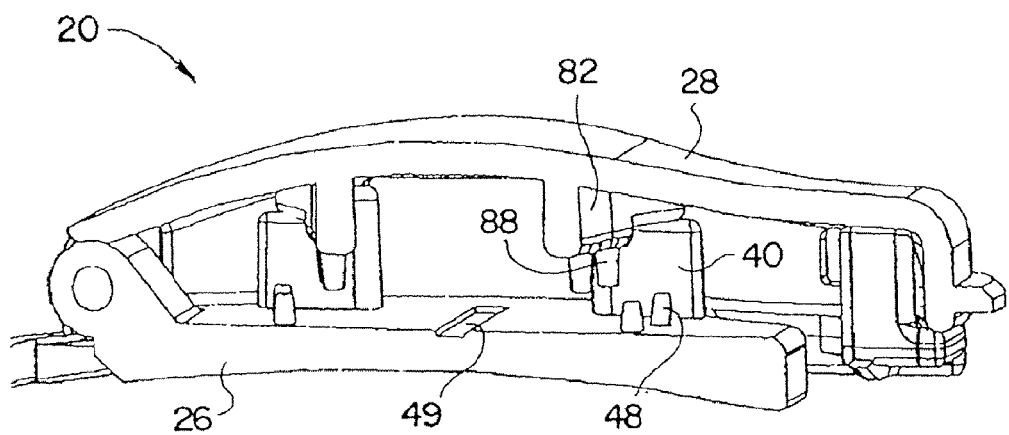
FIG. 8 is a cross section of a side perspective view of the securing device shown in FIGS. 1-2 and 5 in a closed position.

As best shown in FIGS. 6-7, the cover 28 includes a first opening 83 in a front wall 84 and a second opening 85 in a back wall 86. The cover 28 may have one or more bars 80 which run in a direction DL on the underside of the cover 28, generally parallel to the lateral X axis. The center area of the bars 80 may be recessed compared to the ends of the bars 80 in order to accommodate the height of various catheter fittings. The bars 80 may be connected by one or more capture elements 82 on the underside of the cover 28. The capture elements 82 may be generally parallel to each other and to the longitudinal Y axis, or at an angle of, e.g., 1-45° to the longitudinal axis. The ends of the capture element 82 may rest at least partially on the surface of the bars 80. One or more posts or spikes 88 may extend from the capture elements 82. In the design shown in FIG. 7, three spikes 88 are spaced evenly apart and extend up from a center elevated segment 86 on the surface of the capture element 82. Optionally, the capture elements 82 may run along the underside of a cover where the cover has no bars.

Turning momentarily to FIG. 2, the capture element 82 is adapted to contact and compress catheter fittings of various shapes and sizes such as catheter fitting 32, e.g., by compressing the wings and/or body of a catheter fitting 32 once the catheter fitting 32 is placed onto the base 26 within the locating elements 40 and the cover 28 is attached to the base 26 in a closed position. Capture elements 82 may be solid or spring molded as leaf springs or foam springs. Capture elements 82 may also be an elastomer. The surface of a capture element 82 may optionally be provided with cones or serrated teeth to assist with compression and gripping of a catheter fitting 32. A single capture element 82 or multiple capture elements 82 may be used. In the specific design shown if FIG. 2, two capture elements are provided.

Referring again to FIGS. 2 and 4, in use, after the catheter has been inserted into the patient, the skin at the securement site is preferably cleaned. The catheter fitting 32 is then placed into or onto the base 26, within the locating elements 40. The cover 28, which is attached to the base 26 via the hinge 60, can be closed down, by pivoting about the ends of the hinge pin 75 positioned inside the hinge block 62, over and onto the catheter fitting 32. The curved end wall 42, elbow 44 and semicircular trough 45, all serve to center and align the cover 28 as the cover 28 is moved down and over the front wall, onto the base 26, and into the closed position. The outside surface of the curved end wall 42, elbow 44 and semicircular trough 45 may abut against the inner surface of the front wall 84 of the cover 28 as the cover 28 moves down and into the closed position. Also, a raised post which may be located atop one or more elbows 44 may also help align the cover 28 as it closes onto the base 26, and it too may optionally abut against the inner surface of the front wall 84 of the cover 28 as the cover 28 moves down and into the closed position. Also, one or both of the posts 47 connected to a back wall 46 may serve to center and align the cover 28 as the cover 28 is moved down and over a back wall 46 and the first and second posts 47. The first and second posts 47 and back walls 46 may abut against the inner surface of the cover 28 as the cover 28 moves down and into the closed position. These alignment features help to properly locate the cover on the base as the cover is closed.

Figure 9:
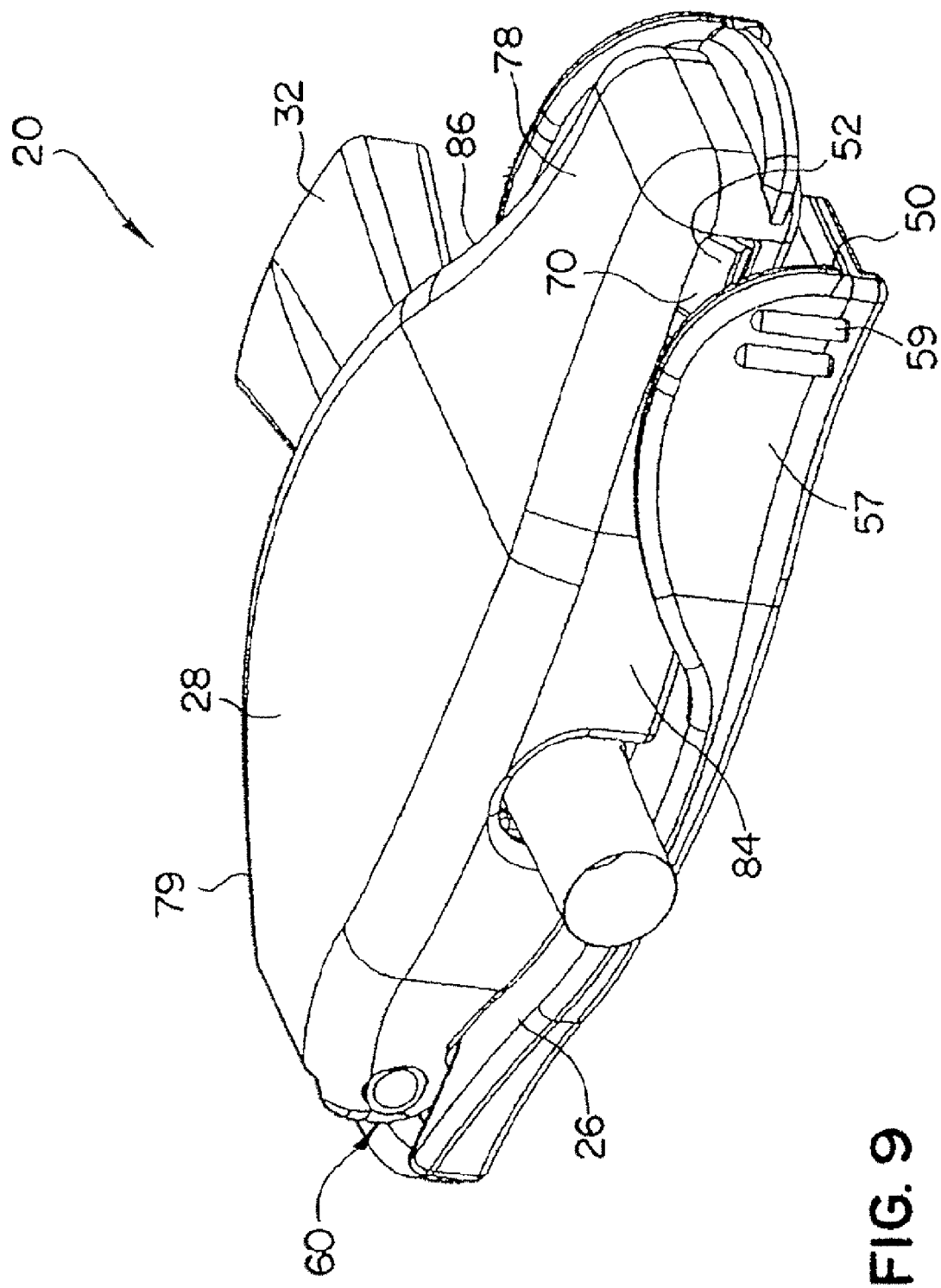
FIG. 9 is a top and front perspective view of the device shown in FIGS. 1-2 and 5 in a closed position.

In a closed position (as shown in FIG. 9), the top end 78 of the cover 28 attaches to the base 26 within the squeezing arm walls 57. The latch holes 70 in the front wall 84 and back wall 86 of the cover 28 engage the latching elements 52 on the squeezing arms 50. This facilitates the secure attachment of the cover 28 to the base 26, placing the securing device 20 in a closed position. The cover 28 rests on the flat and contoured outer areas of the base 26, around the front wall 41 and back walls 46 (not shown because enclosed by cover), and on the flat area of the squeezing arms 50.

In a closed position, the spikes 88 on one or more capture elements 82 may compress down on the wings and/or body of the catheter fitting 32. The wings of the catheter fitting 32, which are generally somewhat flexible or compliant, are thereby pinched or held between the spikes 88 of capture element 82 and the spikes 48 extending up from the surface of the base 26. The spikes 88 and the spikes 48 are located to grip and compress the wings and/or body of the catheter fitting. As shown if FIG. 8, the spikes 88 and spikes 48 are preferably about 0.04 inches in height and some vertical space may exist between the tips of the spikes 88 and the spikes 48 when the cover 28 is in the closed position. The spikes 88 may also be slightly offset by 0.02-0.12 inches to the inside of the spikes 48, i.e., toward the arrow 49. The spikes 88 may also be similarly offset to the front of the spikes 48, as indicated by arrow 49. This applies a pinching or bending effect on the wings of the catheter, in addition to compression. By having the top and bottom spikes offset from each other, the device 20 can better secure catheters having wings of varying thickness.

The capture elements 82 thereby secure a catheter fitting 32 within securing device 20 by preventing substantial movement of catheter fitting 32 in an axial, side-to-side, back-to-front, up and down and rotational direction. The capture element 82 may be resilient and flexible, capable of holding and griping catheter fittings of various thicknesses. The capture element 82 may also be solid. The cover 28 may be used in conjunction with a base 26, having locating elements 40 and spikes 48, for securing a catheter fitting.

In another embodiment, the cover 28 may be used in conjunction with a base 26 for compressing and holding a catheter body on a patient. The base may or may not have locating elements. In use, this embodiment would function by placing a catheter on a base 26 and compressing or pinching the catheter body between an underside surface of a cover 28, e.g., against capture elements 82 or any part of the underside of the cover, and a top surface of the base with sufficient force to hold or restrain the catheter in place without substantial movement in various dimensions relative to the base and cover, e.g., axial, side-to-side, back-to-front, up and down and rotational. This arrangement, for compressing a catheter body of various shapes and sizes between a cover and base could be performed with any of the additional embodiments described below as well.

Figure 10:
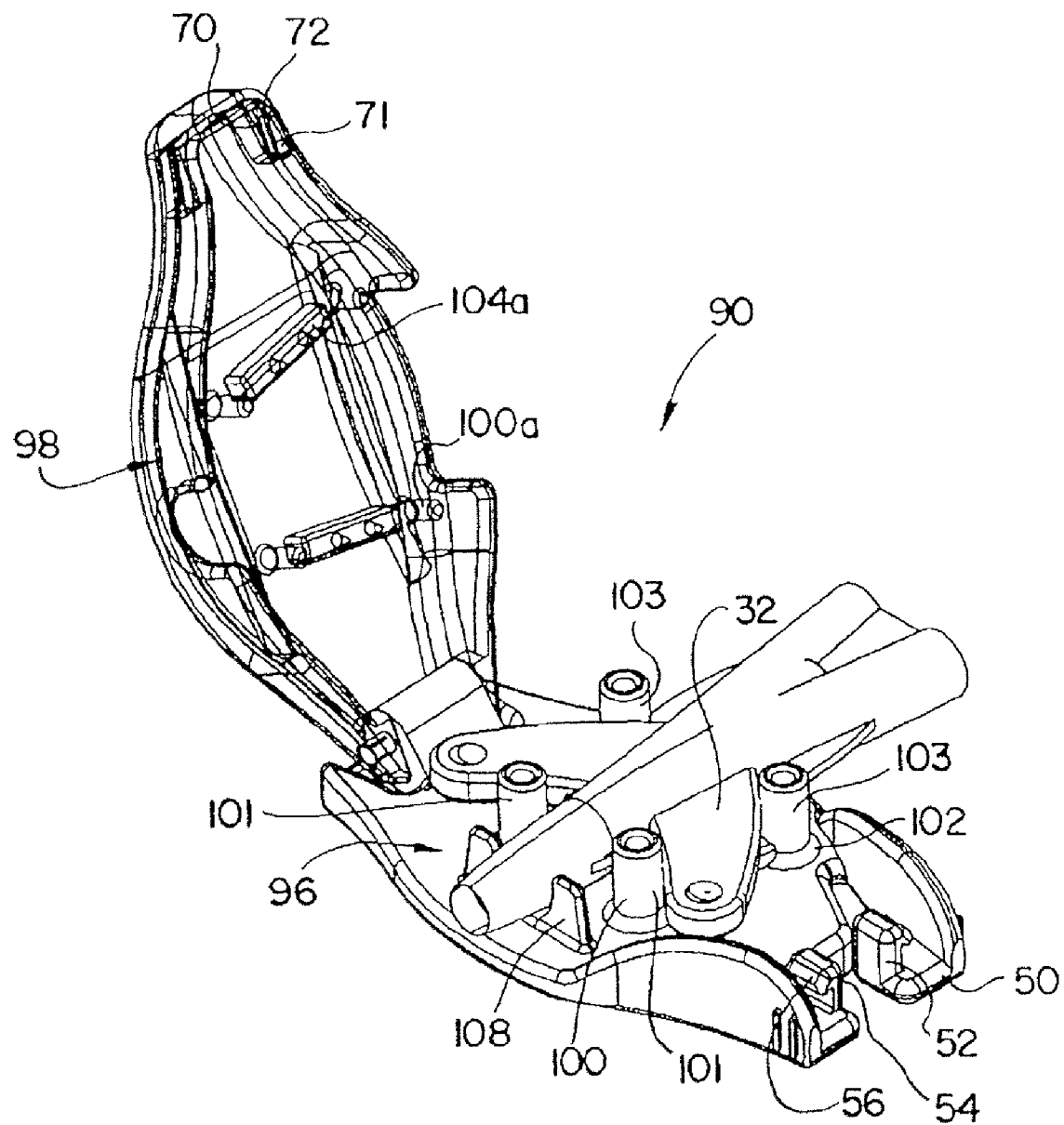
FIG. 10 is a top and front perspective view of another embodiment of a securing device with the cover lifted in an open position.

Referring again to FIGS. 2 and 4, as the top end 78 of the cover 28 is moved down onto the base 26 from an open position to a closed position, the angled surfaces 56 on the ends 54 of the latching elements 52 engage the inner surface of the front wall 84 and back wall 86, below the latch holes 70 on the cover 28. Alternatively, the angled surfaces 56 on the ends 54 of the latching elements 52 may engage the angled surfaces 72 of ridges 71, positioned below the latch holes 70 on the cover 28, e.g., as shown in the embodiment of FIG. 10. The latching elements 52 are somewhat resilient and can flex slightly under load in the longitudinal direction (along axis Y as shown in FIG. 1). As a result, as the cover 28 is moved down into engagement with the base 26, the latching elements 52 flex slightly inwardly toward each other. The angled surfaces 56 of the latching elements 52 and the inner surface of the front and back walls 84, 86 below the latch holes 70 on the cover 28 or the angled surfaces 72 of the ridges 71 slide against each other and pass by each other. The latching elements 52 then flex back to near their original longitudinal positions, forcing the ends 54 of the latching elements through the latch holes 70 in the cover 28 and locking the cover 28 onto the base 26. The catheter securing device 20 is then attached to the patient at the prepared securement site, usually via an adhesive pad. The securing device 20 then prevents virtually any movement of the catheter fitting 32 and adjoining catheter 30 within the securing device.

The catheter 30 may be removed by squeezing the squeezing arms 50 together, towards each other. One or both of the squeezing arms 50 may be resilient and flexible such that they may flex in the longitudinal direction. The squeezing arms 50 may be squeezed together by applying a force in the longitudinal direction, generally on the area of the grip ribs 59 located on the outer surface of the squeezing arm walls 57. Squeezing also causes the latching elements 52 on the squeezing arms 50 to move longitudinally toward each other, resulting in the ends 54 of the latching elements 52 moving back through and out of the latch holes 70. The latching elements 52 move toward each other such that the cover 28 can be lifted away from the latching elements 52. The angled surface 56 and angled surface 72 and/or inner surface of the cover 28 pass by each other as the cover 28 is pivoted up and off of the base 26.

The securing device described above may be attached to a patient in a variety of ways. As shown in FIG. 1, a base 26 may be attached to a pad 162 which is flexible to conform to the patient's arm or other site. The pad could be a hydro colloidal pad. The specific pad shape and size is not essential and various alternatives may be used. In FIG. 1, the pad 162 is generally oval or round and it can also be a small footprint of a base 26. The back side of the pad 162 preferably has one or more peelable strips over an adhesive layer or surface. The peel strips may be removed from the back of the pad 162, and the pad placed onto a prepared securement site. A cut out 164 may be provided at the front of the pad 162 to allow the base 26 to be closer to the incision or catheter entry point. Alternatively, the securing device may be affixed directly to a patient by applying adhesive tape around the device and against the patient's arm or other site.

Figure 11:
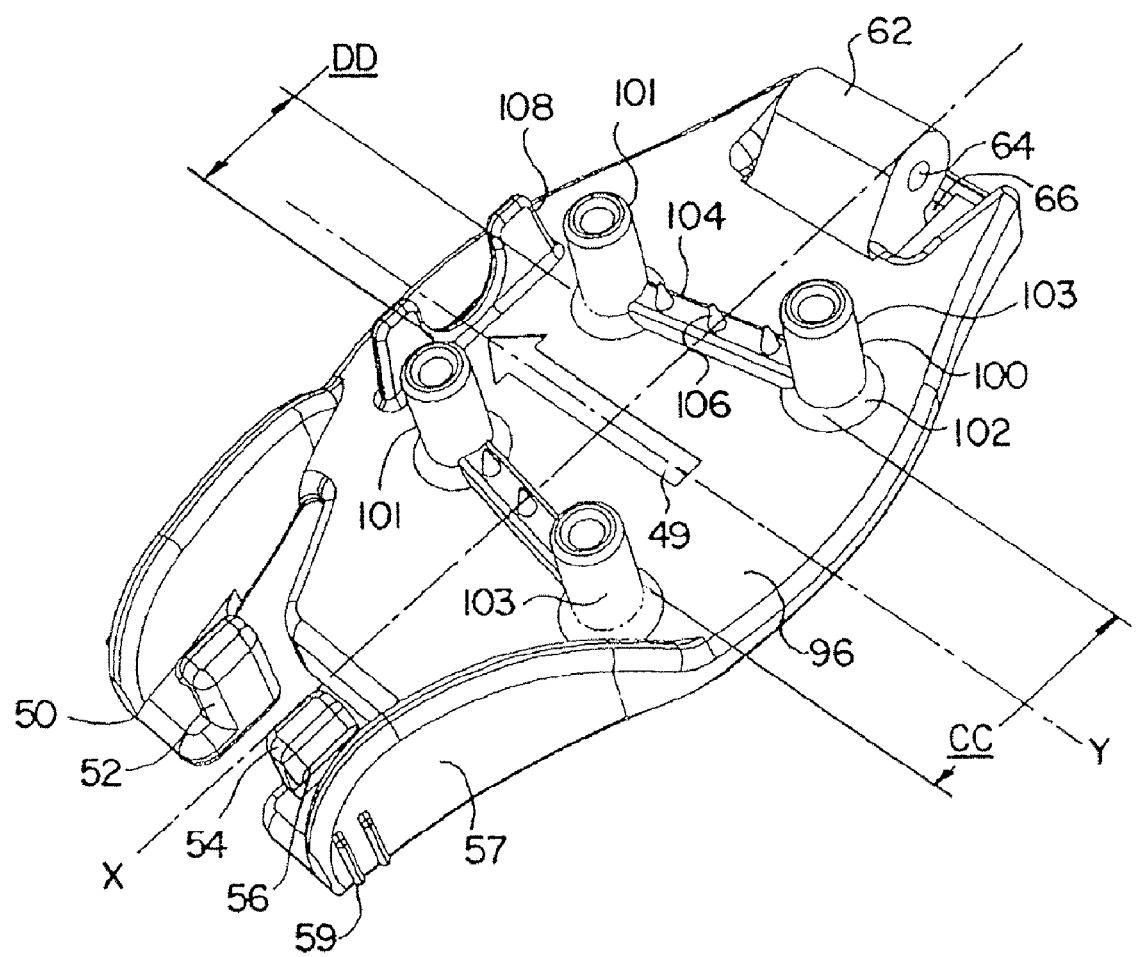
FIG. 11 is a top perspective view of the base of the securing device shown in FIG. 10.

FIG. 10 shows another embodiment 90 of a universal securing device. Securing device 90 has a base 96 and a cover 98. In this embodiment, as shown in FIG. 11, the locating elements extending up from the base 96 are locating pegs 100 and each peg is surrounded by a ridge 102 at the base of the peg. A front pair 101 and back pair 103 of locating pegs extend from the base 96 and are arranged in a configuration to position and hold a catheter and catheter fitting of various shapes and sizes and prevent substantial movement of such catheters and catheter fittings in various dimensions, similar to locating elements 40 described above.

As with the locating elements 40 shown above in FIG. 3, a first back locating peg 103 may be separated from a second back locating peg 103 by a dimension CC, while a first front locating peg 101 may be separated from a second front locating peg 101 by a dimension DD, as shown in FIG. 11. In one embodiment dimension CC may be greater than dimension DD. In another embodiment dimension CC may measure about 0.35 to 0.39 inches, preferably 0.36 to 0.38 inches, or more preferably 0.37 inches in length and dimension DD may be about 0.28 to 0.32 inches, preferably 0.29 to 0.31 inches, or more preferably 0.30 inches in length. In another embodiment, dimension CC may be about 130-170% of dimension DD or more preferably about 140-160% of dimension DD.

In addition, in FIG. 11, the locating pegs 100 positioned closest to the hinge block 62 and located above the arrow 49, may be connected generally horizontally by a capture element 104. The locating pegs 100 located below the arrow 49 and closest to the latching arms 50 may also be connected generally horizontally by a capture element 104. Spikes 106 may extend up from the surface of the capture elements 104. A semicircular trough 108, running generally parallel to the lateral axis X of the base 96 and positioned in front of the locating pegs 100 (as indicated by the arrow 49) may also extend up from the base 86. The spikes may optionally extend up from the surface of the base 86 in an embodiment without capture element 104.

Figure 12:
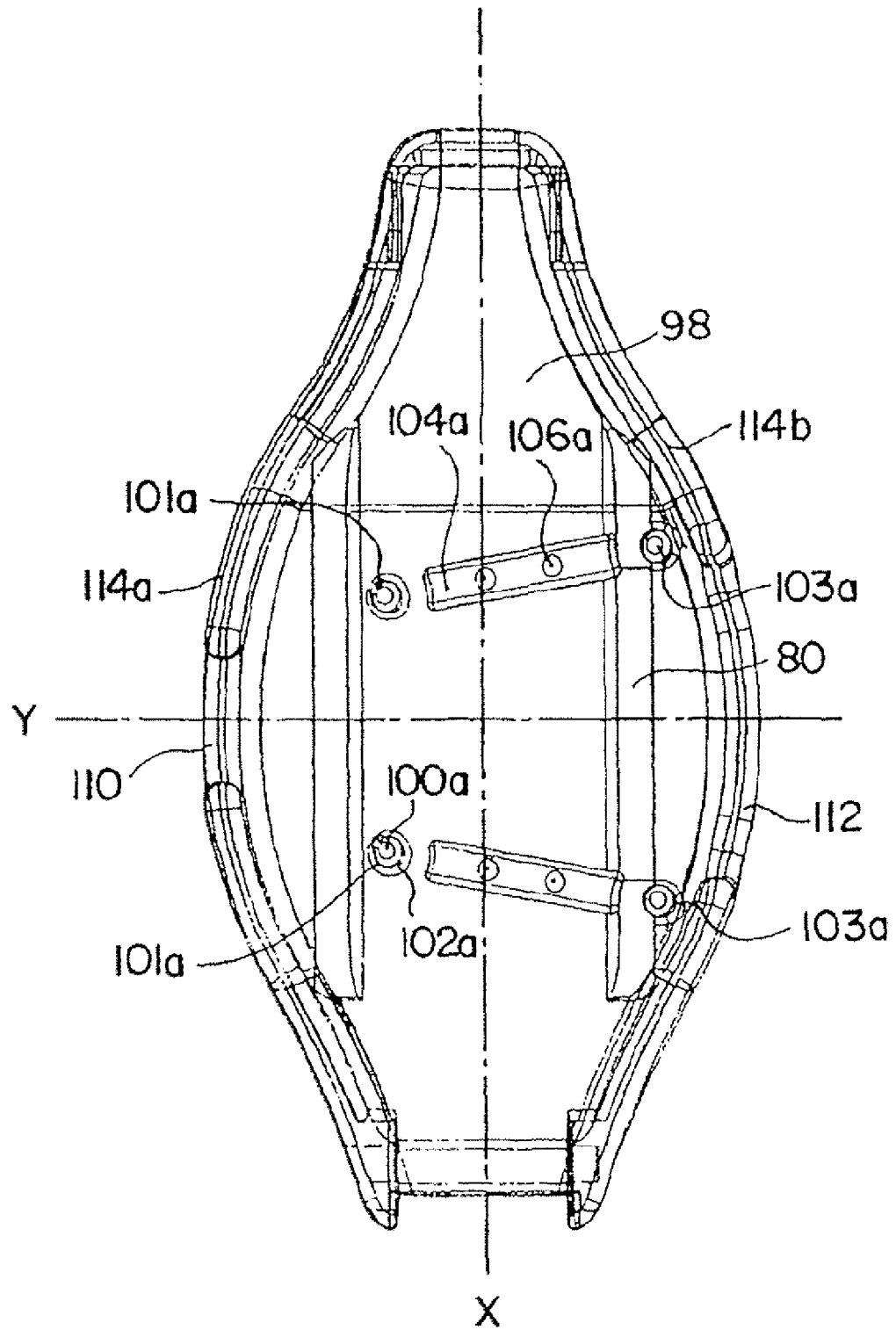
FIG. 12 is a plan view of the under side of the cover of the securing device shown in FIG. 10.
Figure 13:
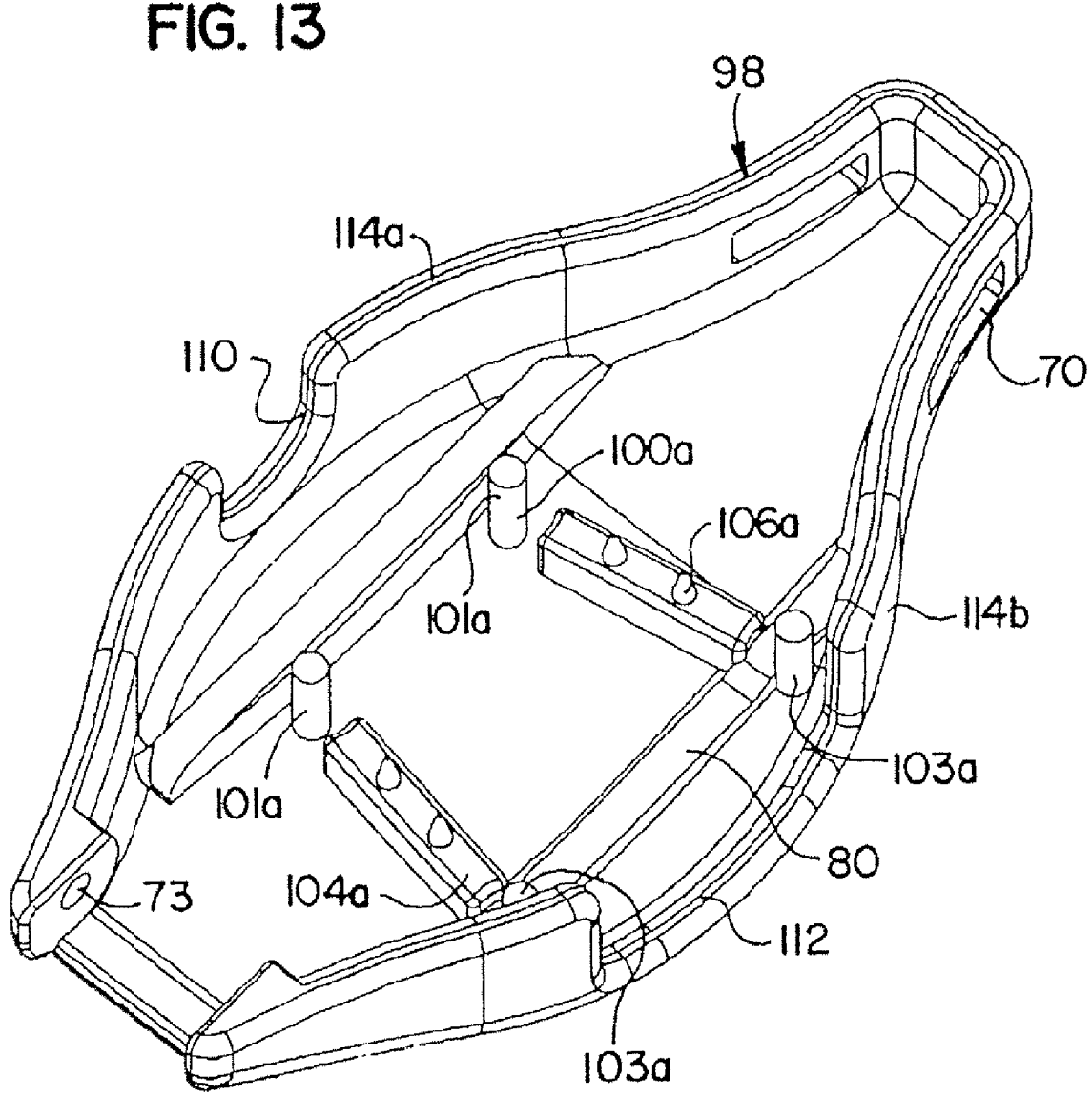
FIG. 13 is a top and back perspective view of the under side of the cover of the securing device shown in FIG. 10.

As shown in FIGS. 12-13, the cover 98 includes a first opening 110 in a front wall 114a and a second opening 112 in a back wall 114b. As best shown in FIG. 12 and with reference to the base 96 in FIG. 11, provided on the under side of the cover 98 are locating pegs 100a which are capable of fitting inside locating pegs 100 on base 96. The locating pegs on cover 98 include a front pair 101a and back pair 103a of locating pegs, each with ridges 102a as well at least one capture element 104a running between the locating pegs on the underside of the cover 98 arranged in a configuration that generally mirrors the configuration of locating pegs 100 and capture element 104 on the base 96. Spikes 106a may extend up from the capture elements 104a. The front pair 101a and/or back pair 103a of locating pegs may be positioned in between or outside bars 80, which are located on the underside of the cover 98 and run generally parallel to the lateral X axis (shown in FIG. 12). The capture elements 104 and 104a may be spring molded. Also, if desired, at least one locating peg 100a may be positioned at least partially on the surface of a bar 80. At least one capture element 104a may also be at least partially positioned on the surface of a bar 80. Father, with reference to FIG. 10, ridges 71, each having an angled surface 72, may optionally be provided below latch holes 70.

In one embodiment, the locating pegs 100a on the cover are connected by a capture element 104a which is positioned at an angle of about 1-45° to a longitudinal Y axis across the underside of the cover 98 and locating pegs 100 on the base 96 are connected by a capture element 104 which is positioned at an angle of about 1-45° to a longitudinal Y axis across the base.

Figure 14:
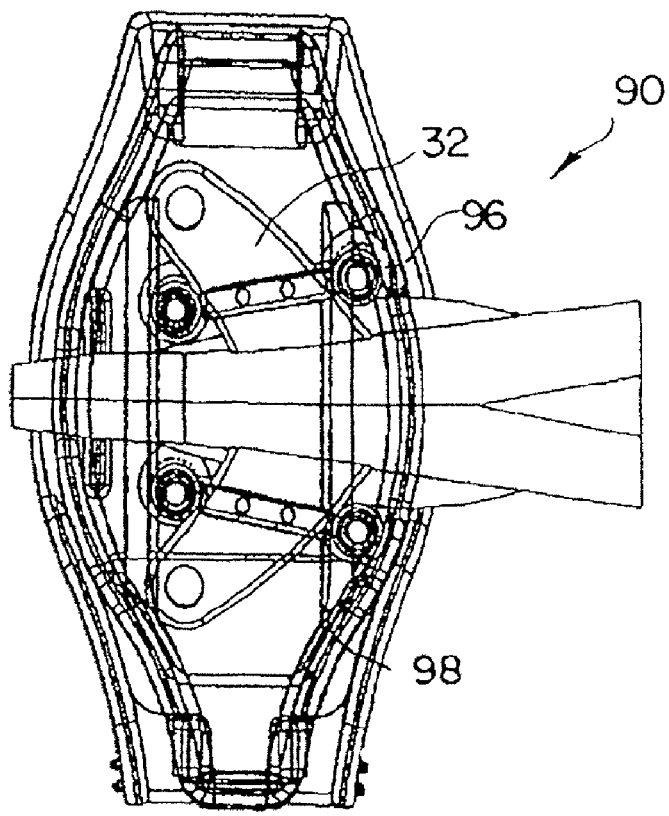
FIG. 14 is a plan view of the securing device shown in FIG. 10 in the closed position, holding a catheter fitting representative of various catheter fitting shapes and sizes.
Figure 15:
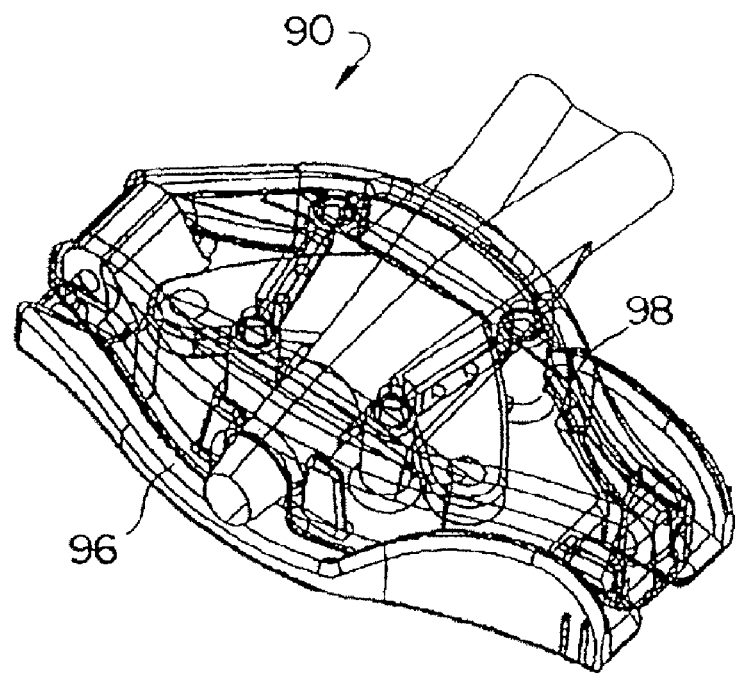
FIG. 15 is a top and front perspective view of the securing device shown in FIG. 10 in the closed position, holding an exemplary catheter fitting.
Figure 16:
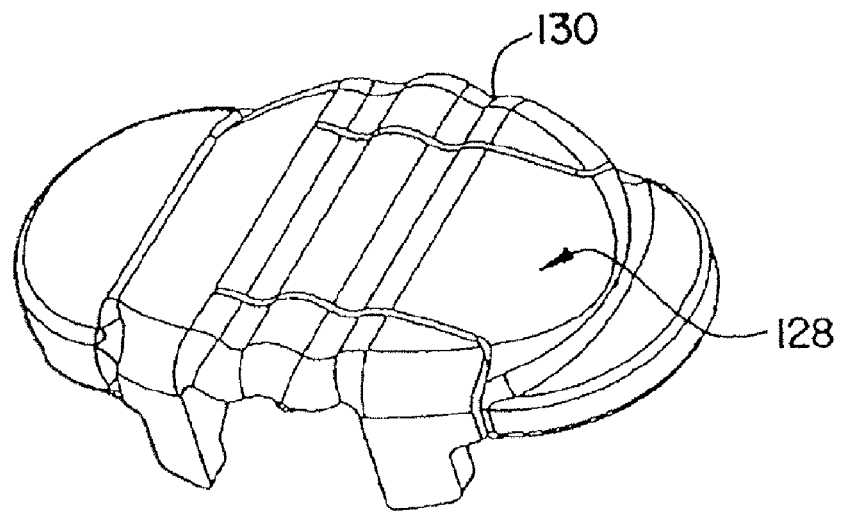
FIG. 16 is a top perspective view of the cover of another embodiment of a securing device.

The securing device 90 shown in FIGS. 10-15 operates in much the same way as the securing device 20, shown in FIGS. 1-9 and described above. Additionally, as cover 98 closes onto a catheter fitting 116 (or other catheter fittings of various sizes) which is positioned between the locating elements and latches onto base 96, locating pegs 100a may align with and engage locating pegs 100 as shown in FIGS. 14-15. This helps prevent cover 98 from shifting or moving, making the latching mechanism between latching elements 52 and latch holes 70 even more reliable. Also, spikes 106 and 106a are configured and arranged similar to the spikes in the embodiments of FIGS. 1-9 and described above. Thus, spikes 106 and 106a help compress and grip catheter fittings of various shapes and sizes such as catheter fitting 32, (e.g., by compressing the body and/or wings of the catheter fitting) securely holding the catheter fitting 32 in place and preventing substantial movement of the fitting in various dimensions as described above with respect to FIGS. 1-9.

Figure 48:
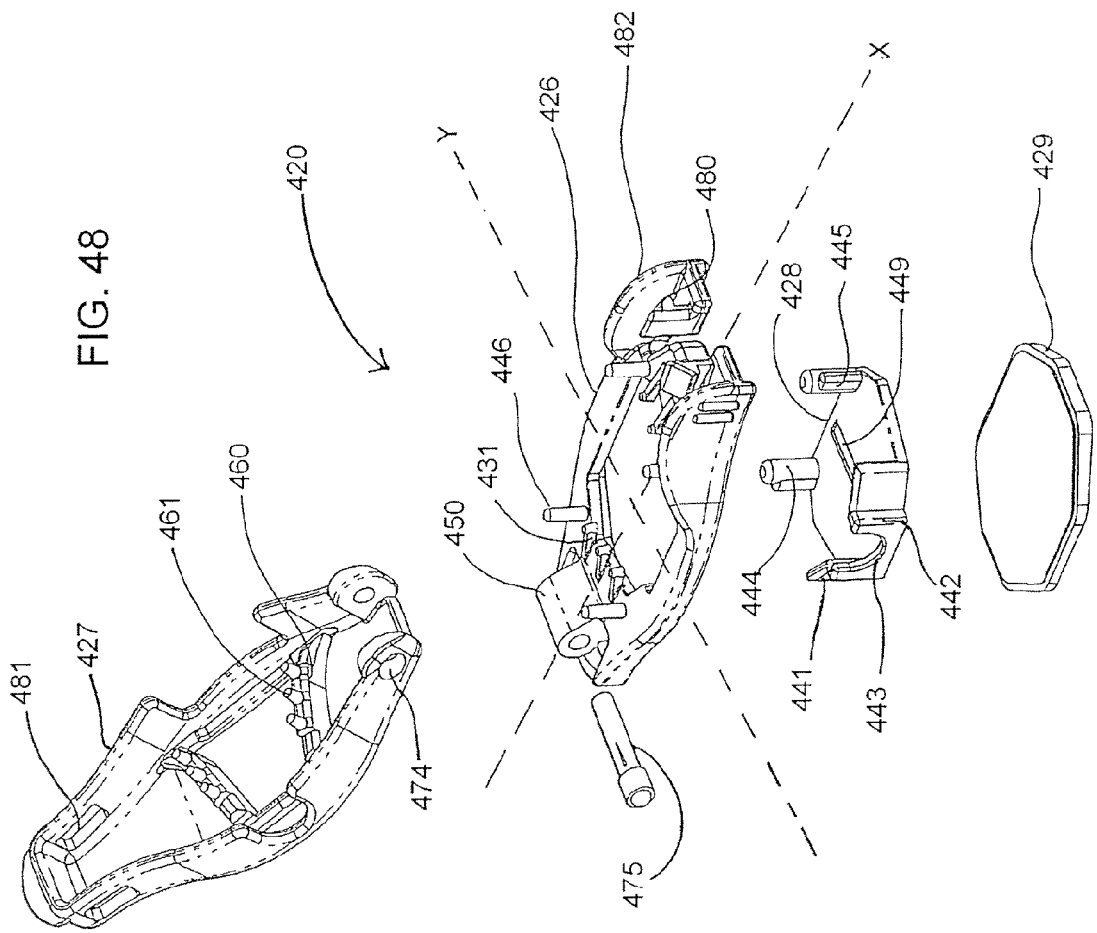
FIG. 48 is an exploded perspective view of a securing device.

In another embodiment, as shown in FIG. 48, a securing device 420 includes a base 426 and a cover 427. The cover 427 may be removably or permanently attached to the base 426 by a hinge 450. The base 426 includes an opening 430 configured to receive a retention plate 428 and a support plate 429 or seal plate or other structure suitable for holding or supporting the retention plate. The base 426 may include one or more restraining elements 431 attached to the top surface of the base 426 and extending at least partially over the opening 430. The restraining elements 431 may be, e.g., pins, pegs, bars, walls, extensions, etc. The base 426 may optionally include one or more alignment pins 446 extending up from the top surface of the base 426 to help guide and align the cover 427 over a catheter or catheter fitting positioned on the retention plate 428 during closing.

Figure 51:
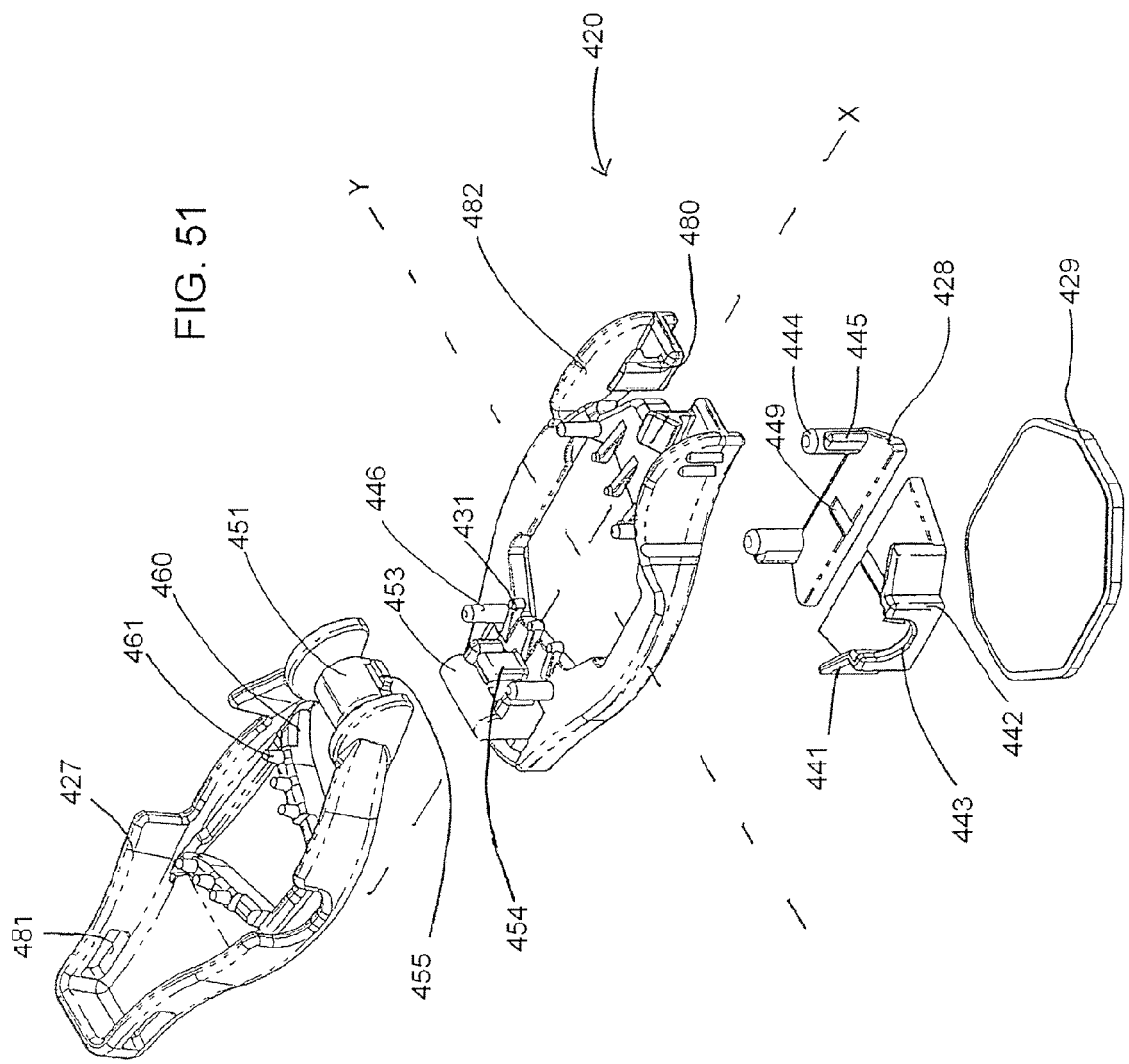
FIG. 51 is an exploded perspective view of a securing device.
Figure 52:
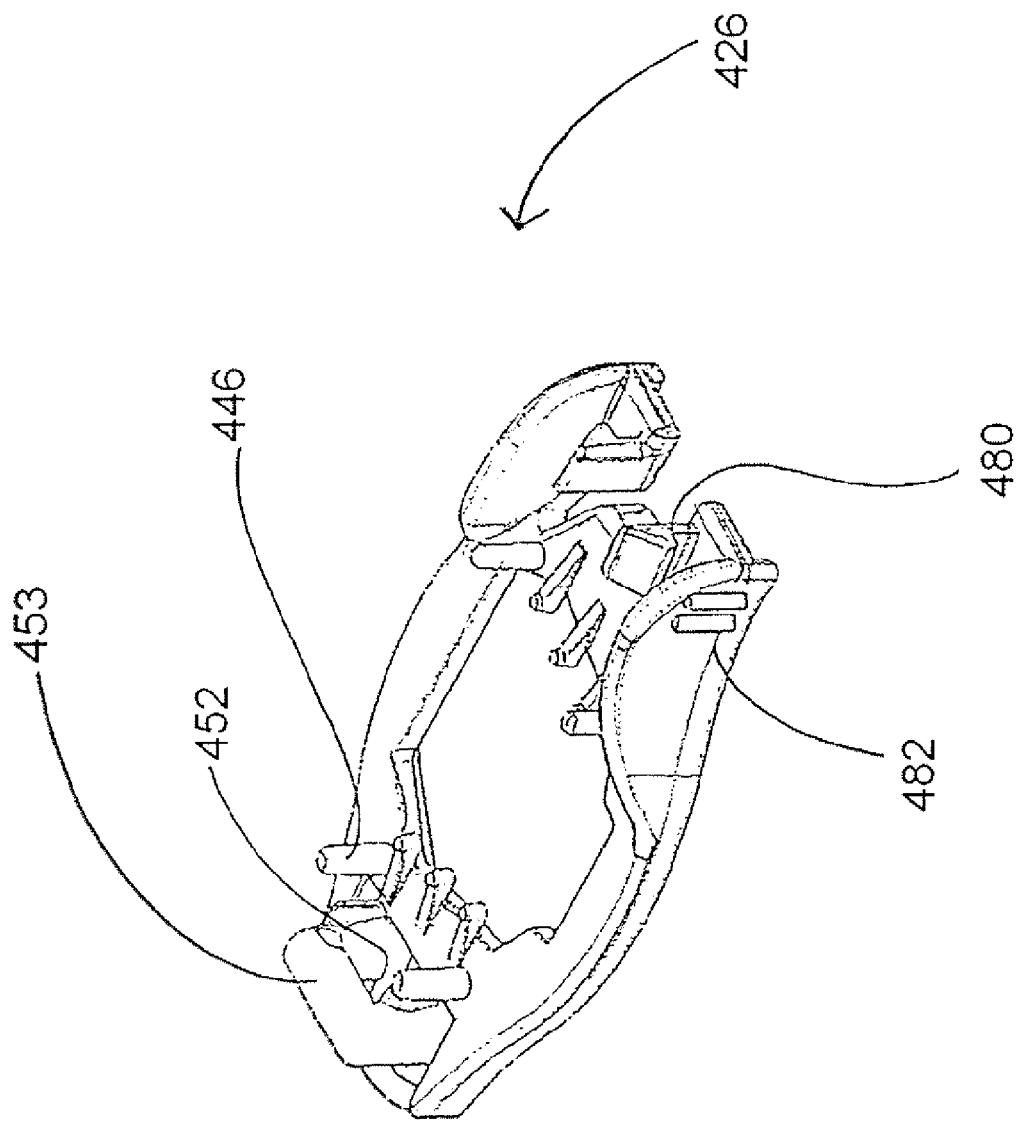
FIG. 52 is a front perspective view of a base of a securing device.
Figure 53:
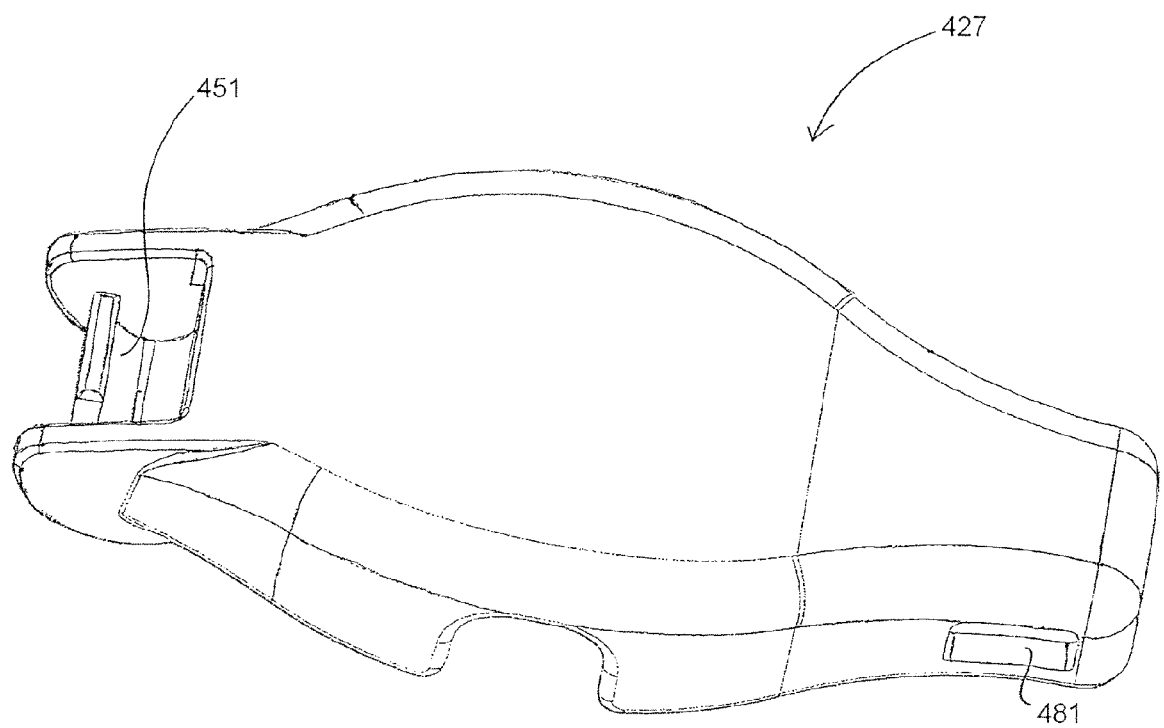
FIG. 53 is a top perspective view of a cover of a securing device.

The cover 427 may be temporarily or permanently coupled to the base 426 in a variety of ways. For example, as shown in FIG. 48, the base may include a hinge 450 which is configured to receive a pin 475. The pin 475 is inserted through a pin hole 471 in the cover 427 and through the hole in the hinge 450, thereby attaching the cover 427 to the base 426 such that the cover may rotate or pivot about the pin 475. In another embodiment, as shown in FIGS. 51-53, the base 426 may include a groove 452 and bar 453, and the cover 427 may include a tongue 451 or any other structures suitable for connecting the cover 427 to the base 426. The tongue 451 may be substantially arc shaped or may have any other shape suitable for attaching to the bar 453 or other structure on the base 426, or for inserting into the groove 452. In one embodiment, the arc shaped tongue 451 may have a perimeter greater than 180°. The tongue 451 may be engaged, connected, or snapped onto the bar 453 and/or pressed into the groove 452. The tongue 451 may rotate or pivot about the bar 453 or through the groove 452 when the cover 427 is moved into a opened or closed position, providing a type of hinge. Optionally, the tongue and groove or bar may provide a non pivotable or non rotatable connection.

Optionally, as shown in FIG. 51, a restraining arm 454 may extend from the base and be positioned near the bar 453 and groove 452, in between the opening 430 and the bar 453 and groove 452. A corresponding tab 455 may extend from the tongue 451. As the cover 427 is rotated into an opened position, the tongue 451 may contact the restraining arm 454, thereby stopping the rotation of the cover 427, and preventing the tongue 451 from being disengaged from the bar 453. The restraining arm 454, which may be flexible or resilient, can be flexed in a horizontal direction allowing the tab 455 to slide past the restraining arm 454 and the tongue 451 may then be disengaged from the bar 453. In other embodiments, the restraining arm 454 may be rigid and/or the cover 427 and base 426 may be permanently connected.

The base 426 may include one or more latching elements 480 positioned on the base 426 at an end generally opposite from the hinge 450 or other coupling structure. In one embodiment, as shown in FIG. 48, the latching elements 480, which fit into receiving holes 481 on the cover 427, may be connected to one or more squeezable arms 482 and operate to attach and detach the cover 427 to and from the base 426, as described above, e.g., in the embodiments of FIGS. 1-15. The cover 427 and/or base 426 may optionally include a latch or any other suitable attachment or fastening structure or mechanism for removably fastening or attaching the cover 427 and base 426 together in the closed position without the use of squeezable arms.

Figure 49:
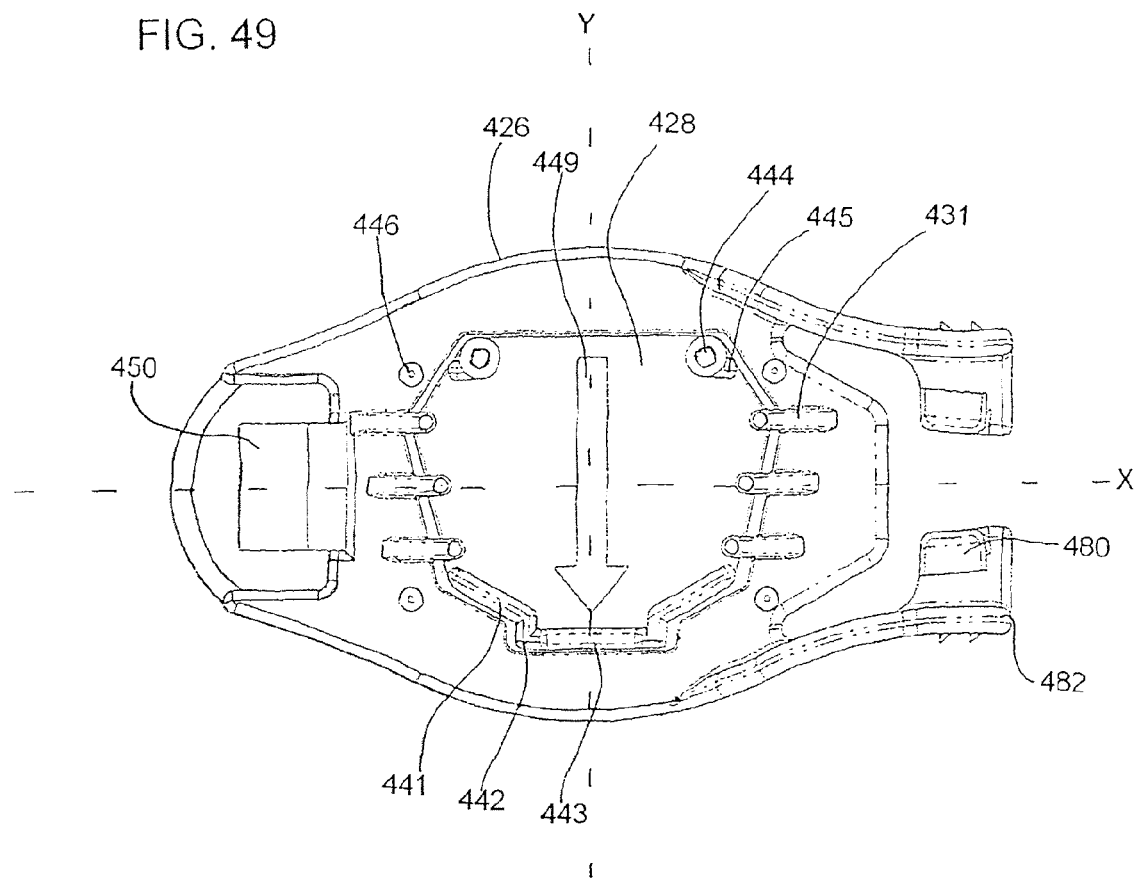
FIG. 49 is a plan view of the top surface of the base and retention plate of the securing device shown in FIG. 48.

As shown in FIGS. 48-49, the retention plate 428 preferably has a perimeter which is smaller than the perimeter of the opening 430 such that there remains some clearance between the perimeter of the retention plate 428 and the perimeter of the opening 430 when the retention plate 428 is positioned in the opening 430. The clearance space may be provided around the entire perimeter of the retention plate 428, around at least a portion of the retention plate 428 perimeter, or optionally no space at all may be provided around the retention plate 428 perimeter if the retention plate 428 is sized to fit against the perimeter of the opening 430. The clearance or space allows for movement of the retention plate 428 in a variety of dimensions, including, e.g., along the longitudinal Y axis, along the lateral X axis, or vertically. In any embodiment the retention plate 428 may be a single piece, or it may be made up of two or more separate pieces as shown in FIG. 51. Optionally, the retention plate 428 may be positioned at least partially in the opening 430. In other embodiments, the retention plate 428 may be positioned slightly above or below the opening 430.

Optionally, extending up from the retention plate 428 are locating elements. In the illustrated embodiments shown in FIGS. 48, 49 and 51, the locating elements positioned at the front of the retention plate 428 (as indicated by the arrow 449) each include a wall 441 connected to an elbow 442, which is connected to a generally semicircular receiving area 443.

This receiving area 443 may optionally be any other shape or design suitable for receiving a catheter, catheter fitting or other medical device. The locating elements positioned at the back of the retention plate 428 are in the form of locating pegs 444, and they may optionally have ridges or ledges 445 extending therefrom. Optionally, the front and back locating elements may be in the form of, e.g., walls, ridges, pegs, pins or any combination of these. Optionally, the locating elements may be positioned substantially symmetrical, side-to-side about the longitudinal axis of the securing device 420 or centerline Y, or arranged or positioned in any manner suitable to hold, position or restrain catheters or catheter fittings of various shapes or sizes to prevent substantial movement of the catheters or catheter fittings in one or more directions. Optionally, the locating elements may be configured, arranged, or positioned relative to each other, as detailed in the embodiments discussed above and below, to accommodate, hold, or restrain catheters or catheter fittings of various shapes or sizes.

Figure 50:
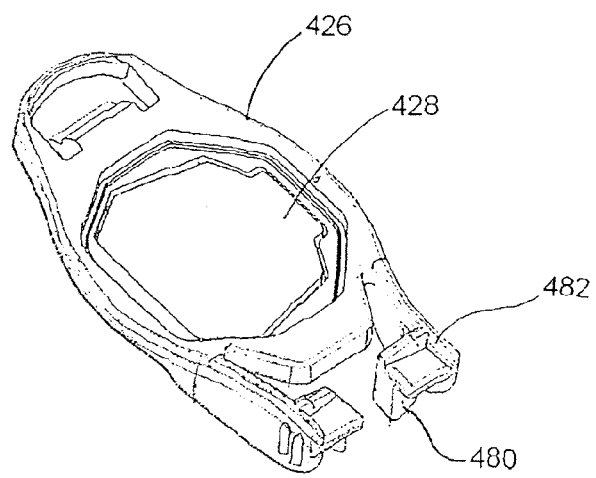
FIG. 50 is a bottom perspective view of the underside of the base and retention plate shown in FIG. 49 without the support plate in place.

As shown in FIG. 48, the support plate 429 preferably has a perimeter that is larger than the perimeter of the retention plate 428 but slightly smaller than the perimeter of the opening 430 such that the support plate 429 may be inserted into the opening 430. The retention plate 428 is inserted into the opening 430 from the back side of the base 426 and the restraining elements 431 prevent the retention plate 428 from falling through the front side of the base 426 (See FIGS. 49-50). The support plate 429 may be inserted at least partially into the opening 430 after the retention plate 428 has been inserted. The support plate 429 may be press fit into the opening 430 and held in place by friction to prevent the retention plate from falling through the back side of the base 426. Optionally the support plate 429 may be affixed within the opening 430 or to the base 426 by welding, gluing, insert molding, or by any other method suitable for temporarily or permanently attaching the support plate 429 within the opening or to the base 426. Alternatively, the support plate 429 may have a perimeter larger than the opening 430 and may be affixed to the bottom of the base 426 around the opening 430.

The top surface of the support plate 429 may optionally be substantially flexible, cushioned, resilient or constructed in any manner suitable to allow for movement of the retention plate 428 in a dimension up or down or vertically, e.g., relative to the base 426 or securing device 420. For example, such movement is permitted when the support plate 429 is attached to the base 426 and the retention plate is positioned on top of the support plate 429 and below the restraining elements 431. Accordingly, the retention plate 428 is substantially free floating or movable, which allows the securing device 420 to accommodate catheters or catheter fittings of various shapes, sizes, or thicknesses. Indeed, to secure a catheter in the securing device 420, a catheter is placed onto the retention plate 428 and the cover 427 is closed down over the catheter or catheter fitting. In one embodiment, the underside of the cover 427, capture elements 460, or pressure pins 461, spikes or posts may contact, compress, hold, restrain, or apply a downward force on the catheter or catheter fitting. As a result, the retention plate 428 may also be forced downward against the top surface of the support plate 429 allowing the securing device 420 to hold, restrain or accommodate catheters or catheter fittings of various shapes, sizes, or thicknesses. In another embodiment the support plate 429 may be substantially rigid or the retention plate 428 may be substantially flexible, or both may be substantially rigid or flexible.

Furthermore, the securing device 420 may be attached to a patient in a variety of ways. For example, an adhesive pad, as described in the above embodiments or an adhesive tape may be used for attaching the medical device to a patient. For example, an adhesive pad may optionally be attached to the base 426 or the support plate 429. Optionally, any other suitable attaching method or structure may be used.

Figure 54:
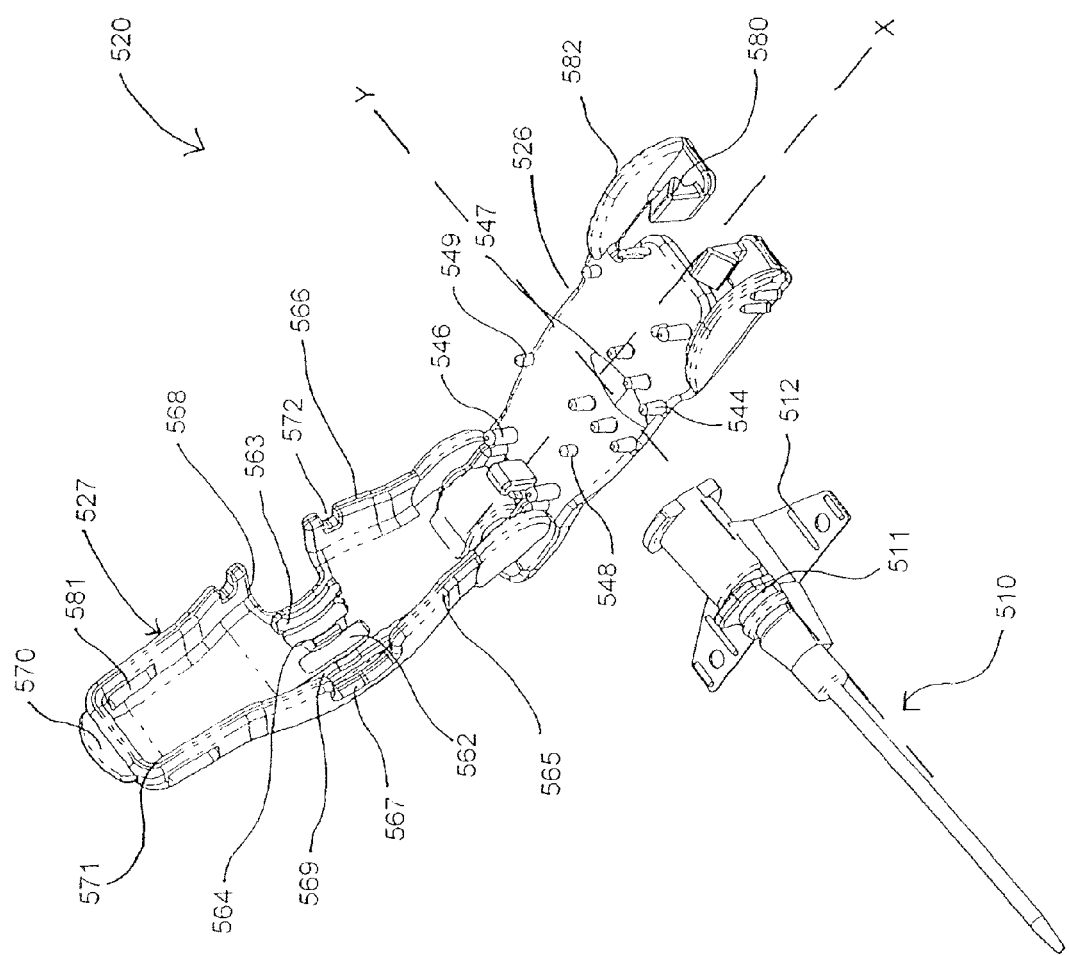
FIG. 54 is a top and front perspective view of another embodiment of a securement device with the cover lifted in an open position.

In another embodiment as shown in FIG. 54, a securing device 520 configured to receive a catheter or catheter fitting, e.g., an IV (intravenous) catheter, IV hub, IV luer, IV adaptor or any other similar medical tubing or medical accessory or tubing as well as other catheters or catheter fittings for use in other applications, includes a base 526 and a cover 527. The cover 527 may be removably or permanently attached to the base 526 by a hinge. The base 526 may optionally include one or more alignment pins 546 extending up from the top surface of the base 526 and positioned generally near the perimeter of the base 526 to help guide or align the cover 527 over a catheter 510 or catheter fitting positioned on the base 526 during closing of the securing device 520. The alignment pins 546 may optionally serve to receive, capture, or restrain flanges, wings or other parts of a catheter or catheter fitting in certain embodiments.

Optionally, the base 526 may include one or more locating elements, e.g., locating pegs 544, extending up from the surface of the base 526. The locating elements may take on a variety of forms, e.g., walls, ridges, pegs, pins or any combination of these. The base 526 may also include a receiving area 547. The receiving area 547 may be any shape or design suitable for receiving a catheter, a catheter fitting, e.g., a catheter hub 511, or any other medical device. Optionally, the receiving area 547 may have a generally oval or rectangular shape. The receiving area 547 may also be indented, recessed, sloped, or generally concave. In one embodiment, the receiving area 547 may be generally contoured to match the shape of a catheter hub.

In the embodiment shown in FIG. 54, the receiving area 547 is defined by a plurality of locating pegs 544, arranged in rows on either side of the receiving area. The locating pegs 544 may optionally have ridges or ledges extending therefrom. In one embodiment, the locating pegs 544 are positioned from the back of the base 526 to the front of the base 526 (as indicated by the direction of the catheter 510) in two rows forming a generally V-shaped or tapered arrangement suitable for receiving a standard catheter hub. In another embodiment, the locating pegs 544 may be arranged in rows running substantially parallel to the longitudinal Y axis of the device 520. Optionally, the locating pegs 544 may be positioned substantially symmetrically or offset, side-to-side about the longitudinal axis of the securing device 520 or offset, side-to-side from each other. They may also take on a linear arrangement or an offset staggered arrangement, longitudinally along the base 526. The locating pegs 544 may be arranged in any manner suitable to hold, position or restrain catheters or catheter fittings of various shapes or sizes to prevent substantial movement of the catheters or catheter fittings in one or more directions or dimensions, e.g., in an axial, side-to-side, back-to-front, up and down or rotational directions.

The base may also include two or more front locating pegs 548 and/or two or more back locating pegs 549 for receiving, capturing, or restraining the flanges 512, wings or other parts on a catheter or catheter fitting. The front and back locating pegs, 548, 549 may be spaced apart, side-to-side, by various distances to receive flanges, wings, or hubs of various shapes or sizes to help prevent movement of the catheter or catheter fitting in the longitudinal or lateral direction. Optionally, any of locating elements may be configured, arranged, or positioned relative to one another, as detailed in the embodiments discussed above and below, to accommodate, hold, or restrain catheters or catheter fittings of various shapes or sizes.

In the embodiment shown in FIG. 54, the base 526 may be contoured to match the anatomy of a patient, e.g., the arm, leg, or scalp, depending on where a catheter or other medical tubing is to be inserted and where the securing device 520 is likely to be placed. The base 526 is preferably shaped and configured to allow the maximum amount of catheter fitting or needle exposure or extension beyond the perimeter of the base, while still securing the catheter fitting in place. Thus, luer locks and other connectable components may be conveniently attached to an end of a catheter fitting, such as a catheter hub, and the needle or catheter can be properly inserted into a patient. The thickness of the base 526 may optionally taper in the longitudinal direction, gradually decreasing from the back to the front of the securing device 520. The base 526 may slope generally in the longitudinal direction, from the back to the front of the securing device at an angle suitable to facilitate insertion of a needle or catheter into a patient. In one embodiment, the angle may be about 4°-10° or 5°-9° or 6°-8°. Accordingly, a catheter fitting or catheter may be positioned on top of the sloped or angled base and be directed toward the patient at an angle that allows for optimum flow, delivery, or drainage of any fluid to and from a patient.

Figure 56:
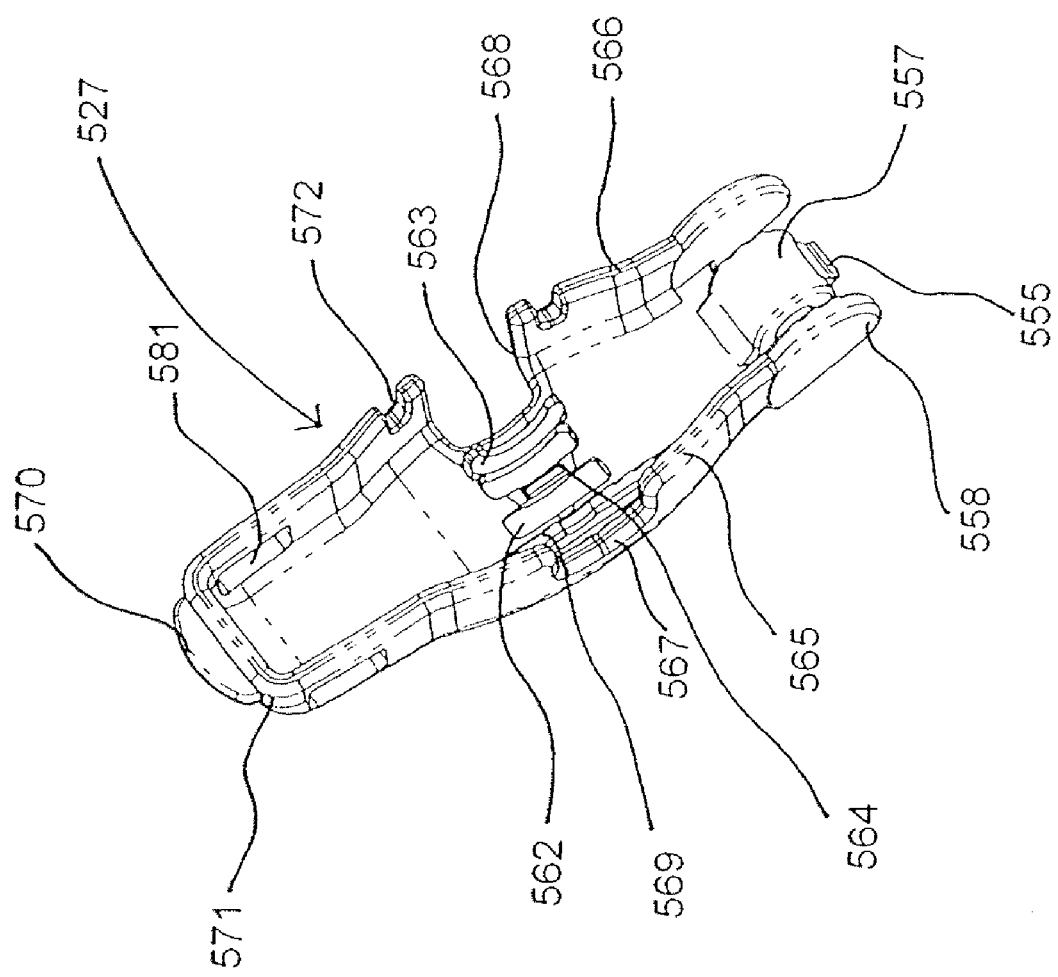
FIG. 56 is a perspective view of the underside of the cover of the securing device shown in FIG. 54.

As shown in FIGS. 54 and 56, the cover 527 may include a first opening 567 in a front wall 565 and a second opening 568 in a back wall 566 through which the ends of the catheter or catheter fitting extend. A tab 570 may extend from the latching end 571 of the cover 527 to facilitate opening and closing of the cover 527. In one embodiment, the cover 527 includes one or more receiving openings 562 located generally in the center of the cover 527 for receiving tabs or other extensions on a catheter fitting (e.g., a hub) to help hold the catheter fitting in place and prevent substantial rotational, longitudinal, or lateral movement of the hub.

One or more tabs 564 optionally extend from the underside of the cover 527 and may be positioned in between or adjacent to one or more receiving openings 562. The tabs 564 may be configured to extend in between corresponding tabs or into indents on a catheter fitting or against the fitting to help restrain, grip, or hold the catheter fitting in place or against the base 526. One or more contact ridges 563 may extend from the underside of the cover 527 and may be generally arc shaped or have any shape suitable to engage a catheter fitting and restrain, grip, or hold the catheter fitting against the base 526. The contact ridges 563 are preferably positioned on the underside of the cover 527 in between a receiving opening 562 and the second opening 568 or first opening 567. Preferably, the receiving openings 562, contact ridges 563, and tabs 564 are in alignment with the first opening 567 and second opening 568 generally along the longitudinal Y-axis of the cover 527.

The cover 527 may also have one or more bars 569 which run in a direction generally parallel to the lateral X-axis, along the underside of the cover 527. The bars 569 may optionally run at an angle of, e.g., 1-45 degrees from the lateral X axis. The bars 569 provide support or stiffness to, or minimize distortion or deflection of, the cover 527 when it is moved into a closed position in which it applies pressure to a catheter fitting on the base 526. In the embodiment shown in FIGS. 54 and 56, the bar 569 runs parallel to the lateral axis and is positioned adjacent to the front opening 567, while the contact ridge 563 is positioned adjacent to the back opening 568. The center area of the bar 569 may be generally recessed to accommodate the heights of catheter fittings having various shapes and sizes.

The front and back openings 567, 568 of the cover 527 are configured to allow passage of catheters and catheter fittings of various shapes and sizes, while assisting with alignment and securement of the same. Preferably, the front and back openings, 567, 568 are contoured to accommodate catheter fittings having various shapes. The front and back openings 567, 568 are also of sufficient size such that attachments, such as luer locks, will abut against the outer perimeter of the openings to further prevent longitudinal movement or pistoning of catheters and catheter fittings in the longitudinal direction. As shown in FIGS. 54 and 56, the center area of the cover 527 may be generally contoured, arched, or raised relative to the remainder of the cover 527 to accommodate catheter fittings of various sizes. Preferably, the center area of the cover 527 is angled in a manner that corresponds to the angle or slope of the base 526. In one embodiment, the angle is about 4°-10° or 5°-9° or 6°-8°. Accordingly, a catheter fitting or catheter may be restrained in the securing device 520 in a manner that directs the needle or catheter toward the patient at an angle that allows for optimum flow, delivery, or drainage of any fluid to and from a patient.

Furthermore, the cover 527 may include one or more indents 572 in the front or back walls 565, 566 of the cover for receiving the alignment pins 546 and aligning the cover 527 on the base as the cover 527 moves into or rests in the closed position. The cover 527 also includes one or more latching holes 581 for receiving latching elements 580 on the base 526. The latching elements 580 extend from squeezing arms 582 on the base 526, or extend directly from the base 526 in a manner described above with respect to FIGS. 2 and 4, to securely hold or lock the securing device 520 in the closed position. Also, either one or both of the cover 527 and base 526 may be preloaded in order to bend, bow, flex, or deflect around an IV or other catheter fitting as the base or cover apply pressure to the catheter or catheter fitting to secure it in place and prevent movement in various directions when the securing device 520 is in a closed position.

Figure 57:
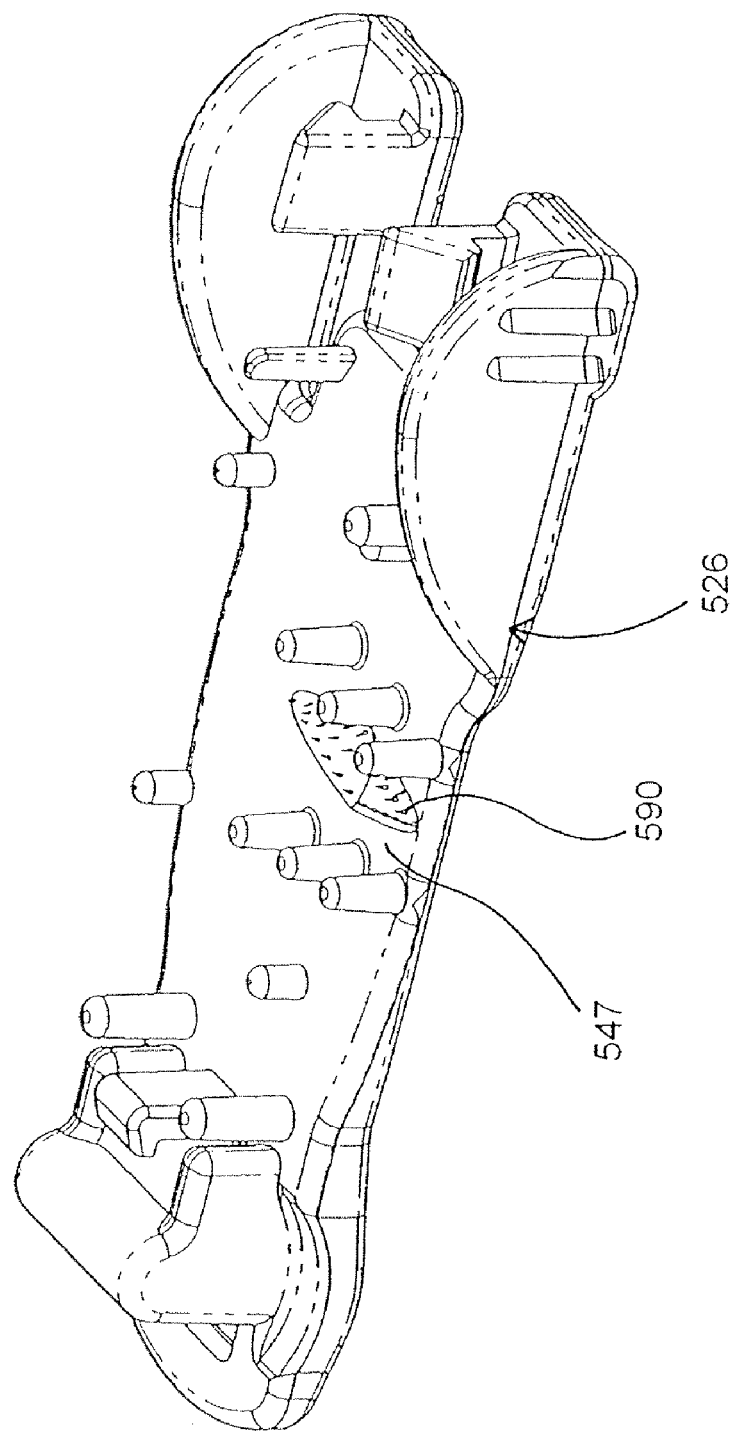
FIG. 57 is a top and side perspective view of another embodiment of a securing device.
Figure 58:
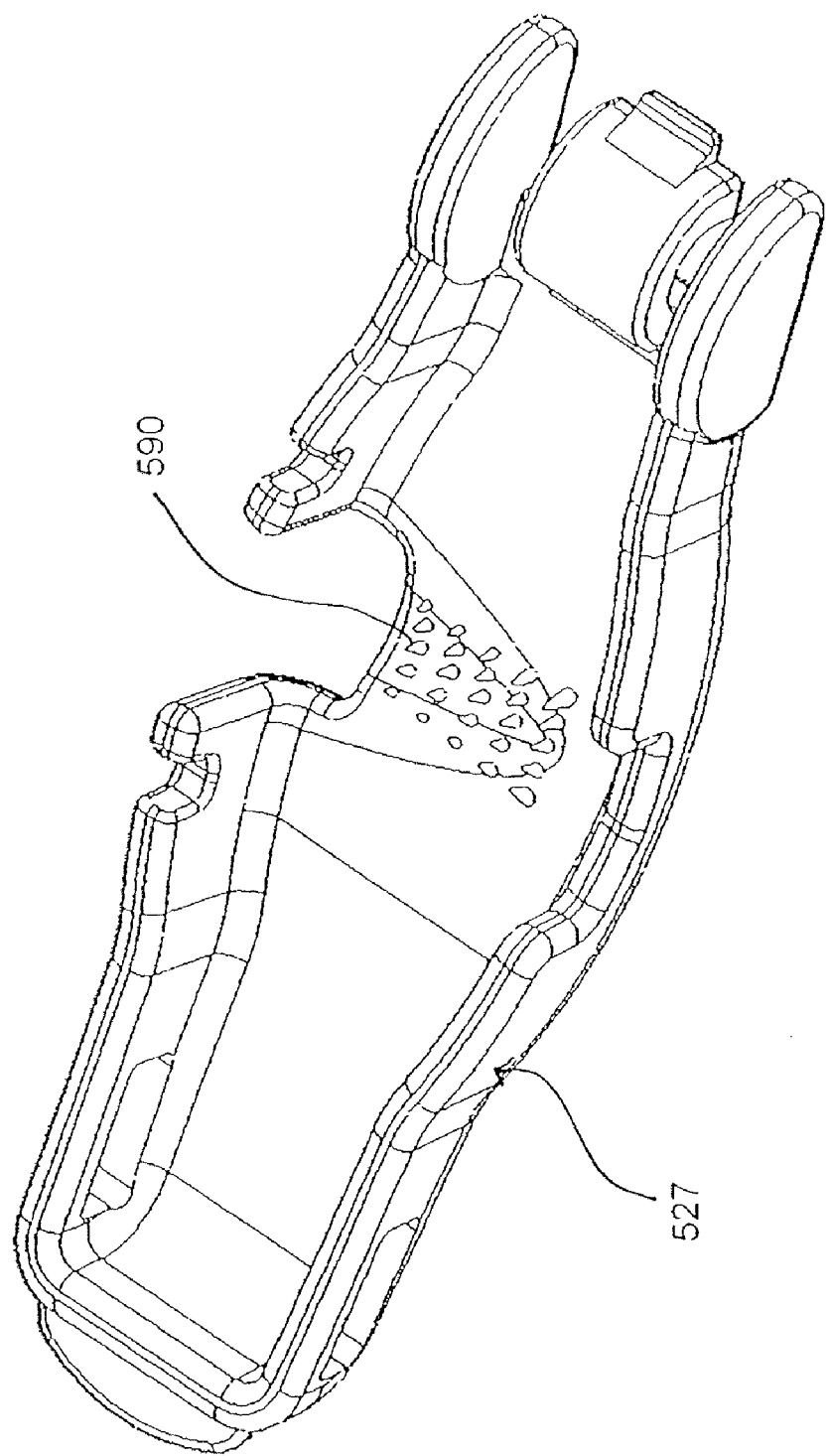
FIG. 58 is a perspective view of the underside of the cover of the securing device shown in FIG. 54.

In another embodiment, as shown in FIG. 57, one or more spikes 590, teeth, or other protrusions, may extend up from the receiving area 547 on the base 526. The spikes 590 are preferably made of metal or another hard substance suitable for pressing into, burrowing, or gripping a hard catheter fitting, e.g., a hub. The spikes may extend up directly from the receiving area 547, or they may be insert-molded into the receiving area. In one embodiment, a metal grid including a plurality of tiny teeth for gripping or biting into a catheter fitting may be inserted into the receiving area 547 of the base 526. When the cover 527 is closed down onto the base 526, the catheter fitting is forced against the spikes 590 which help to grip or hold the fitting securely in place. Optionally, as shown in FIG. 58, the cover 527 may include one or more spikes 590, teeth, or other protrusions, arranged in a configuration similar to the spikes 590 on the receiving area of the base 526. The spikes 590 on the cover 527 may also be insert-molded or may extend directly from the underside of the cover 527. Together, the spikes 590 on the cover 527 and base 526 press against the catheter fitting when the securing device is in the closed position, gripping and holding the fitting in place and preventing movement of the fitting in various directions or dimensions.

Figure 59:
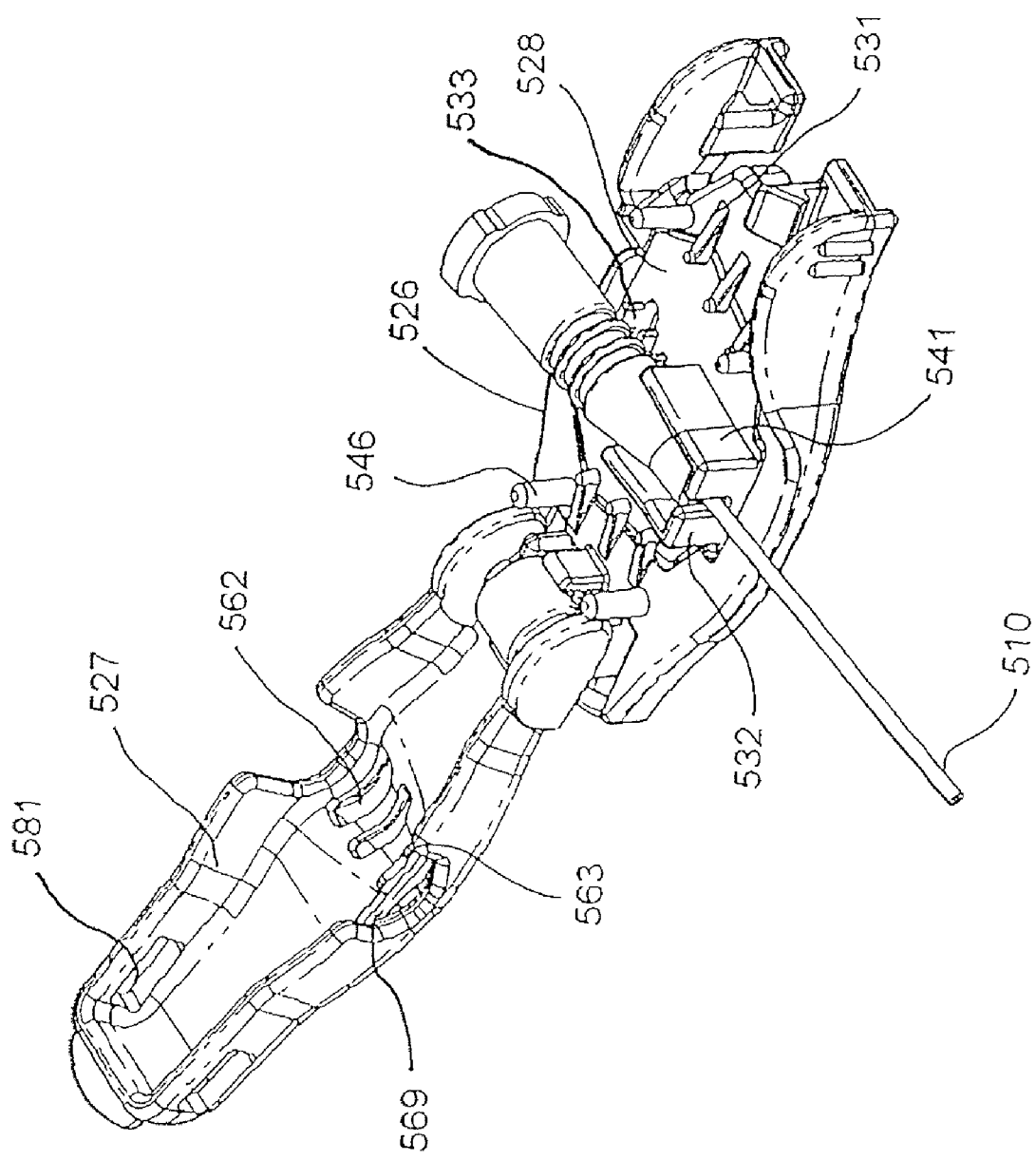
FIG. 59 is a top and front perspective view of another embodiment of a securing device with the cover lifted in an open position with a catheter shown.
Figure 60:
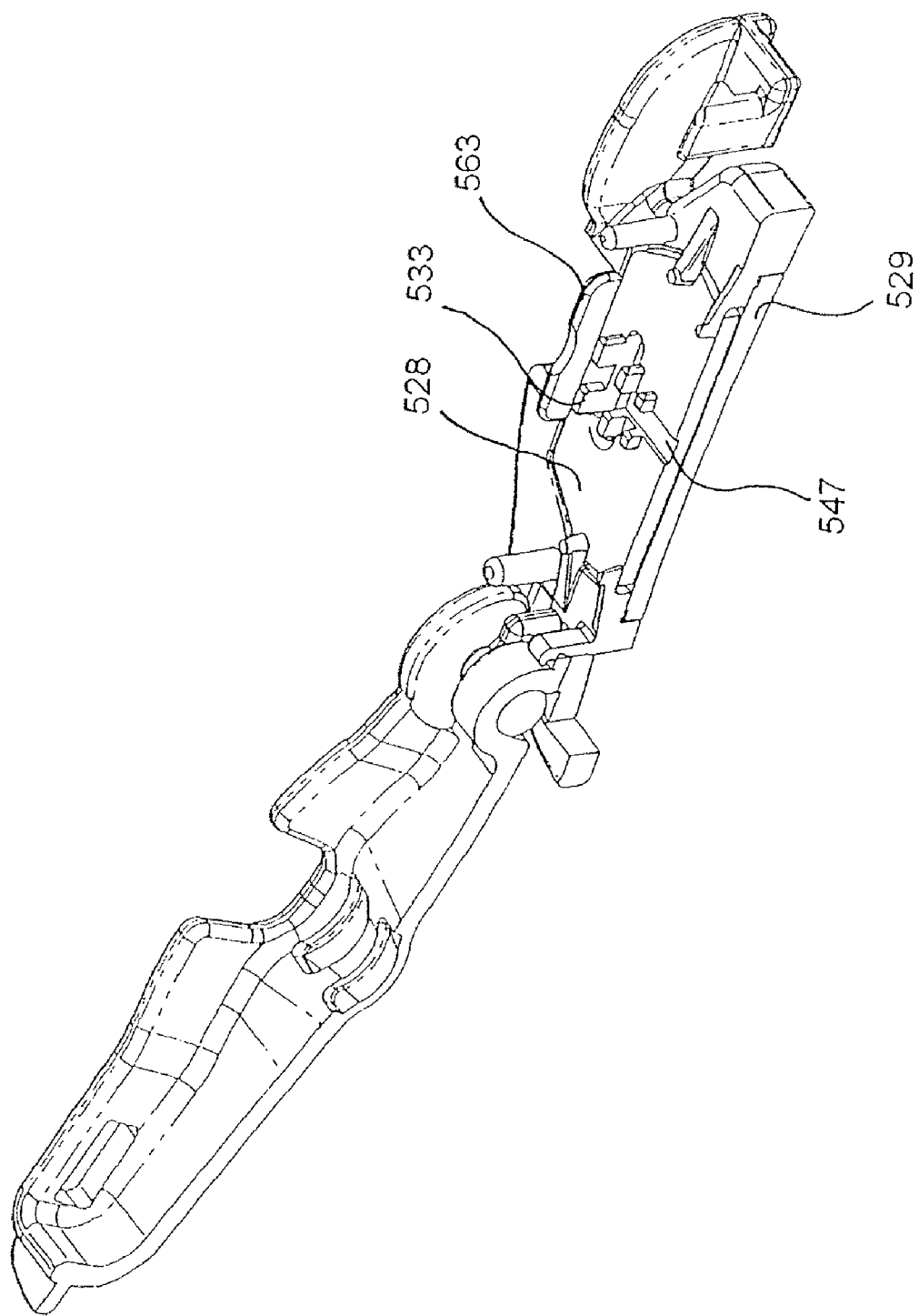
FIG. 60 is a cross sectional view of the securing device shown in FIG. 59 with the cover lifted in an open position.

In another embodiment, as shown in FIGS. 59 and 60, the base 526 may include an opening configured to receive a retention plate 528 and a support plate 529 or seal plate or other structure suitable for holding or supporting the retention plate 528. The base 526 may include one or more restraining elements 531 attached to the top surface of the base 526 and extending at least partially over the opening in which the retention plate 528 or support plate 529 may be positioned. The restraining elements 531 may be, e.g., pins, pegs, bars, walls, extensions, etc. The base 526 with opening, retention plate 528, support plate 529, and restraining elements 531 are configured and arranged in a manner as described above with respect to FIGS. 48-53, to create a floating base. The base may optionally include alignment pins 546 arranged generally around the perimeter of the base. Extending up from the retention plate 528 are one or more locating elements, e.g., pegs, walls, etc., which may be configured or arranged around a receiving area 547 (see FIG. 60) in any of the manners described above with respect to FIGS. 54-56. Optionally, the retention plate may include one or more spikes, teeth, or other protrusions extending up from the receiving area 547 or insert molded into the receiving area 547 of the retention plate 528, as shown in FIG. 57.

In one embodiment, as shown in FIGS. 59 and 60, the retention plate 528 may include locating elements in the form of two side walls 541 running generally parallel to the longitudinal Y axis on either side of the receiving area 547, which may be any suitable shape for receiving a catheter or catheter hub, e.g., rectangular, oval, etc. The side walls 541 are connected to a front wall 532 having an opening or receiving area through which a catheter, needle, or catheter fitting may extend. The side walls 541 and front wall 532 are arranged to receive or hold a catheter or catheter fitting, e.g., a catheter hub, and prevent substantial movement of the same in various dimensions. The walls are positioned generally toward the front of the retention plate 528, which is the side closest to the insertion site on a patient as indicated by the direction of the catheter 510.

Extending up from the back or rear area of the retention plate 528 may be one or more tabs 533. In one embodiment, a catheter fitting, e.g., a catheter hub, can be pressed onto or rest on top of the tabs 533, which may also extend in between corresponding tabs extending from the catheter fitting or into indents on the catheter fitting to help hold or align the catheter fitting onto the retention plate 528. The tabs 533 may be of various heights or sizes. Preferably, the tabs 533 are arranged side-by-side along the longitudinal axis, with each set of tabs 533 increasing in height from the front of the retention plate 528 toward the back of the retention plate 528 in order to support a catheter fitting at a preferred angle for directing a needle or catheter into a patient's skin. Optionally, the retention plate 528 may be angled or sloped as described above to have a similar effect. A contact ridge 563 may also extend up from the back of the retention plate 528. The above arrangements of walls, tabs 533, or contact ridge 563 may also be used with a non-floating base like the one described above in FIGS. 54-56.

The cover of the embodiment shown in FIGS. 59 and 60 may include one or more receiving openings 562 or bars 569. Extending form the bar 569 may be a contact ridge 563 for contacting a catheter hub or other catheter fitting and applying pressure to the catheter hub when the device is in the closed position. The cover 526 can rotate down onto the base by a hinge mechanism and latch into a closed position as described in the embodiments above. Optionally, the cover may be snapped onto the base for attachment.

Figure 61:
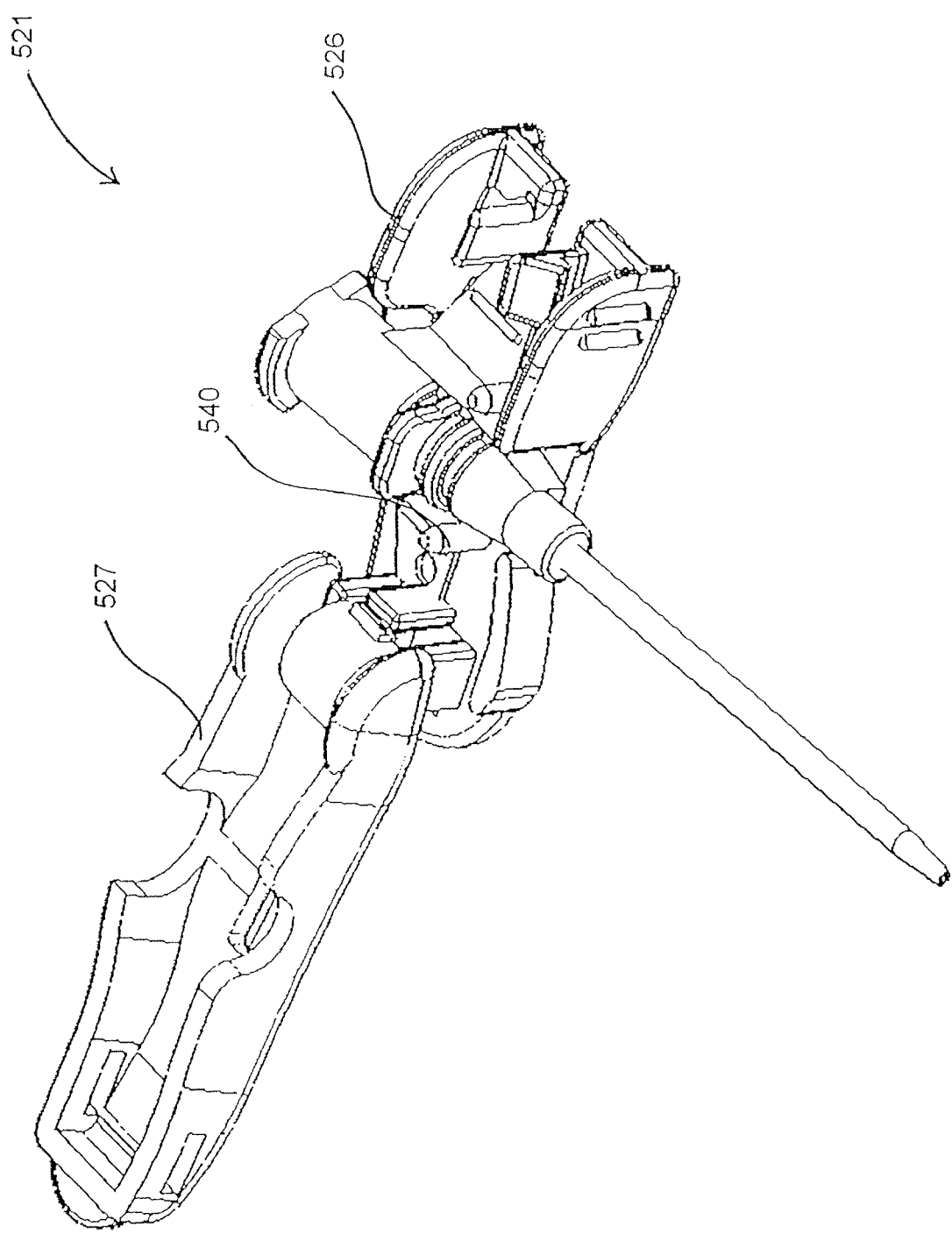
FIG. 61 is a top and front perspective view of another embodiment of a securing device with the cover lifted in an open position.
Figure 62:
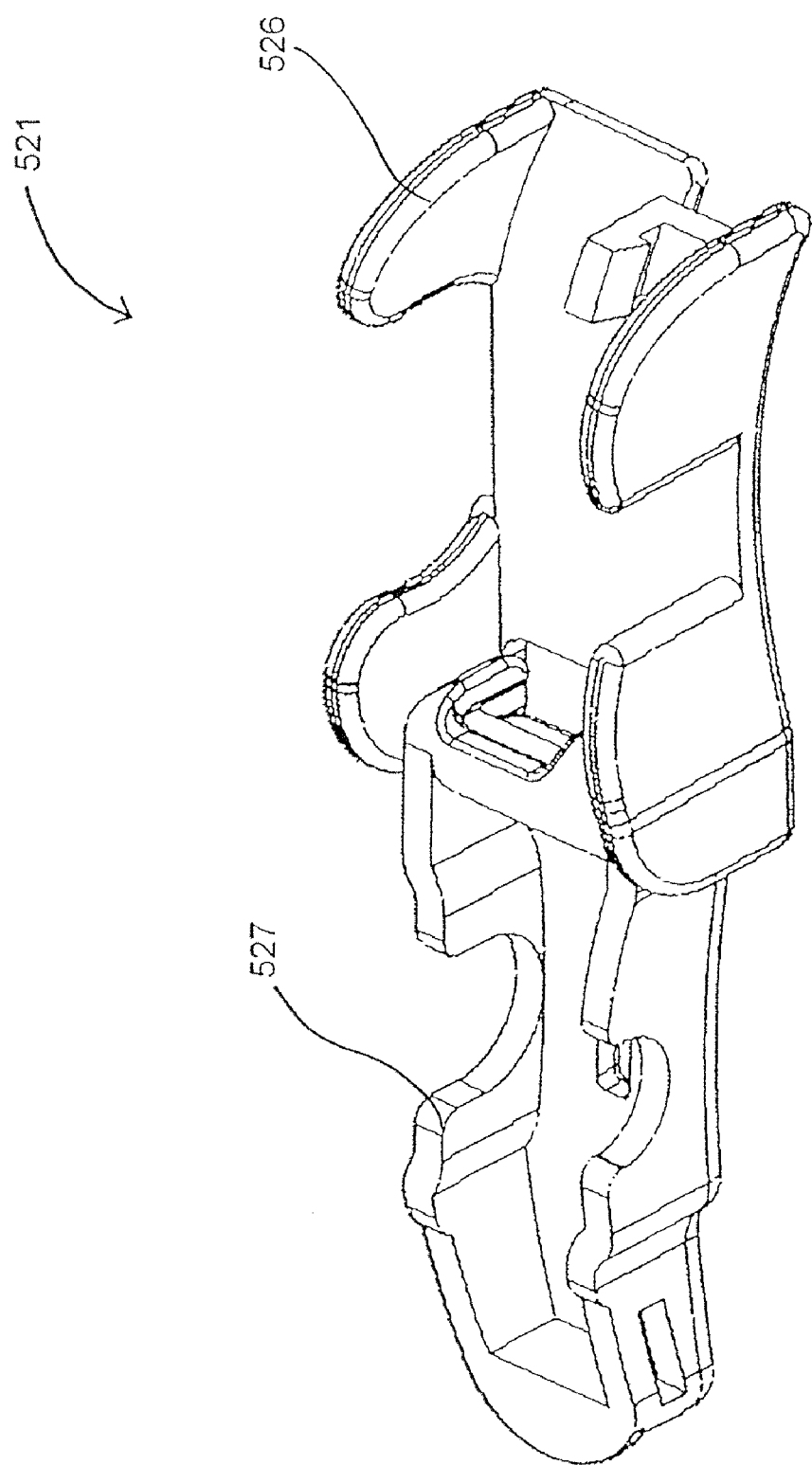
FIG. 62 is a top and side perspective view of the securement device shown in FIG. 61.

In another embodiment, as shown in FIGS. 61 and 62, the securing device 521 may include a base 526 and a cover 527. One or both of the surface of the base and the underside of the cover may be smooth or flat. The base or cover may apply pressure to the catheter fitting when the securing device is in the closed position, thereby holding or securing the catheter or catheter fitting in place and preventing movement in various directions or dimensions. Optionally, one or more locating elements 540 may extend up from the base 526 to receive, hold, or align the catheter or catheter fitting in place or to hold the flange or wings of a catheter fitting and prevent longitudinal or lateral movement of the fitting. Alignment walls or bars may also extend up from the base. The front walls of the base 526 and cover 527 may be generally arched or curved such that the front end of the catheter fitting remains in close proximity to the patient. Furthermore, the floating base configuration described above with reference to FIGS. 59 and 60 may be implemented in any of the embodiments shown in FIGS. 54-58 and 61-62.

Figure 55:
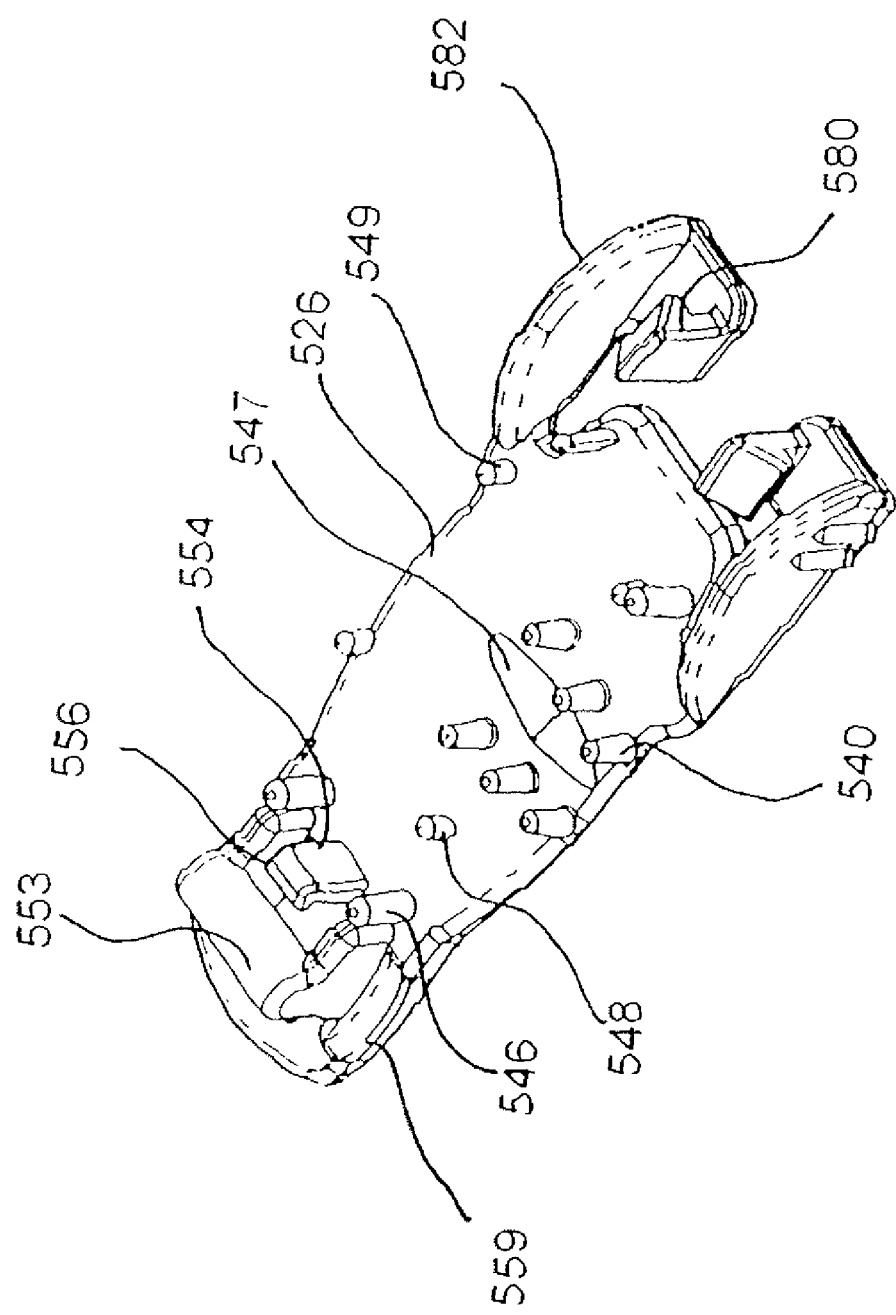
FIG. 55 is a top and front perspective view of the base shown in FIG. 54.

In any of the above embodiments, the base 526 may be permanently or removably attached to the cover 527. The cover 527 may rotate onto and off of the base using any of the hinge mechanisms or snapping attachments described above. Additionally, as shown in FIGS. 55 and 56, the cover 527 may include an inner cam 557 or tongue and generally rounded outer cams 558. The inner cam 557 is attached to a bar 553 around which it may pivot or rotate. The bar 553 serves to center, align, stabilize, or locate the cover 527 on the base 526 to prevent substantial side-to-side movement as it rotates. As the cover 527 rotates, the outer cams 558 engage the corresponding rounded follower surfaces 559 on the base 526 which also serves to center, align, stabilize, or locate the cover 527 as it rotates. A tab 555 extending from the inner cam 557 may engage the ridge 556 on a restraining arm 554 which extends from the base to prevent over rotation of the cover 527 or detachment of the cover 527 when it is in the open position. Overrotation or removal may be performed by applying additional force to slide the tab 555 past the ridge 556.

In an embodiment of the securing devices described above, the securing device may limit the axial motion of an IV Hub or other catheter fitting or catheter to +/−1.5 mm. The securing device may secure an IV Hub to within its travel limit when subjected to a pull force of up to about 3 lbs in any direction on any one of its tubes or catheters. The securing device may not open when any one of the tubes or catheters is pulled with a force up to about 3 lbs in any direction and the cover shall remain secured with up to about 5 lbs of applied force in any direction. An adhesive Tricot may be bonded to the bottom surface of the securing device for attachment to the patient's skin and the base shall not separate from the adhesive with less than about five lbs of force. The cover may optionally be clear to allow a user to view the IV hub once the device is closed. The base may also be clear. The securing device may have an arrow molded or printed on the base or cover to indicate the direction of flow toward the catheter distal end and aiding in orienting the catheter when it is put in place. The cover may open with a maximum applied force from the user of about 5 lbs to the tab. The cover may close with a maximum applied force from the user of about 4 lbs.

Figure 63:
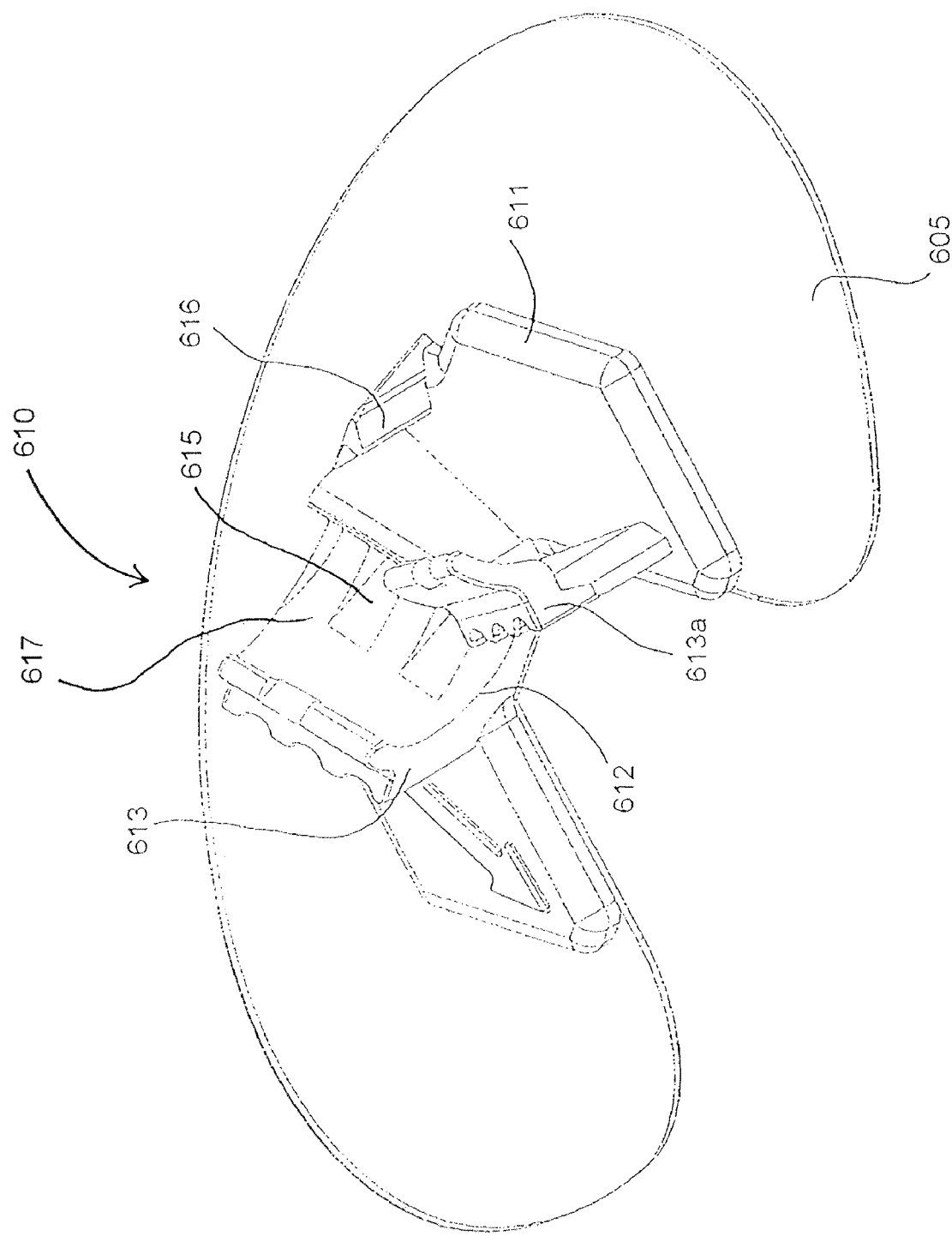
FIG. 63 is a top and front perspective view of another embodiment of a securing device attached to an adhesive pad.
Figure 64:
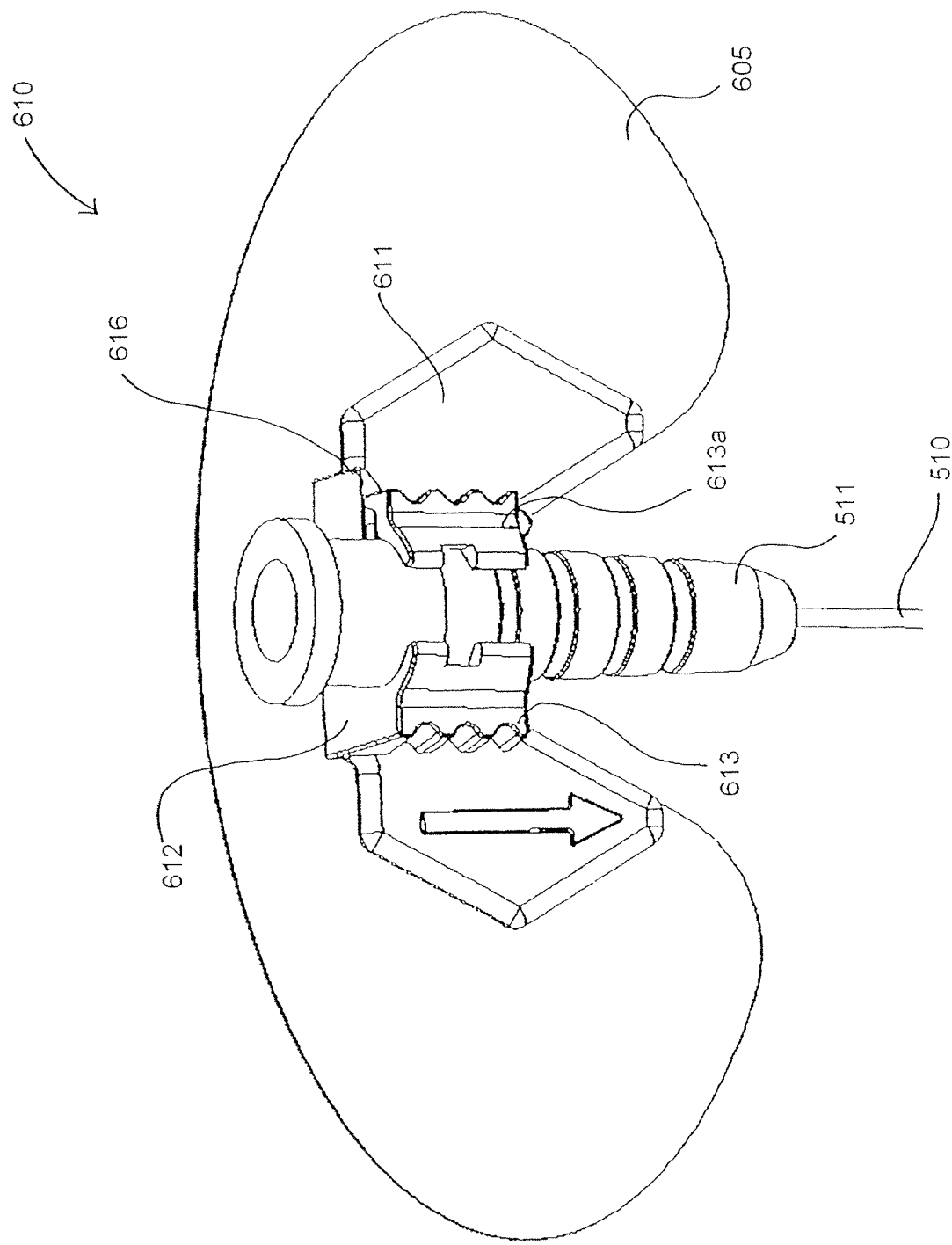
FIG. 64 is a top view of the securing device shown in FIG. 63.

In another embodiment, as shown in FIGS. 63 and 64, a securing device 610 includes a base 611. A receiving area 612, which may be substantially arc shaped, semi-cylindrical, or generally contoured to receive or hold a catheter hub or other catheter fitting, may be positioned on the center of the base 611. The receiving area 612 may be flexible or resilient to accommodate various catheter fittings. The receiving area 612 extends generally along the longitudinal Y axis and is bordered on either side by restraining walls which run generally parallel to the longitudinal Y axis. Preferably, one restraining wall 613 is fixed and the other is movable, forming a swinging gate 613*a*. The fixed wall 613 may optionally be a separate piece or an extension of the receiving area 612. The swinging gate 613*a* may open by applying pressure to a deflectable, resilient, flexible, or spring loaded tab 616 or other latching mechanism to disengage the tab 616 from the swinging gate such that the swinging gate 613a may pivot or rotate in the lateral direction, away from the receiving area 612. A catheter or catheter fitting may then be positioned onto the inner surface 617 (shown in FIG. 63) of the receiving area 612 which faces away from a patient when the securing device is positioned on a patient. In one embodiment, the inner surface 617 of the receiving area 612 may include one or more receptacles 615 (shown in FIG. 63) or indents for receiving tabs or other extensions on a catheter hub or other catheter fitting to hold the catheter in place on the securing device 610 and prevent substantial longitudinal movement or movement in other directions or dimensions.

Once the catheter hub is in place, the swinging gate 613a is rotated back toward the receiving area 612. The swinging gate engages the tab 616 and slides past the tab 616, which can flex slightly under the load and then return to its original position, latching or locking the swinging gate 613a into place and securing the catheter fitting within the receiving area 612. In another embodiment, the securing device may be designed such that the base 611 includes two parts extending from either side of the receiving area 612, where the bottom surface of the receiving area and/or the bottom surface of the base 611 are attached to an adhesive pad or a patient. Optionally, the base 611 is contoured to the anatomy of a patient or is slightly resilient or flexible to form to the anatomy of a patient. A pad 605 may be attached to the underside of the base 611 to adhere the device to a patient.

Figure 65:
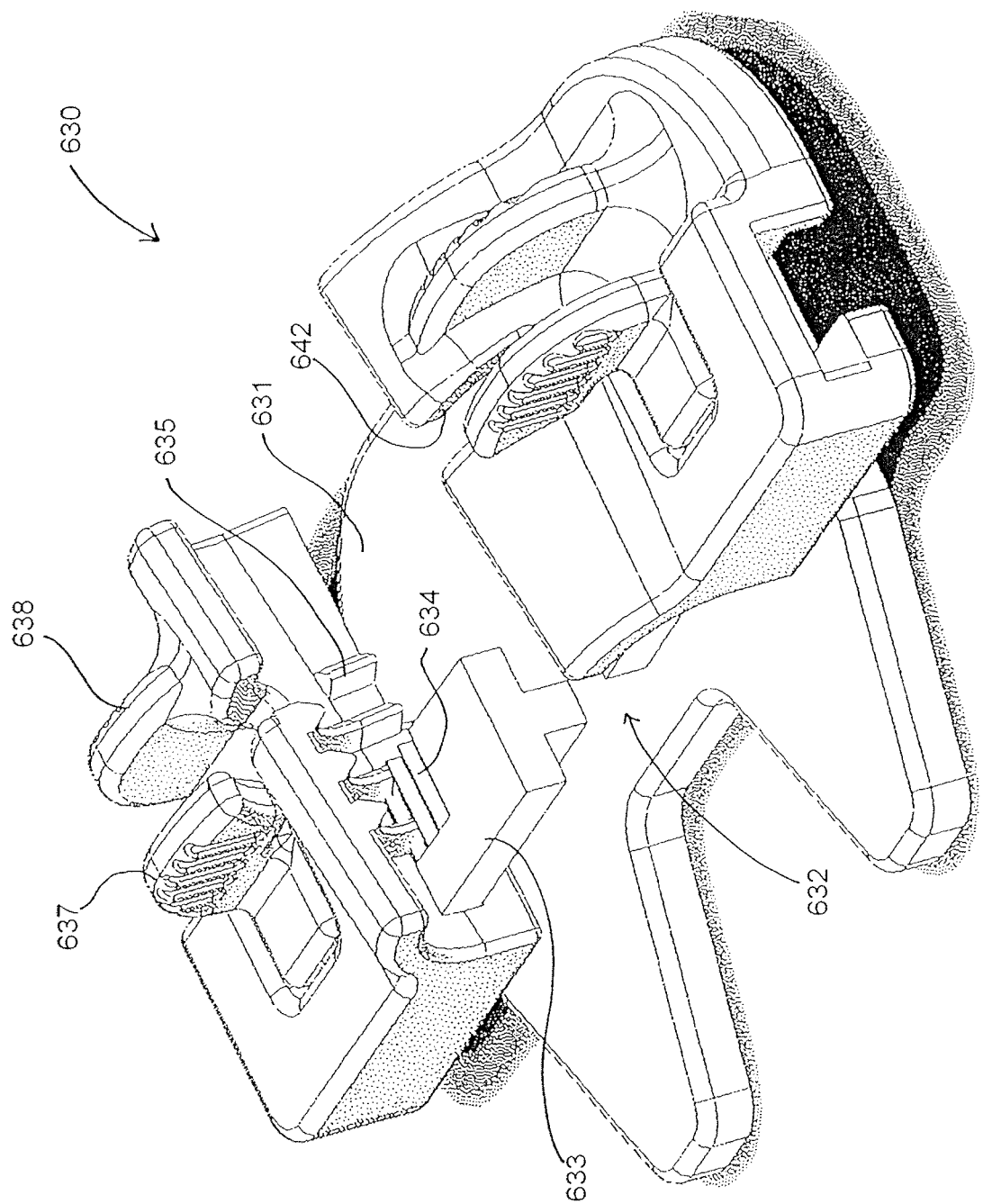
FIG. 65 is a top and front perspective view of another embodiment of a securing device.
Figure 66:
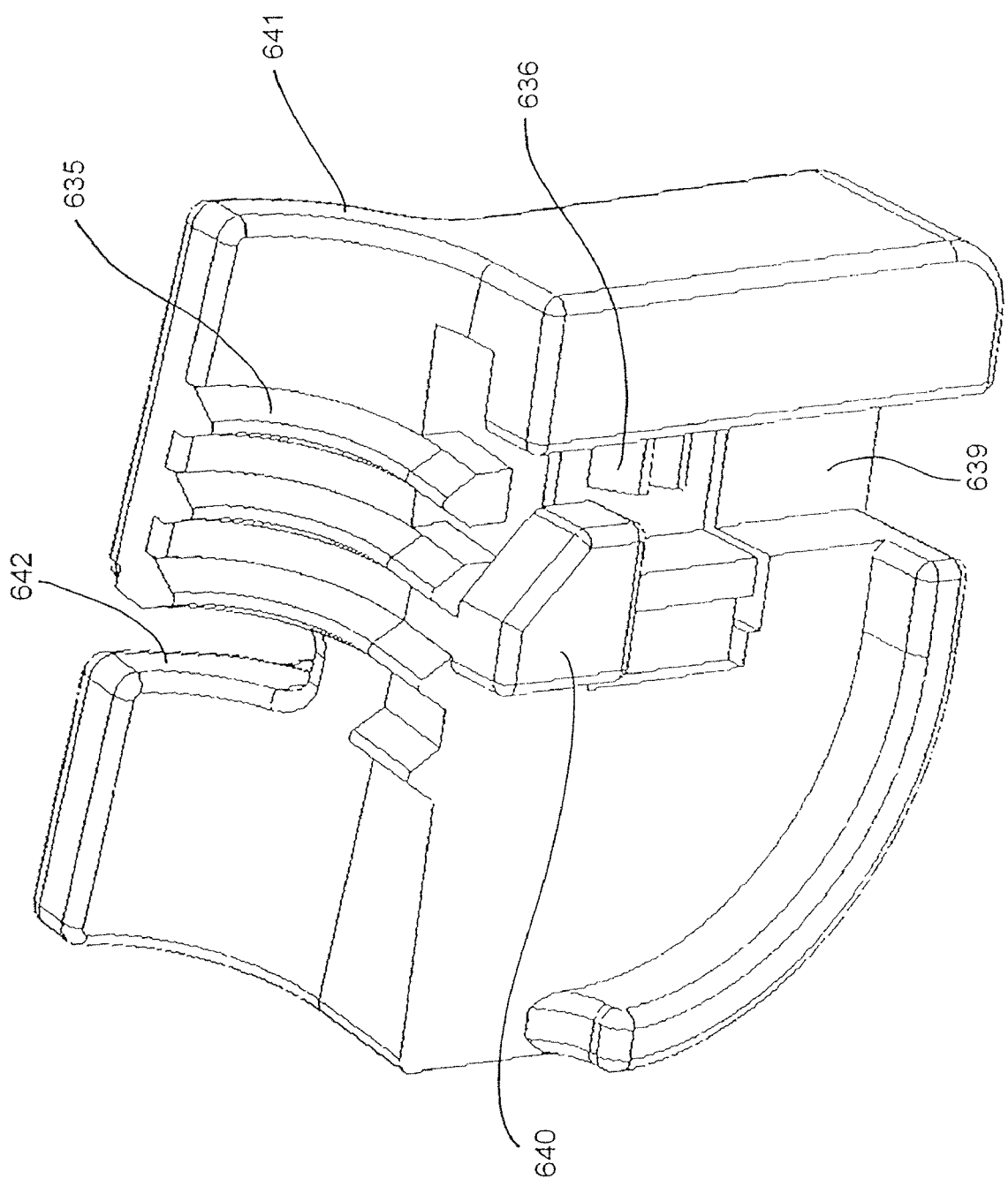
FIG. 66 is a view of the underside of a clamp of the device shown in FIG. 65.
Figure 67:
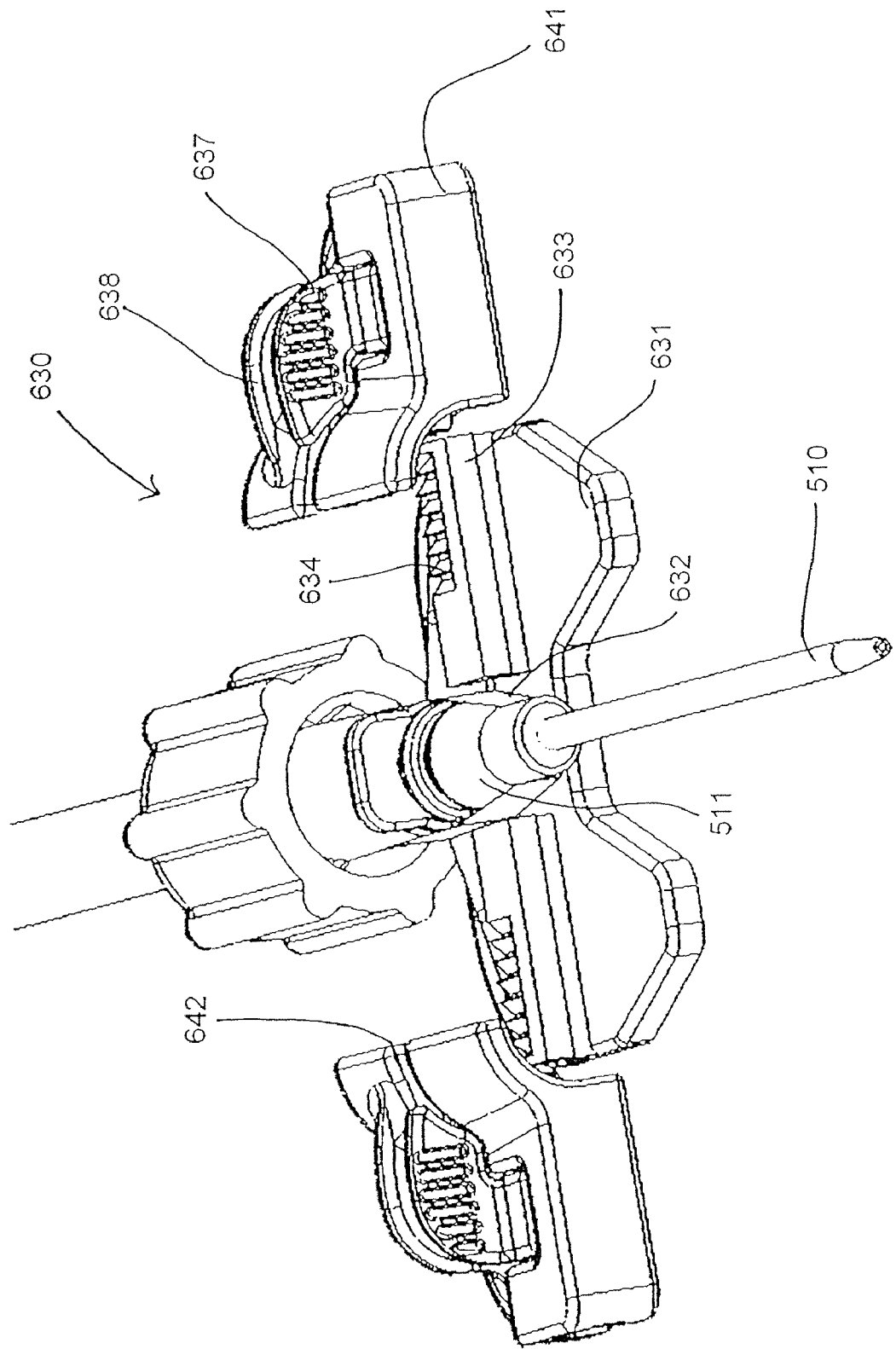
FIG. 67 is a top and front perspective view of the securing device shown in FIG. 65 with a catheter in place.

In another embodiment, as shown in FIGS. 65-67, a securing device 630 includes a base 631. Extending up from the base are one or more tracks 633 which run parallel to the lateral X axis. The tracks 633 are separated by a receiving area 632 for receiving catheters and catheter fittings of various shapes or sizes. One or more movable or slidable clamps 641 are connectable to the tracks 633. The top surface of the tracks 633 include ribs 634. The underside of the clamps 641 include one or more teeth 636 positioned within a recessed indent 639. The indent 639 runs along the lateral X axis and is configured to receive a track 633. The clamps 641 may be attached to the tracks 633 by inserting a track 633 into the indent 639 of the clamp 641, thereby allowing the teeth 636 to engage the ribs 634.

The top surface of the clamp 641 includes a fixed tab 638 and a push tab 637. The push tab 637 in connected to a retention wedge 640 which extends from the underside of the clamp 641 and is spring loaded or flexible or resilient such that it is forced or pressed against the track 633, allowing the clamp 641 to be held in a fixed position. The push tab 637 may be pushed toward the fixed tab 638 in the longitudinal direction, which causes the retention wedge 640 to flex away from the track 633, at which time the clamp 641 may be moved or slid along the lateral X axis either away from or toward a catheter fitting positioned within the receiving area 632. The ribs 634 and teeth 636 interact with each other to create a ratchet like mechanism, which provides different settings for positioning, locking, or holding the clamps 641 in relation to each other. The clamps may be adjusted or restricted to each rib 634 or notch on the track 633 to accommodate catheter fittings of different shapes or sizes.

In operation, one or more clamps 641 are pushed or slid toward each other along the tracks 633 toward a catheter fitting to clamp or hold the catheter fitting in place. The retention wedge 640 or ratchet mechanism of the ribs 634 and teeth 636 may hold or lock the clamps 641 in place and restrict further movement unless desired. In the closed position, contact bars 635 apply pressure to the catheter or catheter fitting, e.g., catheter hub, to securely hold the catheter or catheter fitting in place and prevent movement in various dimensions or directions. Likewise, one or more clamps 641 may be moved or slid along the tracks 633 away from each other in order to release the restrained catheter fitting. Also, the clamps 641 include slits 642 for receiving tabs or other extensions on a catheter hub or catheter fitting when the clamps 641 are in the closed position to prevent longitudinal, lateral, or other types of movement. Further, flanges or wings on a catheter fitting positioned within the receiving area 632 may abut against the tracks 633 to further prevent movement of the catheter or fitting in the longitudinal direction. In any of the above embodiments, the base may be generally V-shaped, see e.g., FIG. 65, in order to position the hub or catheter fitting in close proximity to the patient to facilitate ease or convenience of use.

Figure 68:
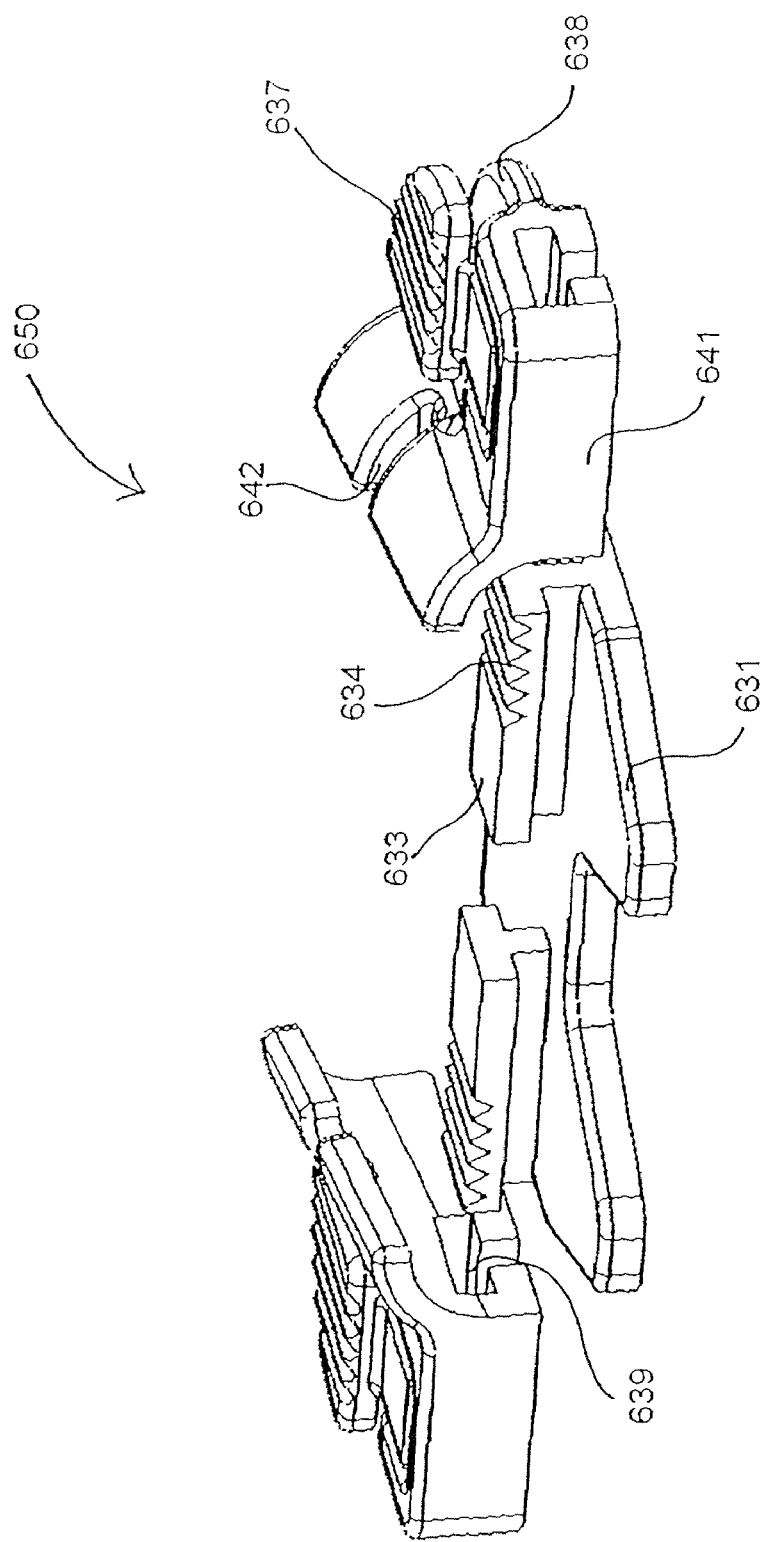
FIG. 68 is a top and front perspective view of another embodiment of a securing device.

In FIG. 68, another variation of the embodiments in FIGS. 65-67 is shown. Here, the securing device 630 operates in a similar manner as described above, however the design of the securing device is varied. The push tab 637 and fixed tab 638 are oriented in planes that run substantially parallel to the plane of the base 631, rather than in planes that are substantially perpendicular to the base. This provides a securing device with a lower overall profile. The push tab 637 operates by being pushed against the fixed tab 638 in order to flex the retention wedge or teeth on the underside of the clamps away from the track and ribs, thereby allowing the clamps to be slid or ratcheted along the tracks into an opened or closed position.

Figure 69:
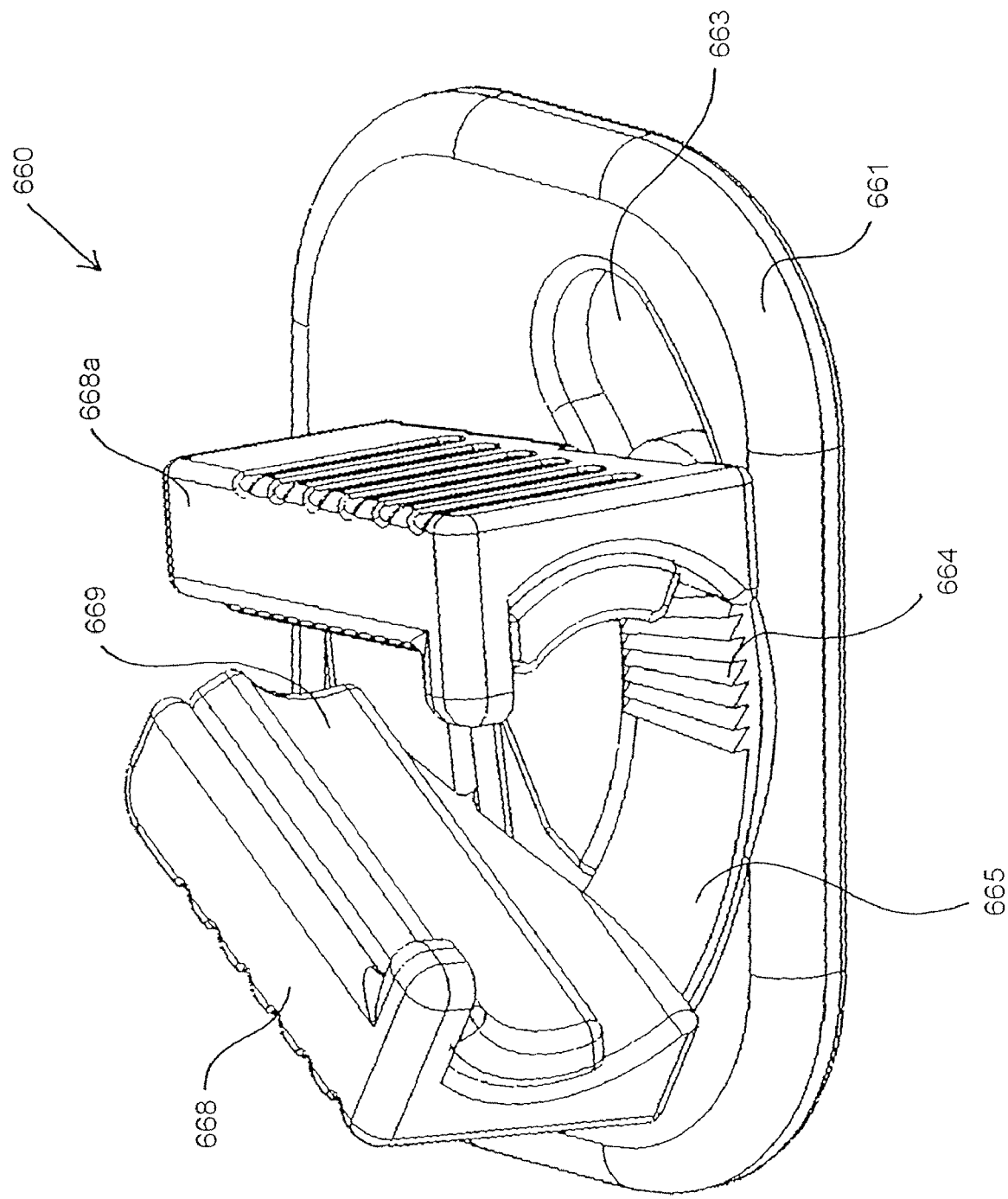
FIG. 69 is a perspective view of another embodiment of a securing device.
Figure 70:
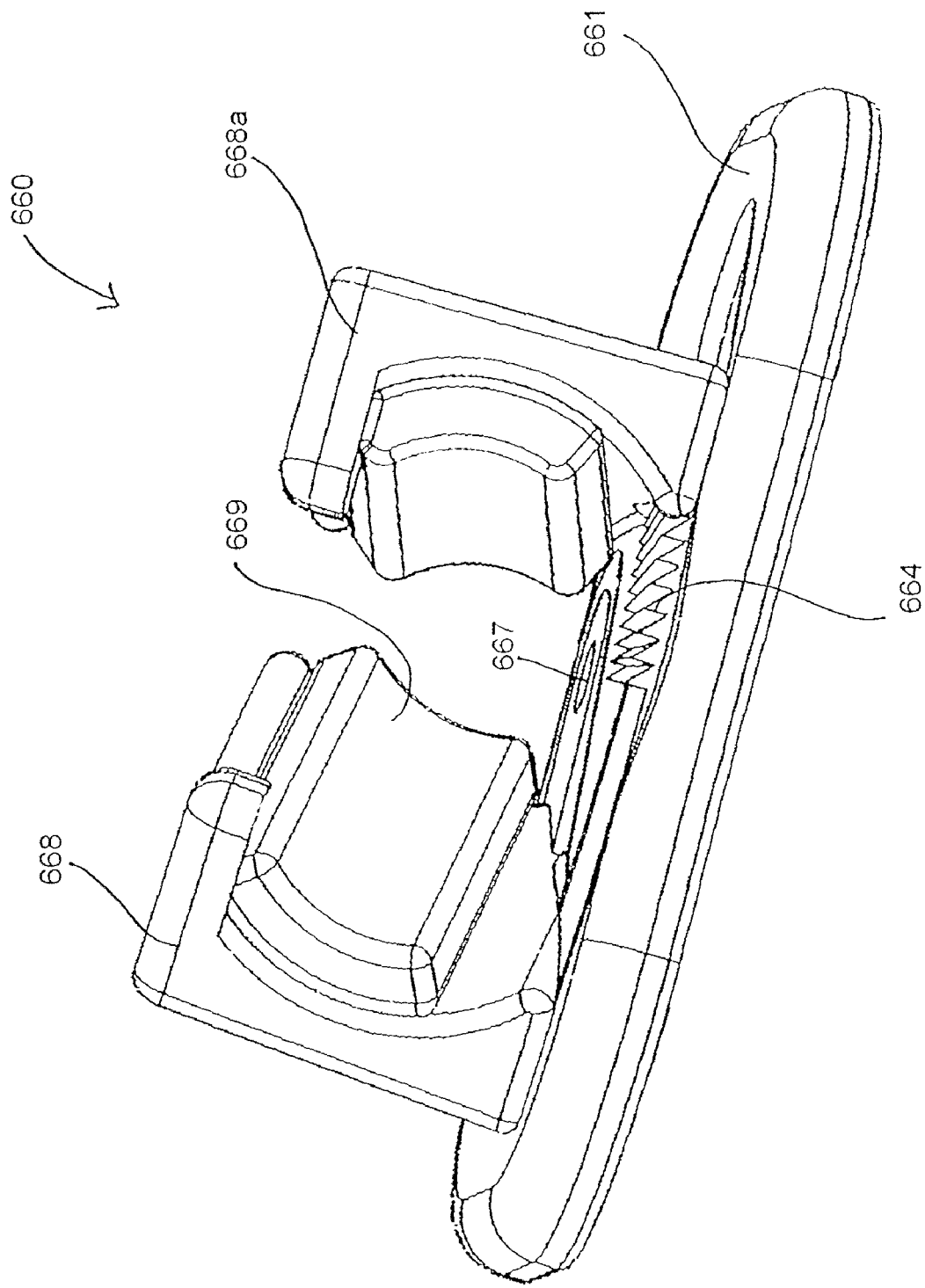
FIG. 70 is a perspective view of the base shown in FIG. 69.

In another embodiment, as shown in FIGS. 69 and 70, a securing device 660 includes a base 661. The base includes a track 663. Positioned on the base 661 are one or more clamps. One or more of the clamps may be movable. In one embodiment, there is a movable clamp 668 and a fixed clamp 668a. Extending from the movable clamp 668 in a direction toward the fixed clamp 668a is a ratchet arm 665, which is positioned within the track 663 The end of the ratchet arm 665 may have ribs 664 on its upper surface. Restraining walls 669 are positioned on the inner surface of the clamps to grip or hold catheters or catheter fittings of various sizes in place.

In operation, the movable clamp 668 is pushed toward the fixed clamp 668a such that it rotates about a pin 667 or other suitable rotational or hinge mechanism. As the clamp 668 is pushed, the ribs 664 on the ratchet arm 665 engage teeth or corresponding ribs on the underside of the fixed clamp 668a. The ratchet arm and clamp move within the track by being slid or ratcheted toward the fixed clamp 668a. The clamps, in a closed position, hold a catheter fitting positioned on the base 661 thereby securing it in place. The ratchet mechanism may hold or lock the movable clamp 668 in place at different intervals or notches to accommodate catheters or catheter fittings of various shapes or sizes.

The catheter or catheter fittings are held in place by the restraining walls 669 on the inner surface of the clamps. The restraining walls 669 may be made of foam or other moldable material which conforms to the shape of the catheter fitting to hold it in place. Teeth, spikes, any type of capture element, or any material suitable to hold catheter fittings may also extend from or line the restraining walls 669 or inner surface of the clamps to hold or grip various catheter fittings. To release the clamps from a catheter fitting, the end of the ratchet arm 665 can be pressed down toward the base, thereby disengaging the ribs 664 to teeth connection and allowing the movable clamp 668 to slide away from the fixed clamp 668a.

Figure 71:
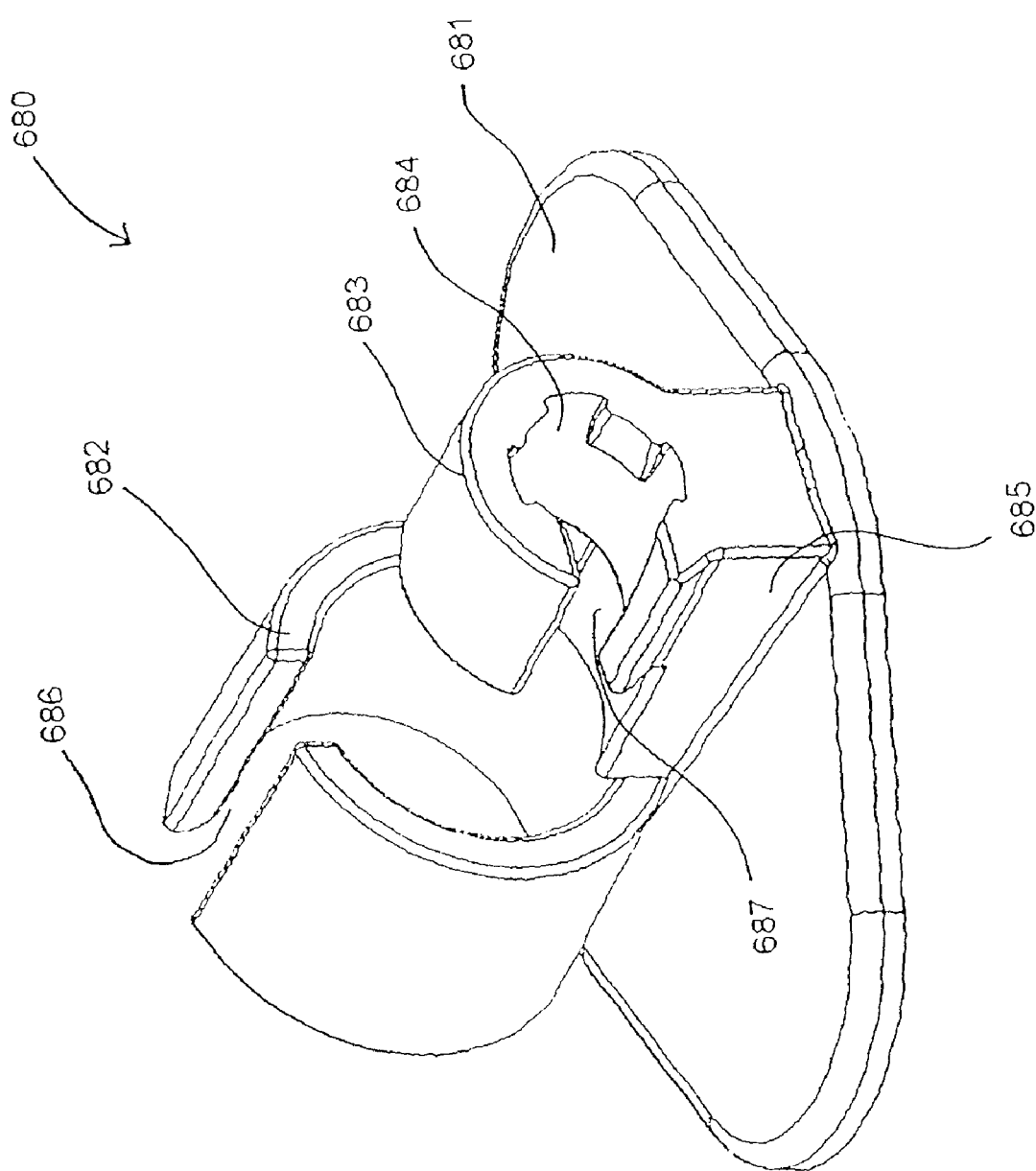
FIG. 71 is the top and front perspective view of another embodiment of a securing device.
Figure 72:
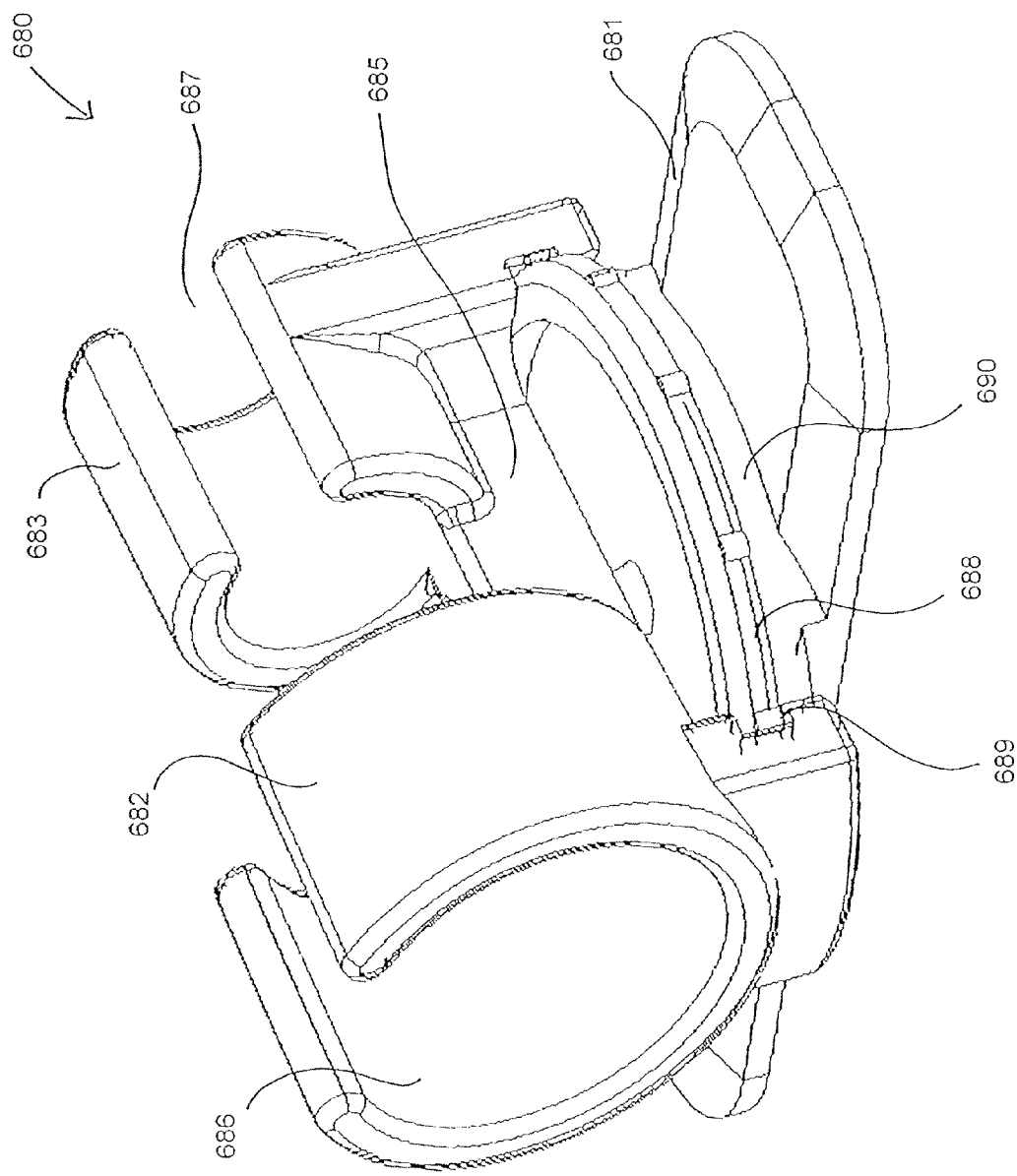
FIG. 72 is a rotatable version of a securing device.

In another embodiment, as shown in FIGS. 71 and 72, a securing device 680 for securing various IV luer locks, J-loop locks, luer locks, and other catheter fittings includes a base 681. Positioned on the top surface of the base 681 is a first receiving area 682 having a substantially cylindrical shape with an opening 686. Adjacent to the first receiving area 682 is a platform 685 with a second substantially smaller receiving area 683 extending from the platform 685. The second receiving area 683 is also substantially cylindrical in shape with an opening 687. The second receiving area 683 may include grooves 684 which are configured to receive or grip a luer lock or other fitting attached to an IV catheter hub or other catheter or catheter fitting when the catheter hub is placed within the first and second receiving areas and securely held in place to restrict substantial movement of the catheter. Optionally, as shown in FIG. 72, swivel arms 689 may extend from both the first and second receiving areas 682, 683. The swivel arms 689 attach to a ridge 688 along the top of a trunk 690 such that the receiving areas can rotate or swivel about the ridge 688 or trunk 690.

Figure 73:
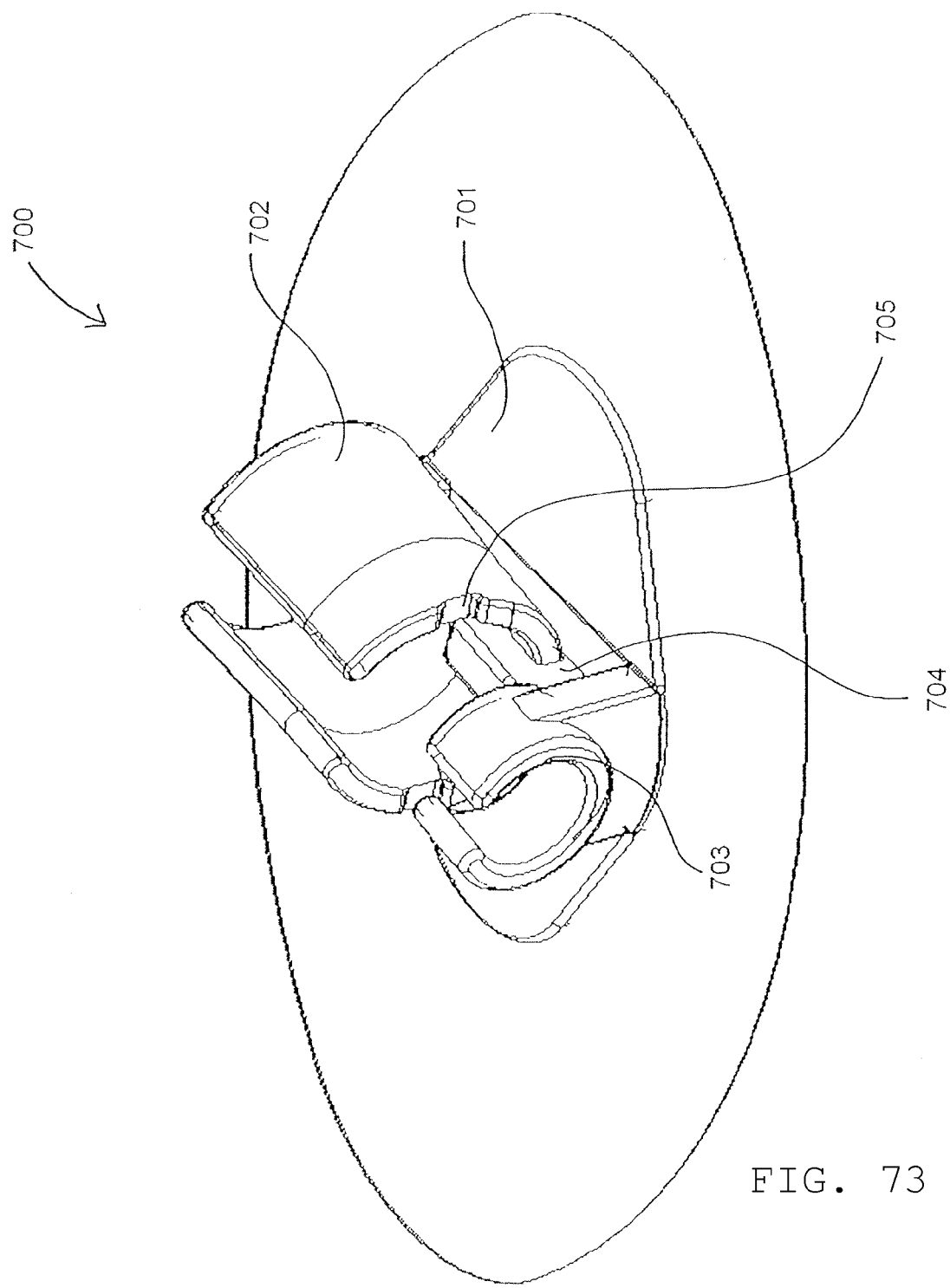
FIG. 73 is the top and front perspective view of another embodiment of a securing device attached to an adhesive pad.
Figure 74:
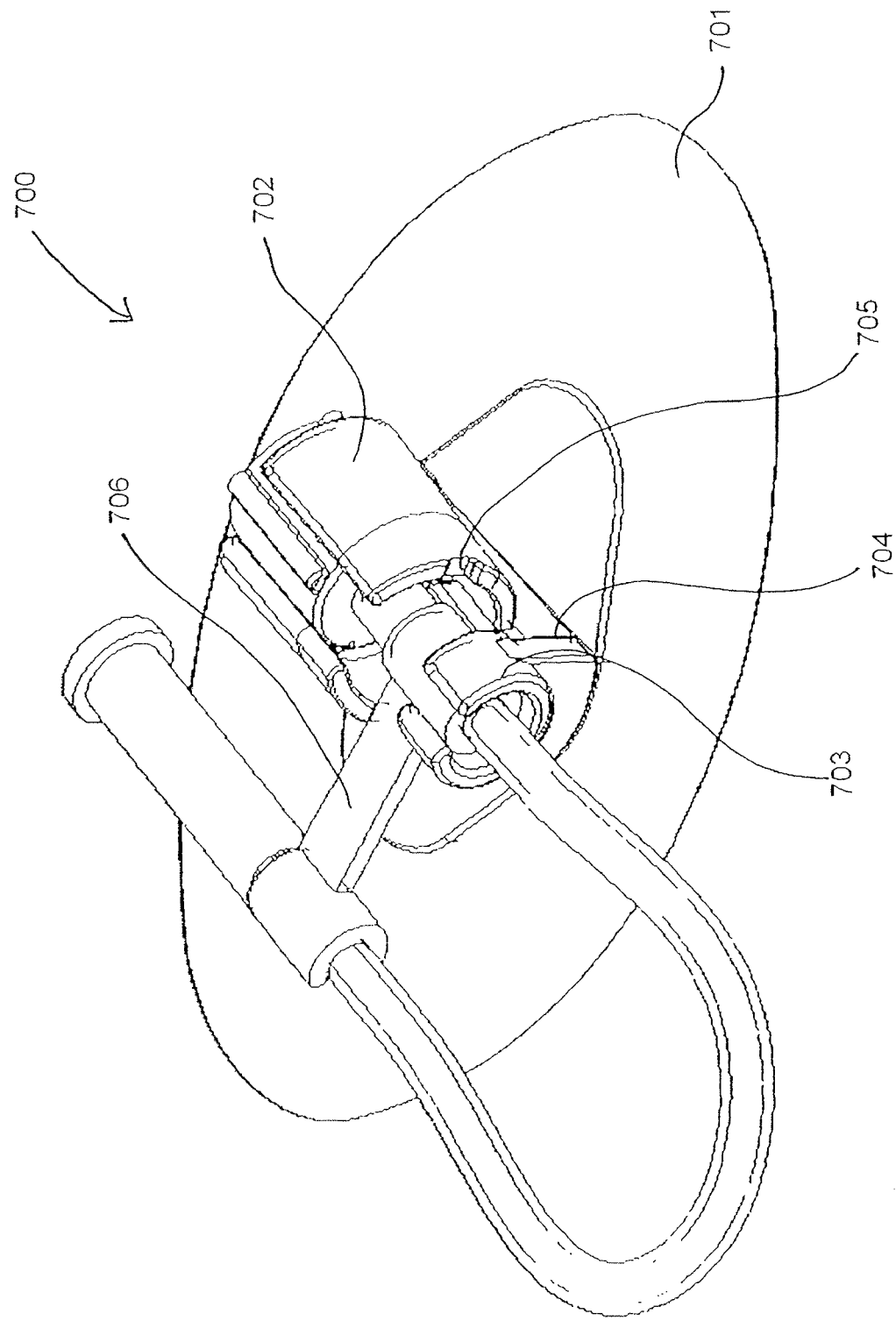
FIG. 74 is the top and front perspective view of the securing device shown in FIG. 73 with a J-loop shown.

In another embodiment, as shown in FIGS. 73 and 74, a securing device 700 includes a base 701 and two receiving areas 702, 703 having substantially cylindrical shapes which extend from a platform 704. The securing device 700 is suitable to hold or restrain a J-loop lock, luer lock, or other catheter fitting. For example, a J-loop lock or other catheter fitting may be positioned within the receiving areas 702, 703, and rest on the top surface of the platform 704. An arm 706 of a J-loop lock may extend through the space between the two receiving areas and be held or locked in place within a groove 705 to prevent movement of the J-loop lock. The arm 706 may be held by a groove 705 positioned anywhere on the end of the receiving area 702 such that the J-loop lock can be positioned at different angles.

Figure 75:
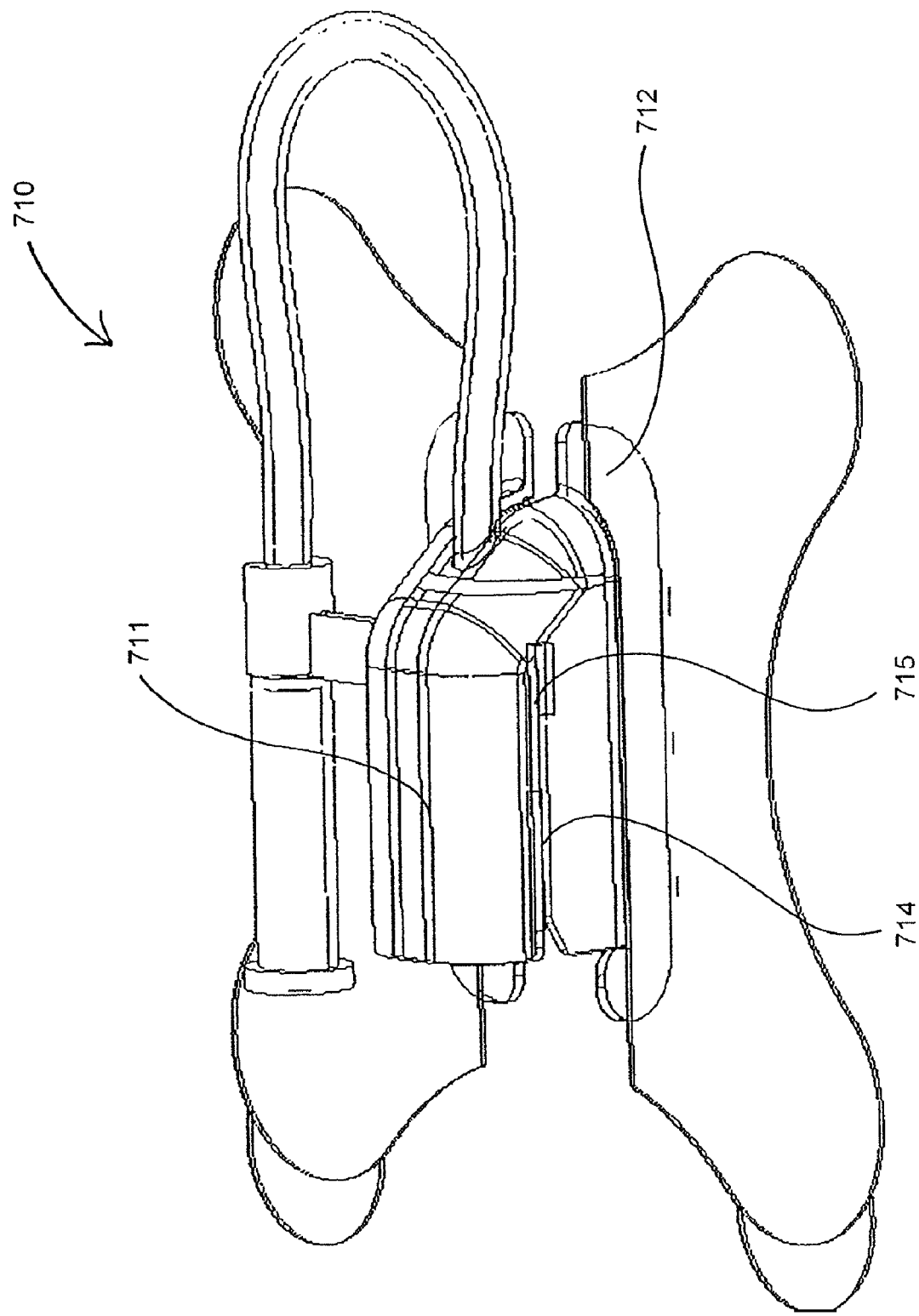
FIG. 75 is the top and side perspective view of another embodiment of a securing device with a J-loop shown.
Figure 76:
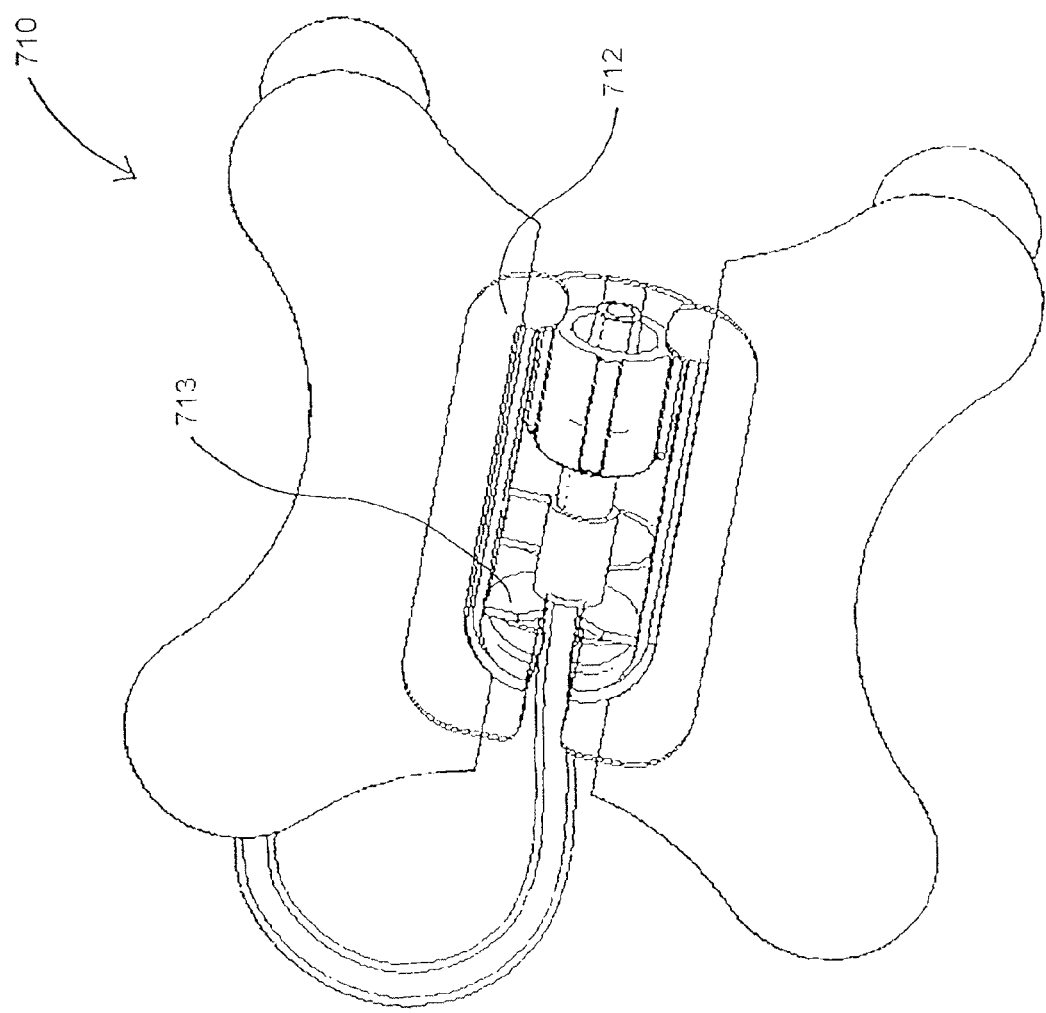
FIG. 76 is a bottom view of the securing device shown in FIG. 75.
Figure 77:
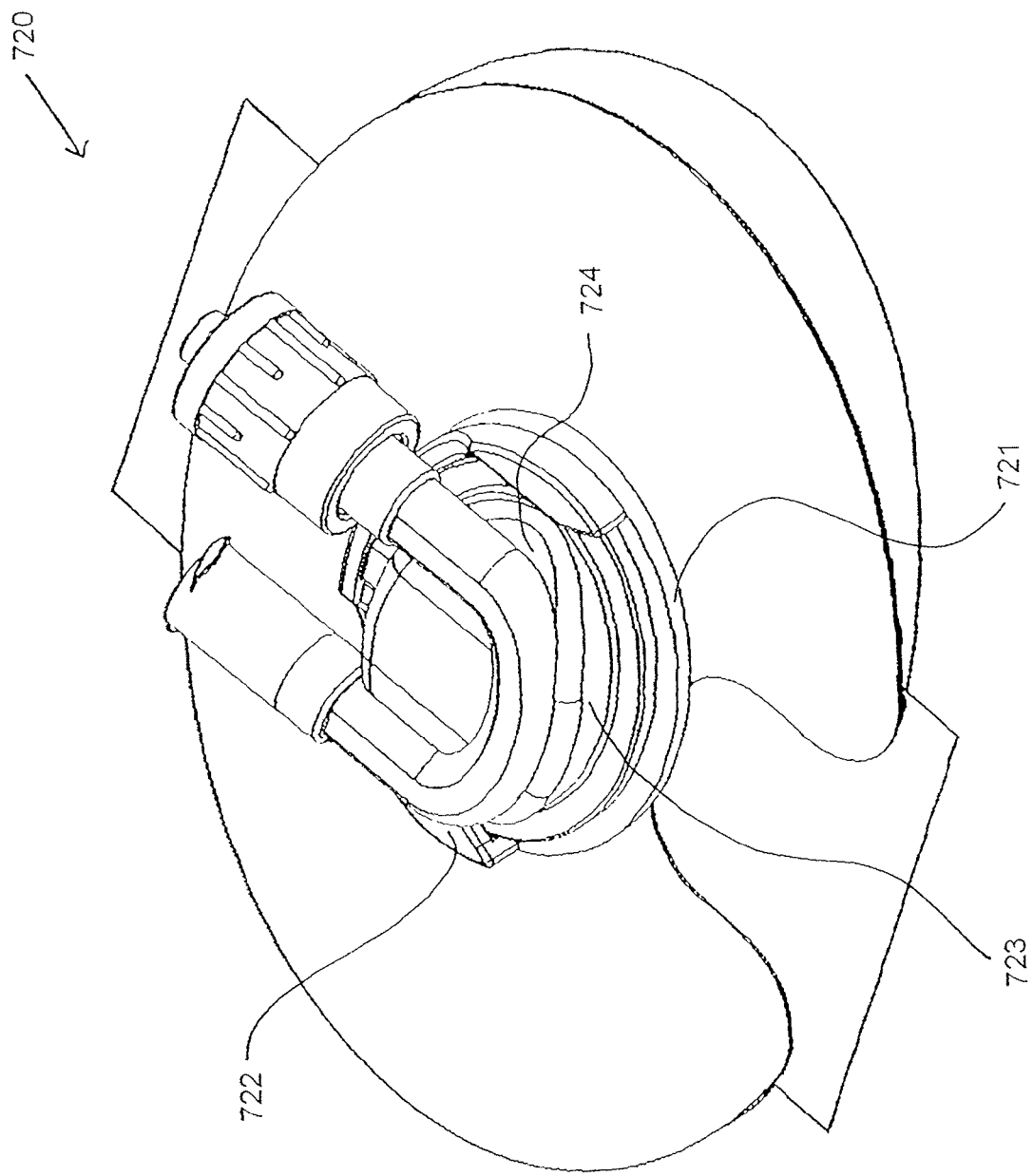
FIG. 77 is a top and front perspective view of a securing device with a slidable receiving plate on the base.

Additional embodiments for securing a J-loop lock, luer lock, or other catheter fitting are shown in FIGS. 75-77. FIGS. 75 and 76 show a securing device 710 with a base 712 and a dome 711 extending up from the base. A J-loop lock can be positioned within the dome 711 such that an arm of the J-loop lock is slid into the side slit 714 and into the groove 715 to be held or locked into place. A plate 713 (shown in FIG. 76) within the dome 711 also serves to restrain a J-loop lock or other catheter fitting positioned in the dome 711 as the catheter fitting abuts against the plate 713, preventing movement in the longitudinal direction and locking or holding the catheter fitting in place against the plate 713. The dome 711 has an opening on either end to allow for passage of the catheter. FIG. 77 shows a securing device 720 which includes a base 721 and a slidable receiving plate 723 for holding or restraining a J-loop or other catheter fitting. The J-loop, for example, one made of injection molded hard plastic, can be attached to the retention groove 724 in the receiving plate 723 and the receiving plate 723 may be slid onto the base 721 and locked or held to the base 721 by the flex locks 722.

Figure 78:
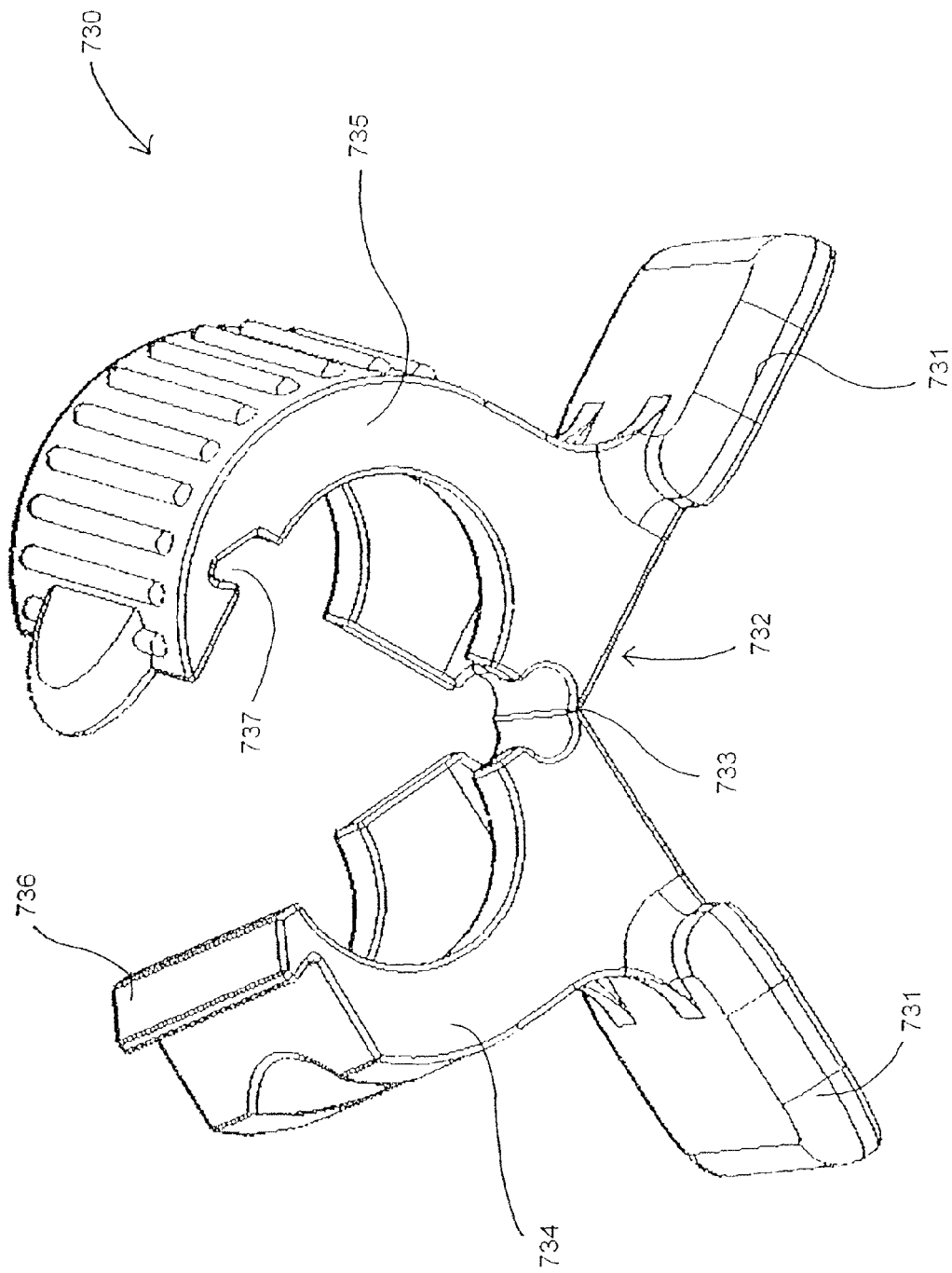
FIG. 78 is a perspective view of another embodiment of a securing device.

Another embodiment for securing catheter fittings such as IV catheter hubs of various shapes or sizes is shown in FIG. 78. The securing device 730 includes a ring clasp 732 and base flanges 731 extending form the ring clasp 732. The ring clasp 732 is made of two halves which can pivot open and closed about a center joint 733. A first half 734 of the ring clasp 732 has a ridge 736 which engages a locking area 737 on the second half 735 of the ring clasp 732. This locking mechanism serves to hold the ring clasp 732 in the closed position when a catheter or catheter fitting is positioned therein, in order to prevent movement of the catheter or securely hold it in place. Optionally, the locking mechanism may operate by snapping a resilient or flexible ridge 736 into the locking area 737.

Furthermore, any of the securing devices may be attached to a patient in a variety of ways. For example, an adhesive pad, as described in the above embodiments or an adhesive tape may be used for attaching the securing device to a patient. For example, an adhesive pad may optionally be attached to a base or to a support plate. Optionally, any other suitable attaching method or structure may be used.

Figure 17:
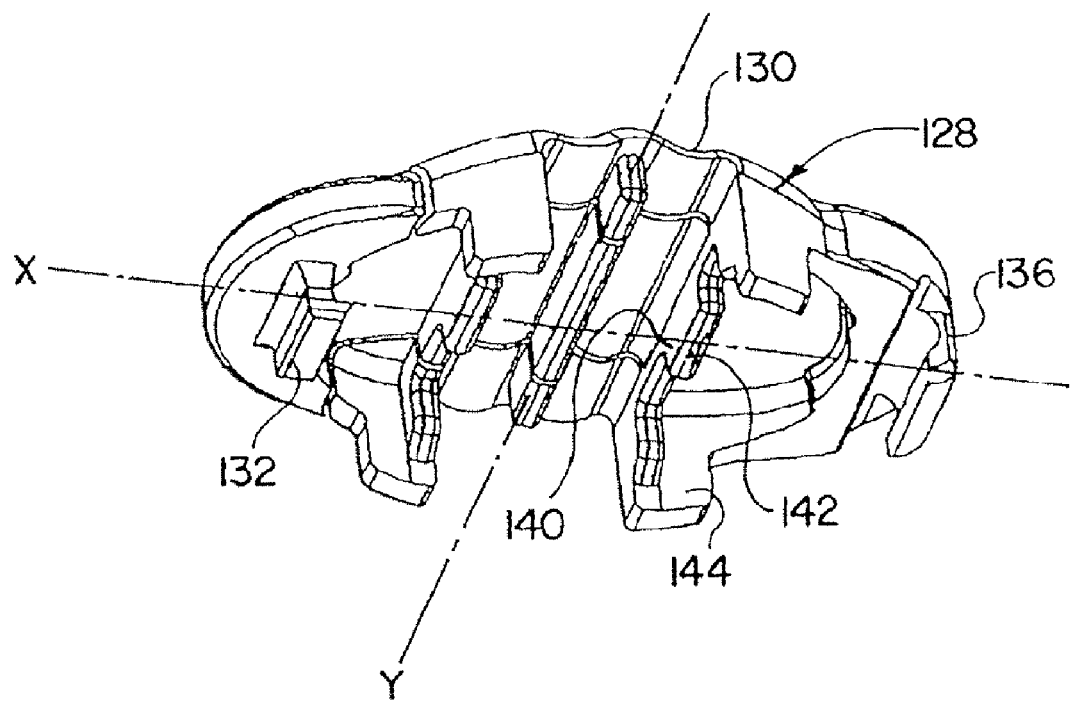
FIG. 17 is a perspective view of the under side of the cover shown in FIG. 16.

Another embodiment of a securing device 124 is shown in FIGS. 16-20. As best shown in FIG. 17, grooves 130 are provided on cover 128 which help make the cover more flexible. A latch 132 and snap hinge 136 are centered at opposite sides of the cover 128, along the lateral X axis of the cover 128. Web sections 140 run generally parallel to a longitudinal Y axis between column legs 144 and between grooves 130 on the under side of the cover 128. The web sections 140 include a capture element 142 and elevated ends 145 extending from the web sections 140.

As shown in FIG. 19, the device 124 may also include a base 126. The locating elements 150 on the base 126 include a front pair 152 and a back pair 154 of locating elements arranged in a front to back direction as indicated by arrow 49. In general, the locating elements 150 may be substantially symmetrical side-to-side about the longitudinal axis or centerline Y. The locating elements 150 help restrain a catheter and catheter fitting of various shapes and sizes and help prevent substantial side-to-side, back-to-front, axial and rotational movement of such catheters and catheter fittings on the base 126. At the foot of a locating element 150 is a ridge 155 and positioned in between the front pair 152 and back pair 154 of locating elements is a bar 157 running on either side of the arrow 49 and generally parallel to arrow 49. A bottom latch 159 and snap hinge base 158 are centered at opposite sides of the base 126, along the lateral X axis of the base 126. Side walls 156 may extend up form the base along the perimeter of the base 126.

In one embodiment the locating elements 150 are arranged such that a front locating element 152 is separated from a back locating element 154 by a dimension EE which extends from the inner tip of 152 straight back and perpendicular to 154. Also, the inner edge of the first or right back locating element 154 may be separated from the inner edge of the second or left back locating element 154 by a dimension GG running generally parallel to a lateral axis X. Also, the inner edge of the first or right front locating element 152 may be separated from the inner edge of the second or left front locating element 152 by a dimension HH running parallel to dimension GG. In one embodiment, dimension GG may be greater than dimension HH. In another embodiment dimension GG may be about 130 to 170% of dimension HH or more preferably about 140 to 160% of dimension HH.

Figure 20:
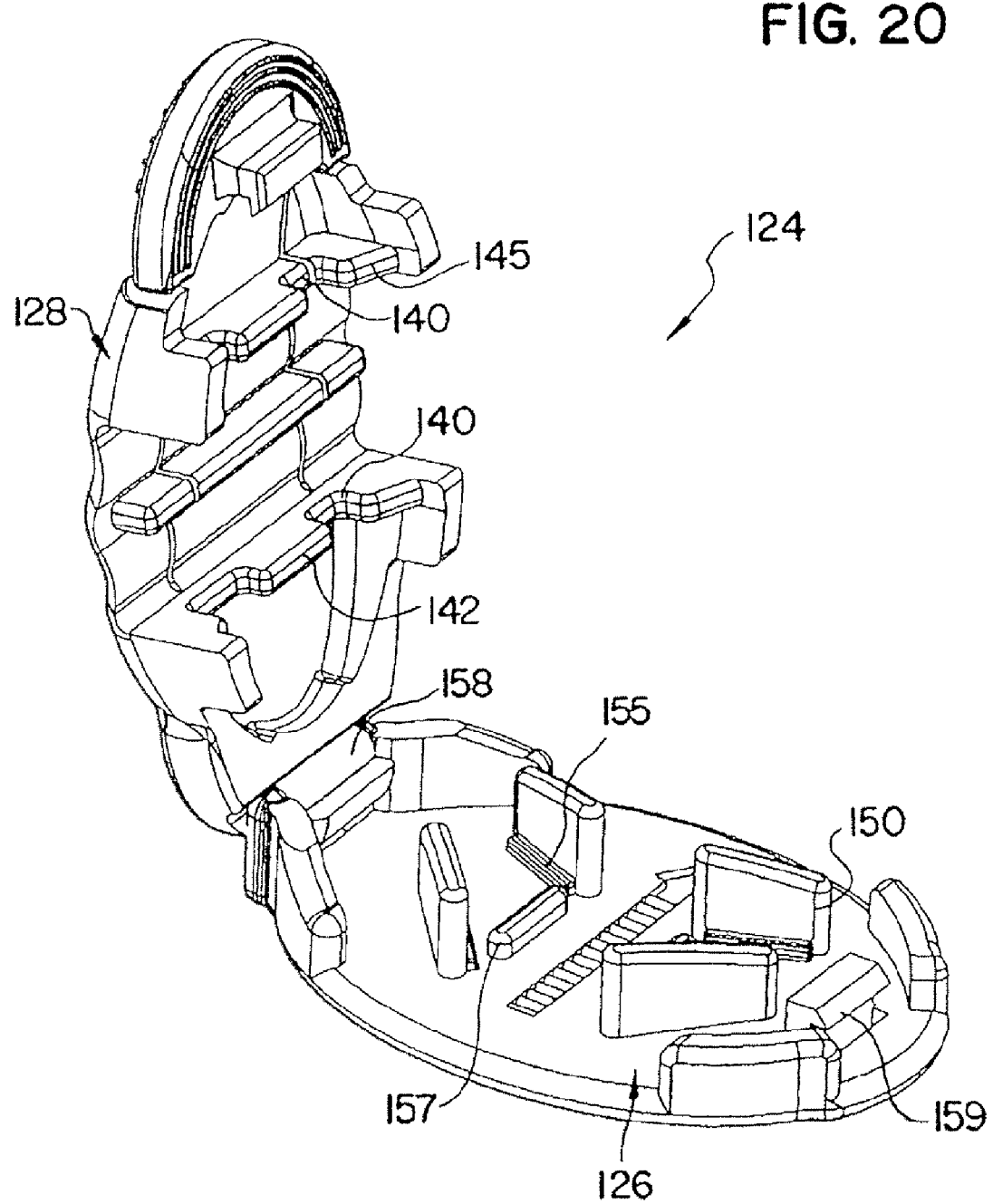
FIG. 20 is a top and front perspective view of the cover and base shown in FIGS. 16-19 fastened together to form a securing device.

As shown in FIG. 20, the device 124 operates such that the cover 128 is attached by the snap hinge 136 to the snap hinge base 158 of base 126 and the cover 128 can rotate down onto the base 126 into a closed position where the latch 132 and bottom latch 159 engage. In a closed position the capture element 142 on the web sections 140 is adapted to contact and compress the top of a catheter fitting held within device 124. The capture elements 142 help compress and grip catheter fittings of various shapes and sizes (e.g., by compressing the body and/or wings of a catheter fitting) securely holding the catheter fitting in place and preventing substantial movement of the catheter fitting such as in an axial, side-to-side, back-to-front, up and down and rotational direction. The capture elements may compress the catheter fitting against the ridge 155 and/or bar 157. The ends 145 of the web sections 140 serve a similar function as the locating elements discussed above as they also help restrain a catheter fitting and help prevent substantial side-to-side, back-to-front, axial and rotational movement of the catheter fitting. The web sections 140 including capture elements 142 and ends 145, as well as bars 157 and ridges 155, may be solid or spring molded and may be made of various materials as discussed above. Optionally, a base with no locating elements may be used with the cover 128 for compressing and holding a catheter.

Figure 21:
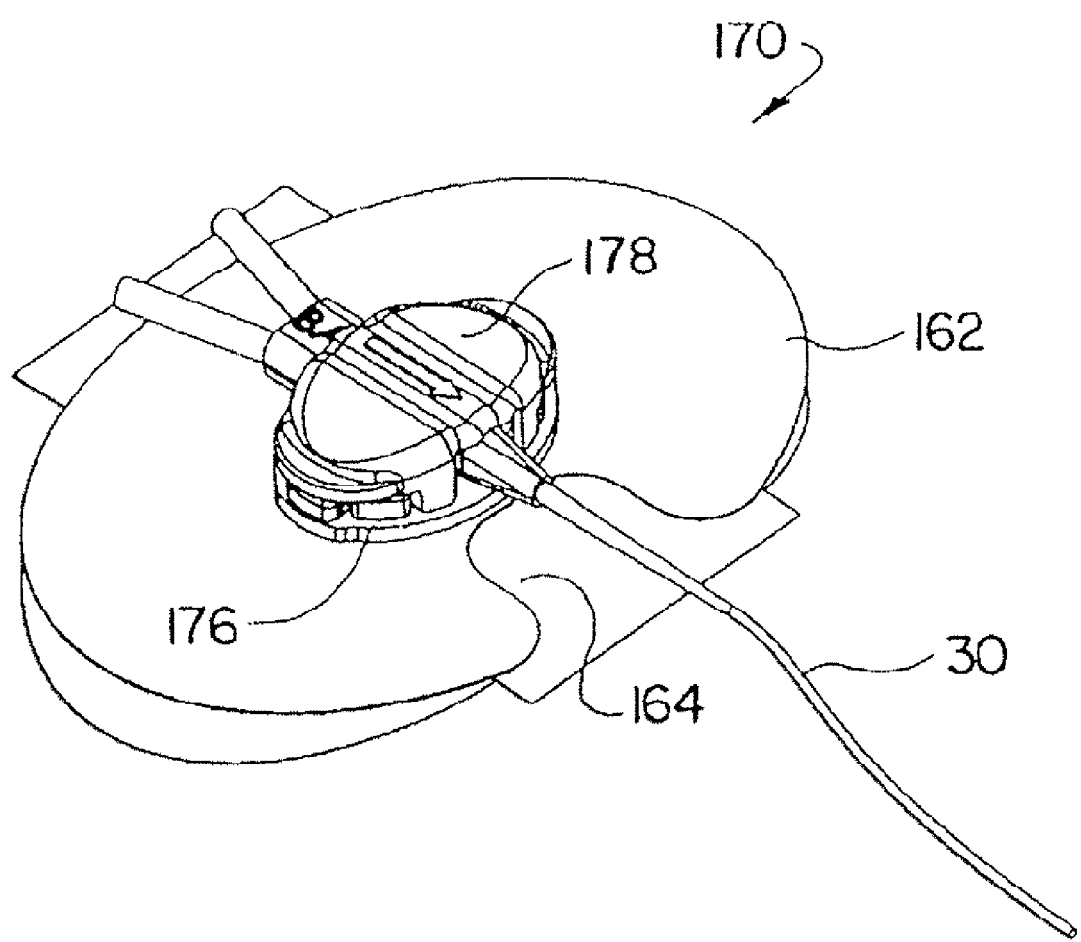
FIG. 21 is a top and front perspective view of a securing device attached to a pad.
Figure 22:
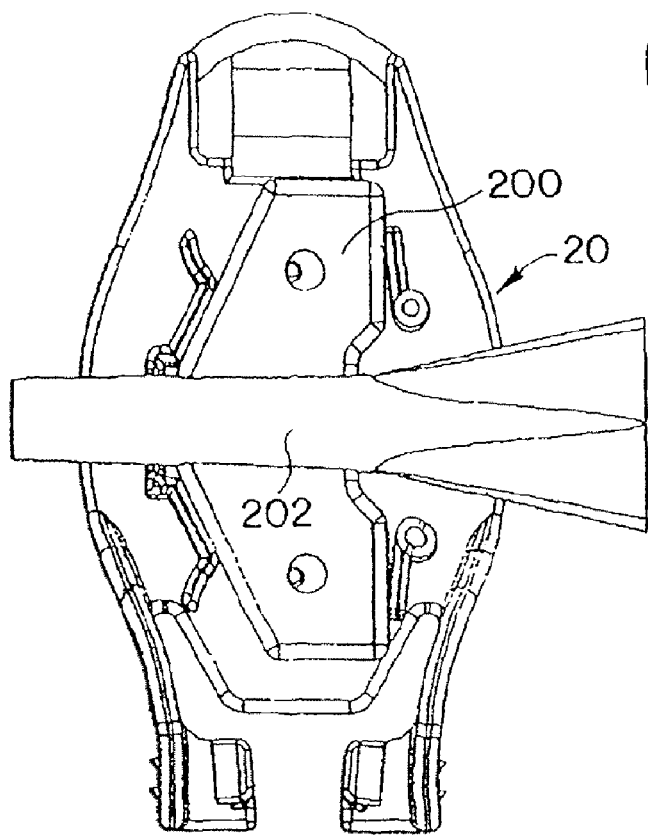
FIGS. 22-29 are plan views of various catheter fittings positioned on the base and within the locating elements of the securing devices shown in FIGS. 1-2 and 10.

FIG. 21 shows securing device 170 having a base 176 and cover 178. The device is attached to an adhesive pad 162. This embodiment operates much like the embodiments of FIGS. 16-20 described above for securing catheters and catheter fittings having various shapes and sizes. The base 176 and cover 178 may snap fit together with or without a hinge feature.

Figure 23:
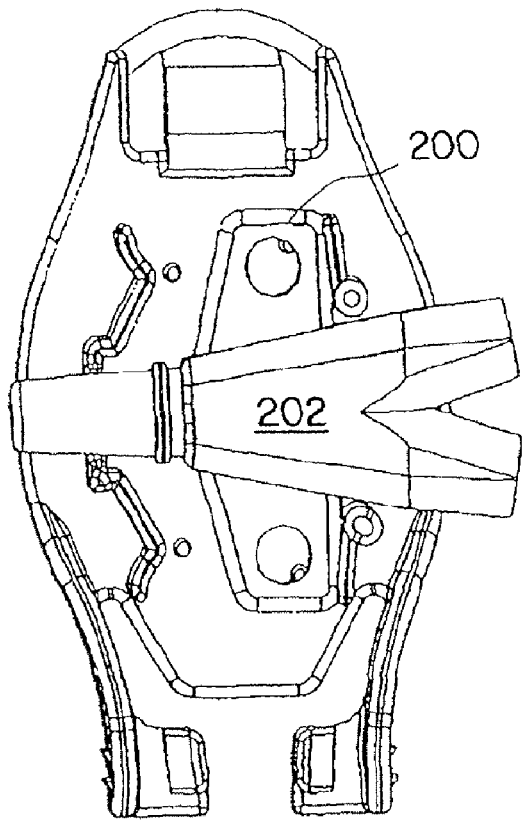
Figure 24:
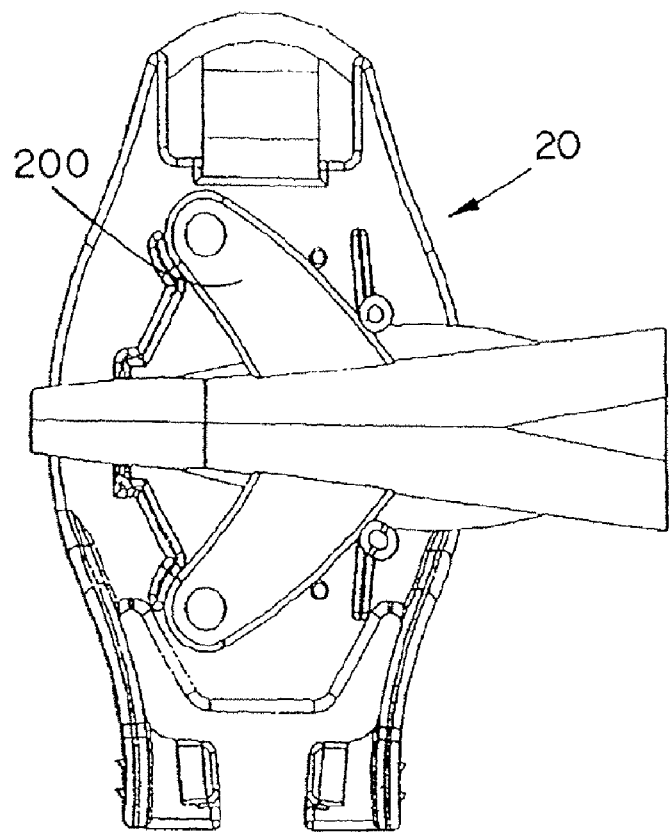
Figure 25:
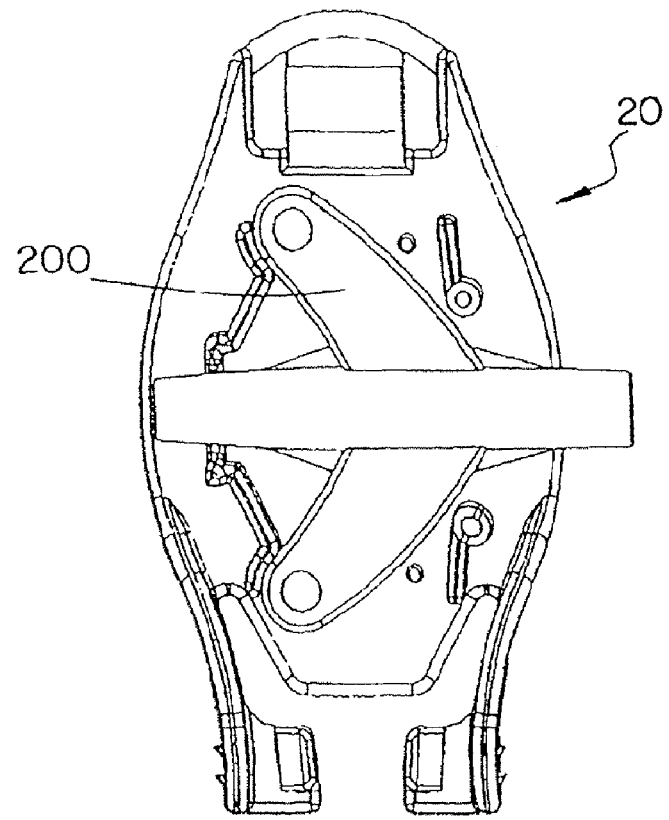
Figure 26:
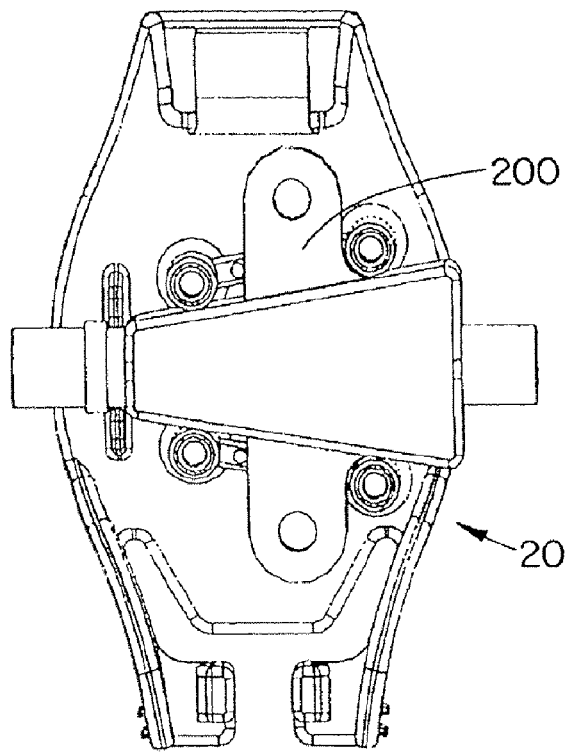
Figure 27:
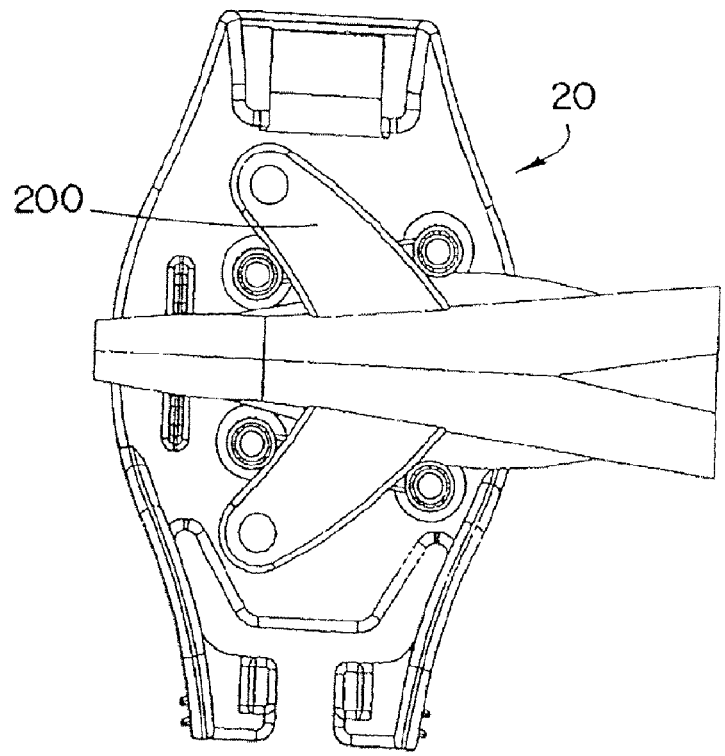
Figure 28:
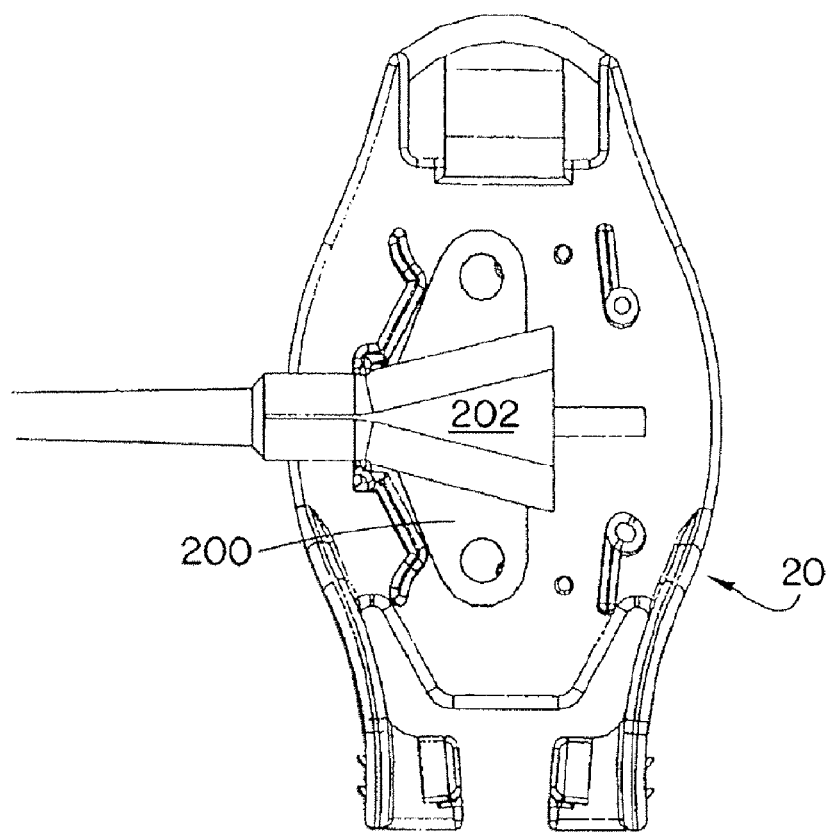
Figure 29:
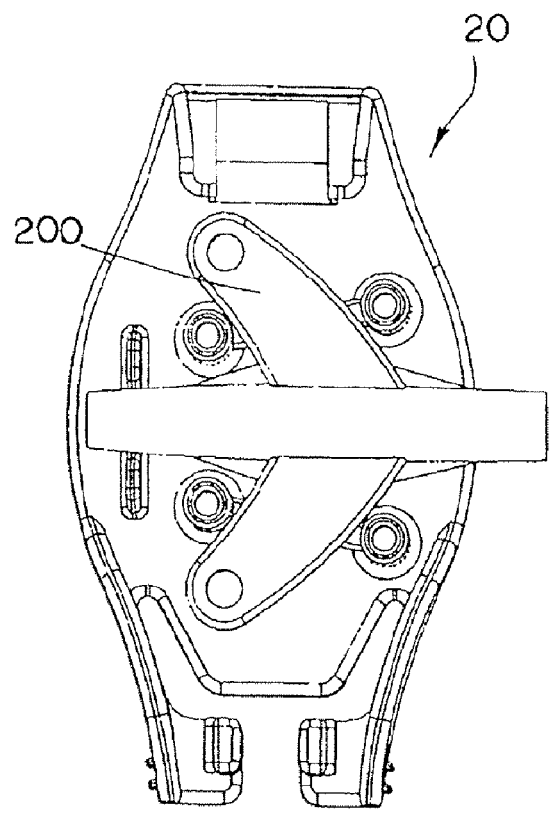

FIGS. 22-29 show the universal catheter securement device 20 in use with various different types of catheters. With some catheters, as shown in FIGS. 22, 24, 27 and 29, the wings 200 of the catheter 32 are restrained against virtually any longitudinal movement by the front and rear locating elements. With other catheters, such as shown in FIGS. 23, 26 and 28, the wings 200 of the catheter are narrower or smaller, leaving a gap between the locating elements. This would nominally allow the catheter to shift longitudinally under force (e.g., with pulling on the catheter tubes). However, when the cover is closed, the catheter body 202 and/or the wings are clamped tightly by the capture elements. This largely prevents any extensive inadvertent and undesirable movement of the catheter, even though there may be no direct physical contact with a front or rear locating element.

Figure 30:
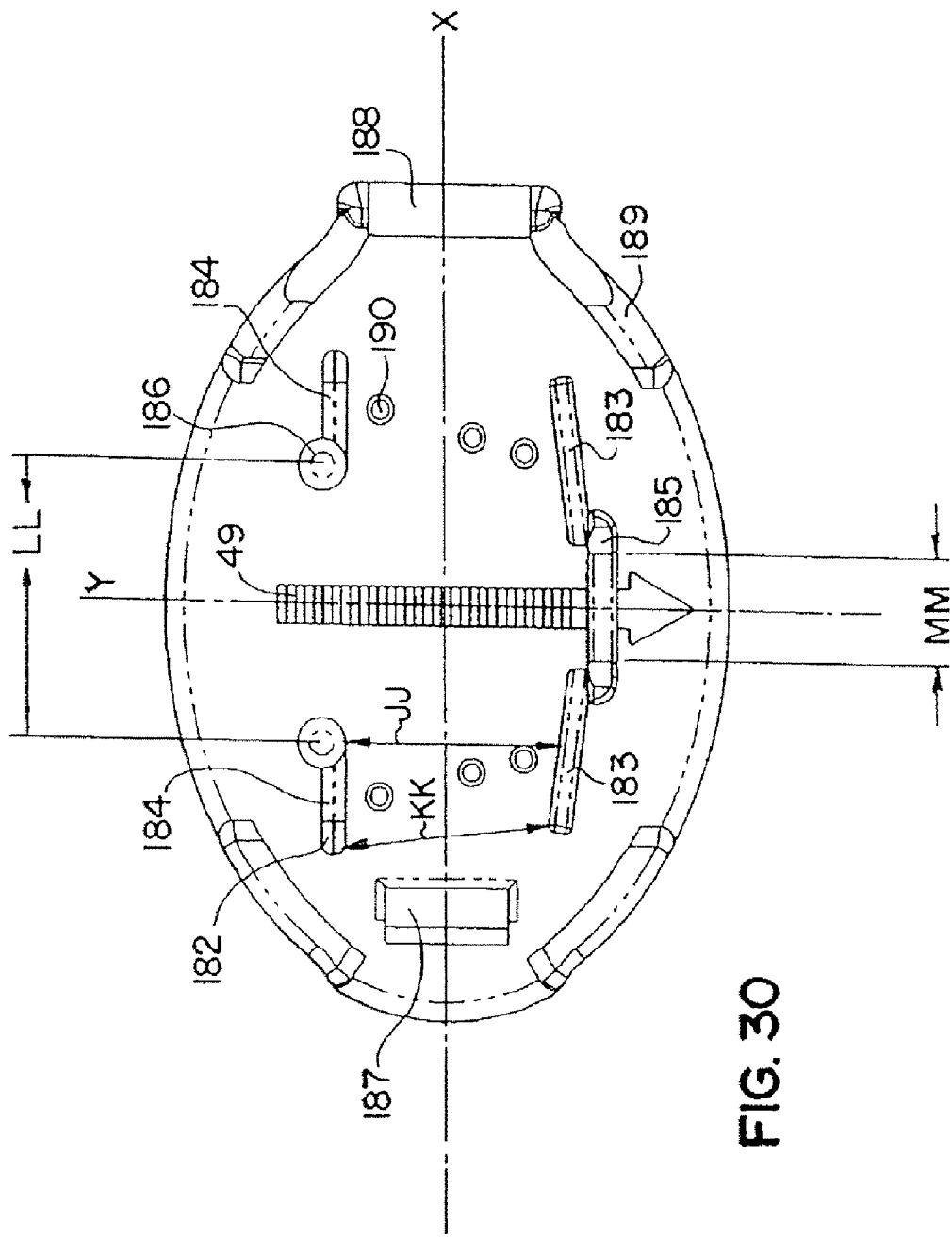
FIG. 30 is a top plan view of another base for use in a securing device.

FIG. 30 shows an alternative embodiment of a base 180 for use in a securing device. The locating elements 182 on the base 180 include at least one front wall 183 and a pair of back walls 184 arranged in a front to back direction as indicated by arrow 49. In general, the locating elements 182 may be substantially symmetrical side-to-side about the longitudinal axis or centerline Y and they are arranged to position and hold catheter and catheter fittings of various shapes and sizes to prevent substantial movement of such catheters and catheter fittings in various dimensions. The front wall 183 may be angled and a semicircular trough 185 may be positioned slightly forward of the front wall 183 and may be connected to the front wall. The back wall 184 is connected to a post 186. A bottom latch 187 and snap hinge base 188 are centered at opposite sides of the base 180, along the lateral X axis of the base 180. The base 180 may snap fit to a cover with or without a hinge feature. Side walls 189 may extend up form the base along the perimeter of the base 180 and spikes 190 may extend up from the base and run in a line on either side of arrow 49, between a front wall 183 and back wall 184. The base 180 can operate in conjunction with a cover in a manner to compress and/or restrain catheters and/or catheter fittings of various shapes and sizes and prevent their substantial movement in various dimensions.

In one embodiment the locating elements 182 are arranged such that a front wall 183 is separated from a back wall 184 by a dimension JJ which extends from a mid-point on an inner surface of the front wall 183, straight back and generally parallel to the longitudinal axis Y, to the post 186. A front wall 183 may also be separated from a back wall 184 by a dimension KK which extends from the outer edge of the front wall 183 to the outer edge of the back wall 184. Also, a first or right post 186 may be separated from a second or left post 186 by a dimension LL running generally parallel to a lateral axis X. Further, a semicircular trough 185 may have a dimension MM running generally parallel to dimension LL. In one embodiment, dimension JJ is greater than dimension KK. In one embodiment, dimension LL is greater than dimension MM. In another embodiment dimension JJ may measure about 0.33 to 0.37 inches, preferably 0.34 to 0.36 inches, or more preferably 0.35 inches in length and dimension KK may measure about 0.31 to 0.35 inches, preferably 0.32 to 0.34 inches, or more preferably 0.33 inches in length. Also, dimension LL may measure about 0.41 to 0.45 inches, preferably 0.42 to 0.44 inches, or more preferably 0.43 inches in length and dimension MM may be about 0.15 to 0.19 inches, preferably 0.16 to 0.18 inches, or more preferably 0.17 inches in length.

In an alternative design, the device may use a generally plane cover and base, with the device not having locating elements 40 and/or spikes 48. In this design, the cover and base act as simple clamping elements to secure the catheter. With sufficient clamping force applied, the cover and base can restrain the catheter against significant movement, without using locating elements, such as walls, posts, etc. Force multiplying elements, such as levers, cams, screw threads, etc. may be used in this type of design to provide adequate clamping force.

The above securing devices may be molded plastic or made of other materials suitable for use with patients. Any of the bases or covers described may be provided in the shapes shown or in other shapes as well, including irregular shapes. Outer walls extending up from a base around the outside of the locating elements may also be provided to help align and engage a cover onto a base. Also, the various embodiments of securing devices described above may be attached to a patient in a variety of ways, e.g., with a pad as shown in FIG. 2, or with other adhesive means.

In other embodiments, a securing device for holding catheters and the like in place advantageously has two parts. A base attached to a pad forms one part. A cover is the other part. The cover may optionally be tethered to the base. The pad preferably has an adhesive back surface for attaching the pad to the patient's skin. The base on the pad has positioning elements such as walls or surfaces adapted to fit securely around a catheter fitting. The catheter fitting may be placed into or onto the base from above. The positioning elements prevent any substantial movement of the catheter fitting, in two dimensions, relative to the base or pad, e.g. in the front/back and left/right side directions. The cover is attached to the base over the catheter fitting. One or both of the base and cover have latching elements for holding the cover onto the base. The cover prevents movement of the catheter fitting in a third dimension, i.e., vertically up and out of the base. Consequently, after the cover is attached to the base over the catheter fitting, the catheter fitting and the catheter are securely held in place on the patient. The catheter may be released and removed from the base by temporarily disengaging the latching elements. The latching elements may be disengaged by, for example, squeezing the sides of the cover. The catheter can therefore be quickly and easily attached to or removed from the patient. Such devices may be used with, e.g., PICC lines, IV catheters, Foley catheters, heart catheters, J-loops, and various other catheters, as well as tubes, cables, lines, and other medical devices.

Figure 31:
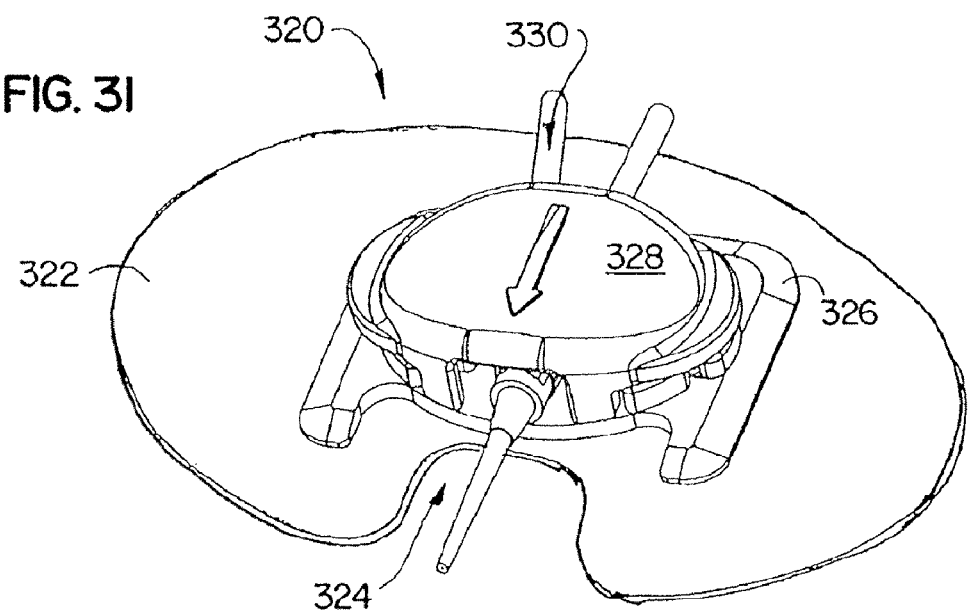
FIG. 31 is a top and front perspective view of another embodiment of a securing device. The pad shown in FIG. 31 is used on each of the various securing devices described below. However, the pad as shown in FIG. 31 is omitted from the remaining drawings, to allow for better illustration of the other components.

For example, FIG. 31 shows an embodiment of a securing device 320 having a base 326 attached to a pad 322. The pad 322 is flexible to conform to the patient's arm or other site. The back side of the pad 322 preferably has one or more peelable strips over an adhesive layer or surface. The specific pad shape and size is not essential and various alternatives may be used. In the example shown in FIG. 31, the pad 322 generally is oval or round, and with a major diameter of from about 1-6, 2-5 or 3-4 inches. The pad does not need any suture holes.

As shown in FIGS. 31-34, a base is attached onto the top side of the pad 322 at a generally central location. The base 326 has positioning walls 350 shaped and dimensioned to fit securely around a fitting 332 on a catheter 330. For the catheter 330 shown in FIGS. 32 and 33, four separate positioning walls 350 are used. In this case, the catheter walls 350 are adapted to fit around the curved ends of the fitting plate. The walls 350 are spaced apart in the back to front direction (indicated by the arrow 356 in FIG. 32) by a dimension just nominally greater than the width of the fitting plate 334. Similarly, the walls 350 are spaced apart side to side by a dimension nominally greater than the length of the fitting plate.

Figure 32:
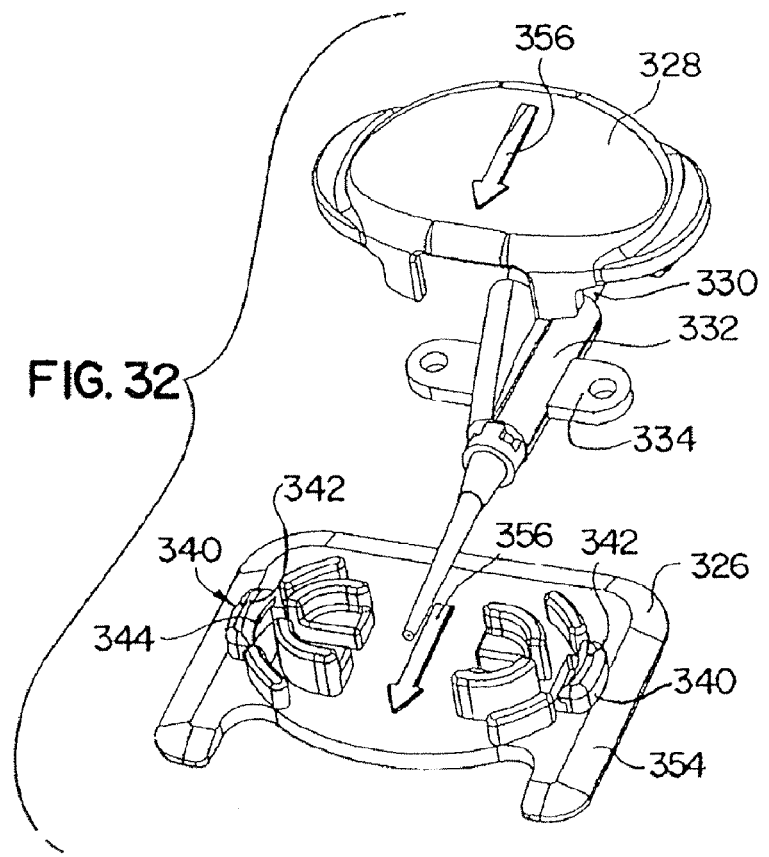
FIG. 32 is an exploded perspective view of the device shown in FIG. 31.
Figure 33:
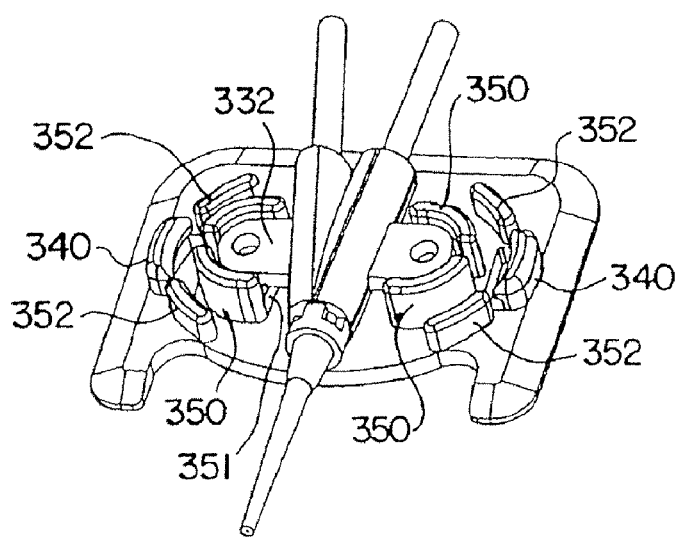
FIG. 33 is a top perspective view of the device shown in FIG. 31, with the cover removed.
Figure 34:
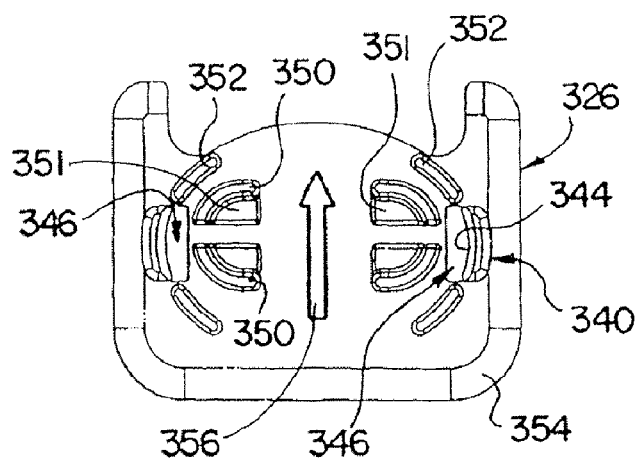
FIG. 34 is a plan view of the base shown in FIGS. 32 and 33.

Referring to FIGS. 32-34, outer walls 352 extend up from the base 326 around the outside of the positioning walls 350. The outer walls are lower than the positioning walls. Latching arms 340 extend up generally from opposite sides of the base 326. An angled face or surface 344 is provided at the top or head 342 of each of the arms 340. The base 326 may have a tapered or inclined edge or rim 354. One or more through holes 346 may be provided in the base 326, if desired, for manufacturing purposes. An arrow symbol 356 may be provided on the base 326 and/or the cover 328, to indicate how the catheter 330 should be installed into the device 320.

Figure 35:
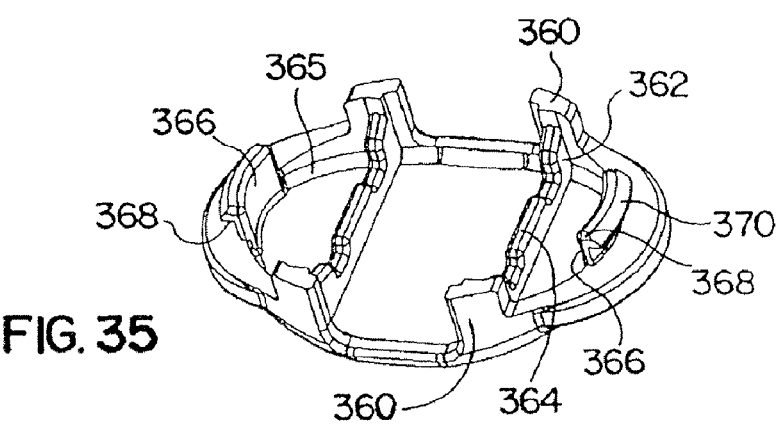
FIG. 35 is a perspective view of the under side of the cover shown in FIGS. 31 and 32.

As shown in FIGS. 32 and 35, the cover 328 has latching arms 366, with an angled surface or face 370 at the outer or lower end 368 of each arm 366, similar to the latching arms 340 on the base 326. In the oblong cover 328 shown in FIG. 35, the arms 366 are centered at opposite sides of the cover, along the major axis of the cover. Web sections 362 run between column legs 360 on the bottom or under side of the cover 328. The column legs extend out beyond the latching arms 366. A contact or land surface or area 364 on the web sections 362 are adapted to lightly contact the top of the catheter fitting 332 when the cover 328 is attached to the base 326.

In use, after the catheter has been placed, the skin at the securement site is preferably cleaned. The catheter fitting 332 is then placed into or onto the base 326, as shown in FIG. 33. Land or boss areas 351 may be provided on the floor of the base 326, within the positioning walls 350, as shown in FIGS. 33 and 33. These areas 351 may be used, if desired, to support the catheter fitting 332 off of the floor of the base 326. The cover 328 is then attached to the base 326 over the fitting 332, as shown in FIG. 31. The outer walls 352 may align with and engage against inner rim surfaces 365 on the cover 328, as shown in FIG. 35. This interaction, if used, helps to align the cover onto the base, and to securely attach the cover to the base. The column legs rest on flat outer areas of the base.

The column legs 360 are dimensioned so that when they bottom out on the base 326, the contact surfaces 364 rest on the catheter fitting 332. The legs 360 prevent crushing or deformation of the catheter fitting, by keeping the contact surfaces 364 at a specified dimension above the base floor. As a result, the catheter fitting cannot be crushed, even if the cover is forcefully clamped down onto the base. The fitting 332 is securely held in place (horizontally) on the base between the positioning walls and is held in place vertically between the floor of the base 326 and the contact surfaces 364 of the cover.

As the cover is moved down onto the base 326, the angled surfaces 344 on the base latching arms 340 engage the angled surfaces 370 on the cover latching arms 366. This provides for a cover self aligning operation. The arms 340 and 366 are somewhat resilient and can flex slightly under load in the lateral direction. As a result, as the cover is moved into engagement with the base, the base latching arms 340 flex slightly outwardly, and the cover latching arms flex slightly inwardly. The surfaces 344 and 370 of the arms 340 and 366 slide against and then pass by each other. The arms 340 and 366 then flex back to near their original lateral positions, locking the cover 328 onto the base 326. The peel strip(s) are removed from the back of the pad 322, and the pad is placed onto the prepared securement site. The device 320 then prevents virtually any movement of the catheter fitting 332, which is joined to or part of the catheter 330. A cut out 324 may be provided at the front of the pad 322 to allow the base 326 to be closer to the incision or catheter entry point.

The catheter 330 may be removed by squeezing the sides of the cover 328 towards each other. The cover 328 is slightly flexible. Squeezing causes the cover to curve or bow up. As the cover curves, the arms 366 are drawn inwardly enough to pull the ends 368 of the arms 366 on the cover 328 away from the ends 342 of the arms 340 on the base 326. The head or ends 342 and 368 can then pass by each other as the cover is lifted off of the base.

Figure 36:
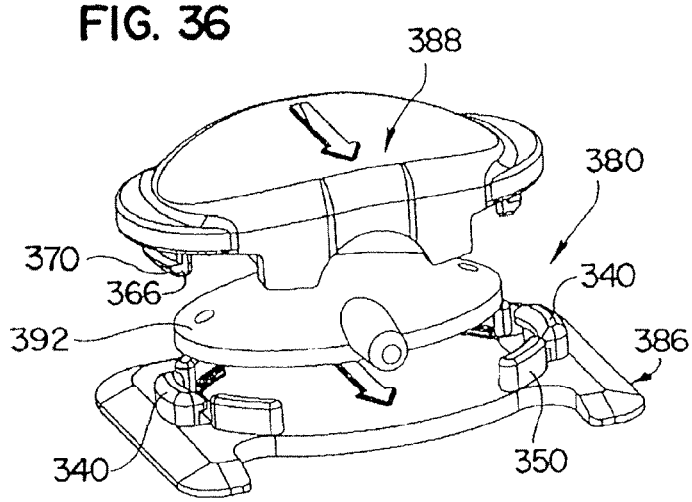
FIG. 36 is an exploded top and front perspective view of another securing device design useable with another type of catheter.
Figure 37:
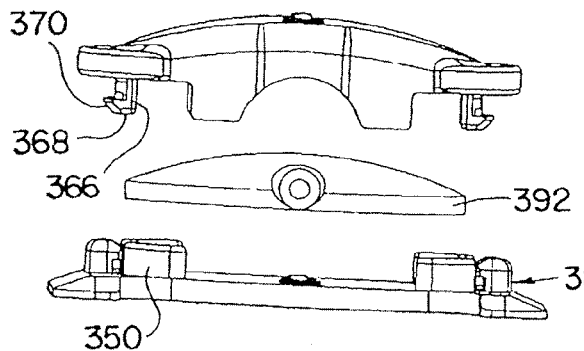
FIG. 37 is a front view of the device shown in FIG. 36.
Figure 38:
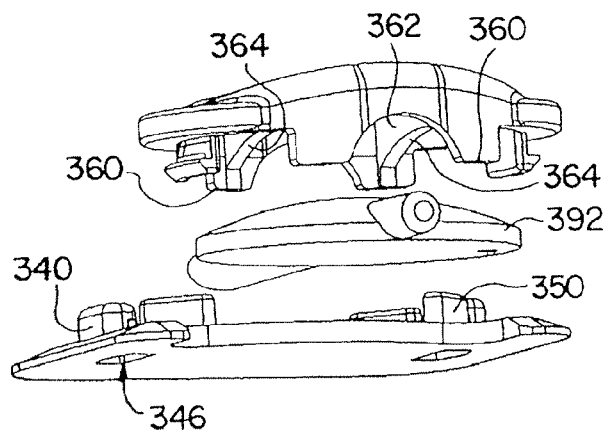
FIG. 38 is a front and bottom perspective view of the device shown in FIGS. 36 and 37.
Figure 39:
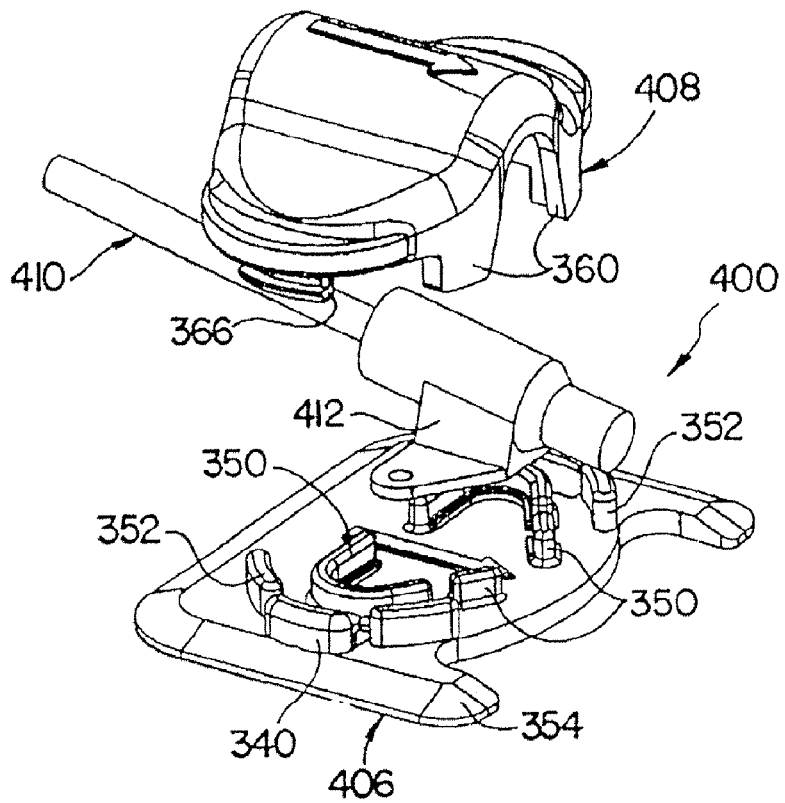
FIG. 39 is a top and side exploded perspective view of another securing device design useable with another type of catheter.

FIGS. 36-38 show another embodiment of a securing device 380 for use with a catheter 390 and catheter fitting 392. The cover 388 has curved contact surfaces 364 matching the top of the fitting 392. The base 386 has positioning walls 350 adapted to fit around the fitting 392.

Figure 40:
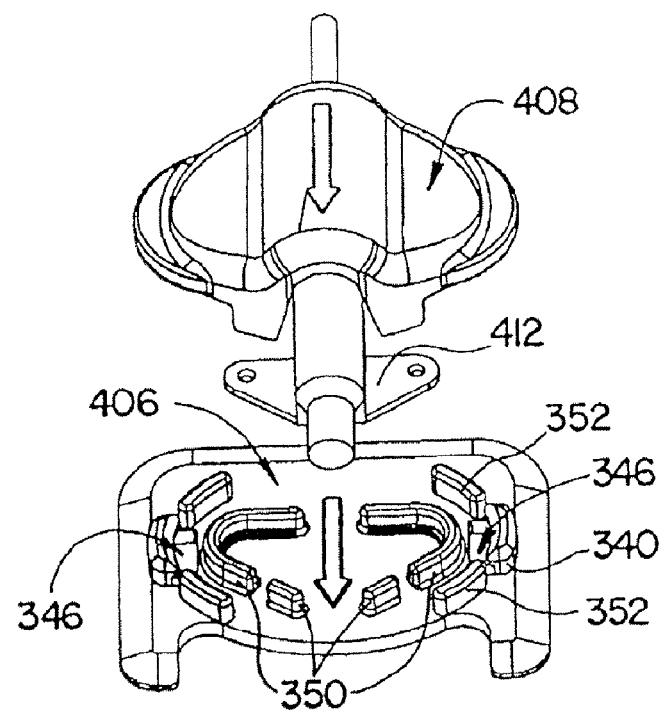
FIG. 40 is a top and front view of the device shown in FIG. 39.
Figure 41:
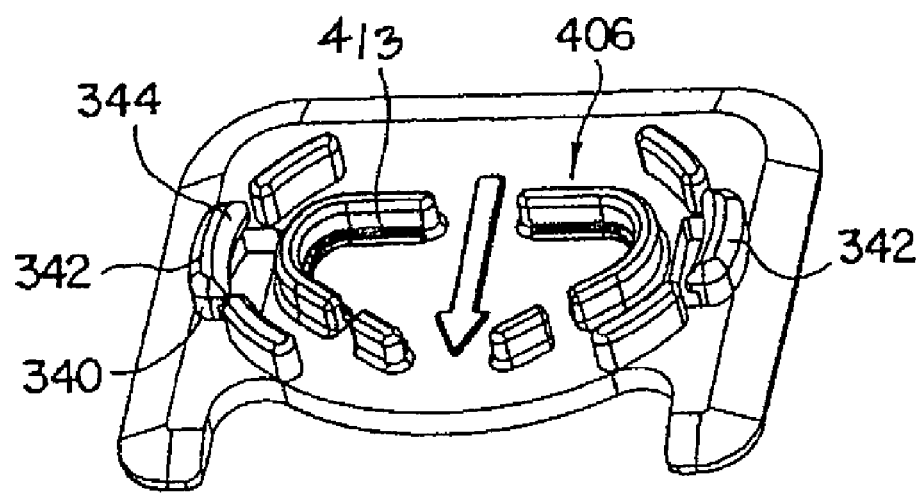
FIG. 41 is a top perspective view of the base shown in FIGS. 39 and 40.
Figure 42:
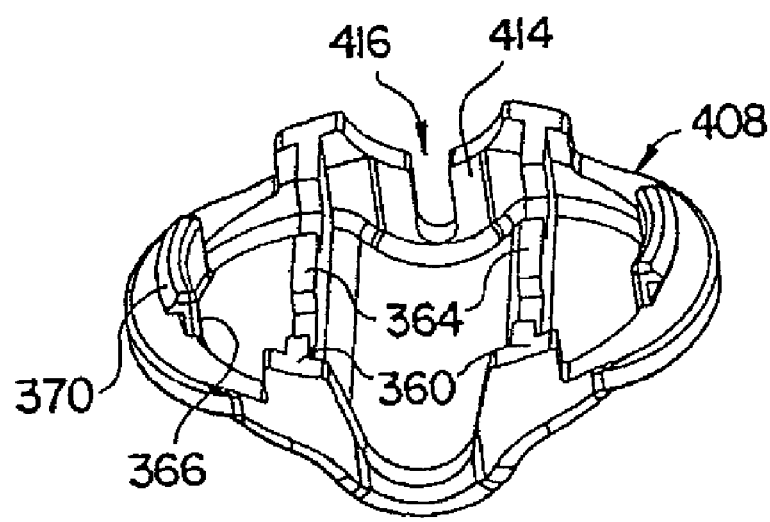
FIG. 42 is perspective view of the under side of the cover shown in FIGS. 39 and 40.

FIGS. 39-42 show another embodiment of a securing device 400 for use with another type of catheter 410 and catheter fitting 412. As shown in FIG. 40, the positioning walls 350 on the base 406 are segmented. The cover 408, as shown in FIG. 42, includes an opening 416 in a rear wall 414.

Figure 43:
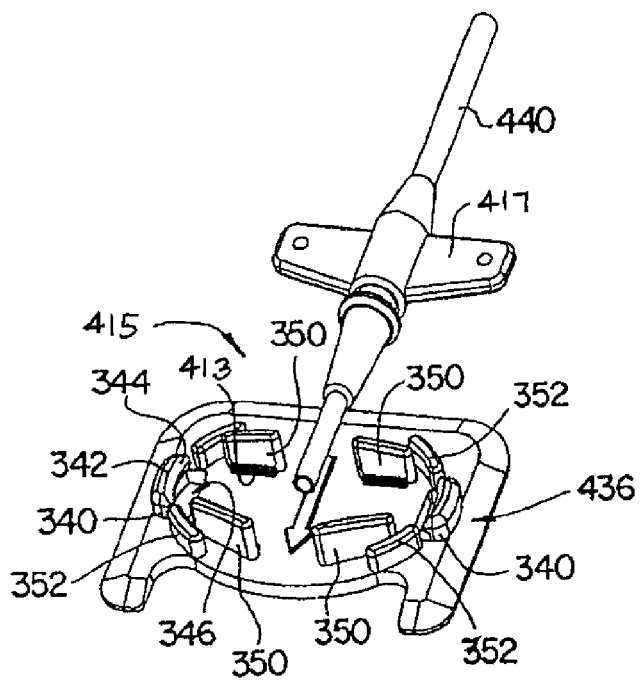
FIG. 43 is a top and side exploded perspective view of another securing device design useable with another type of catheter.
Figure 44:
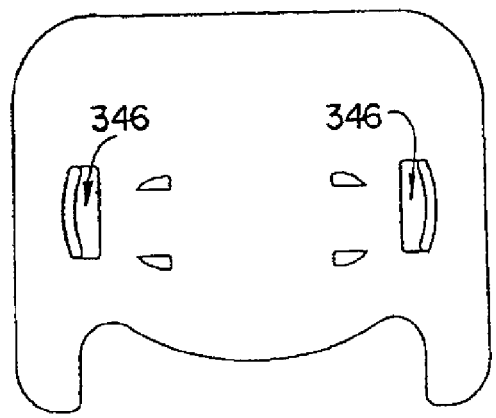
FIG. 44 is a bottom view of the base shown in FIG. 43.
Figure 45:
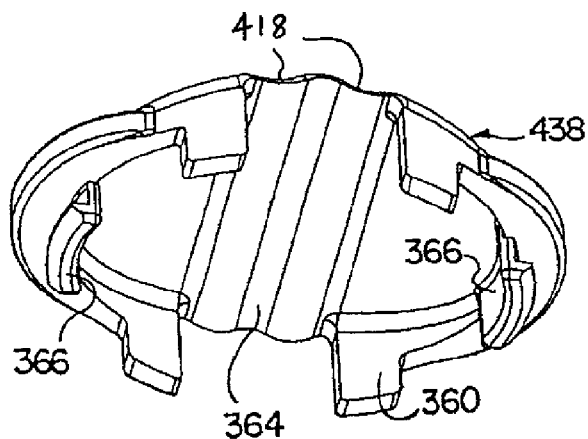
FIG. 45 is perspective view of the under side of the cover used with the base shown in FIG. 43.
Figure 46:
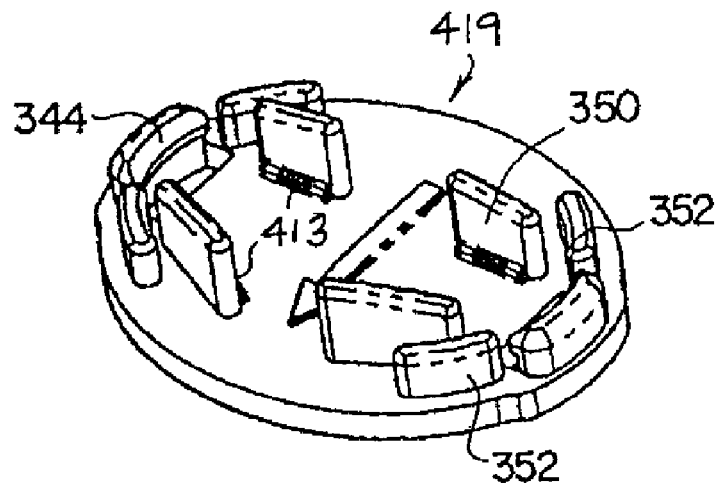
FIG. 46 is a perspective view of an alternative base, similar to the base shown in FIG. 43, and having a generally oval shape.
Figure 47:
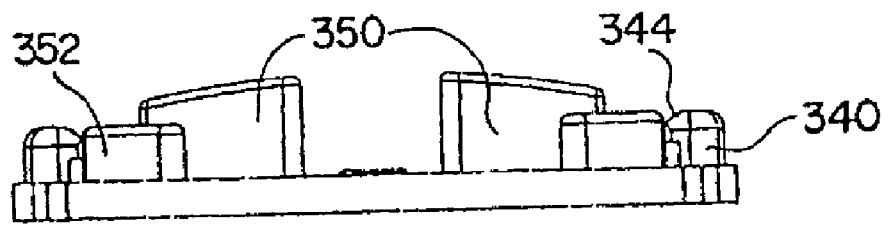
FIG. 47 is a side view of the base shown in FIG. 46.

FIGS. 43-45 show another embodiment of a securing device 415 for use with yet another type of catheter 440 and catheter fitting 417. In this design, four positioning walls 350 are provided on the base 436. Grooves 418 may be provided on the cover 408 to make the cover more flexible. As shown in FIGS. 41, 43 and 46, ramps or ridges 413 may be provided on the base floor near or adjoining one or more of the positioning walls 350. These features may be used to set the orientation of the catheter fitting in the device. FIGS. 46 and 47 show a base 419 similar to the base 436 shown in FIG. 43. The base 419 is generally oval shaped as opposed to the more rectangular base 436 shown in FIG. 43.

The devices shown in FIGS. 36-47 operate in the same way as the device 320 shown in FIGS. 31-35 and described above. The base and cover in each design may be molded plastic. The positioning walls 350 may be segmented, as shown in the drawings, or continuous. Indeed, a single continuous positioning wall surrounding the catheter fitting 417 on all sides may be used. Alternatively, multiple short spaced apart wall segments around two, three or more sides of the fitting may also be used. The wall segments may be various shapes, including generally rectangular, as shown in FIGS. 45-47, as well as round, square, hexagonal, etc. Positioning or locating elements, such as the walls 350, may optionally also be provided on the cover. Moveable or adjustable positioning elements or wall segments may also alternatively be provided on the base. If used, these may have a single direction or ratchet feature, so that they can move only inwardly to contact the sides of the catheter fitting. Moveable positioning elements may allow use of a single device with more than one specific type of catheter.

Any of the above-described embodiments and elements described in the embodiments may be used alone or in combination with one another. For example, a hinge, or tongue and groove or bar connection mechanism for permanently or non-permanently connecting a cover to a base could be used with any of the above described bases. Furthermore, the securing device may include additional features not described herein. While several embodiments have been shown and described, various changes and substitutions may of course be made, without departing from the spirit and scope of the invention.

The invention claimed is:

1. A device for securing a catheter on a patient, comprising:
a base including a receiving area and a plurality of locating elements arranged around the receiving area for positioning a catheter, the base further including an opening in which a retention plate is movably retained;
a cover connected to the base, with the cover including:
at least one contact element on an interior surface of the cover for directly contacting the catheter when the cover is in a closed position; and
at least one opening for receiving a portion of the catheter when the cover is in the closed position; and
at least one latching element for securing the base to the cover in the closed position.

2. The device of claim 1 further comprising a recessed region in the receiving area for receiving the catheter.

3. The device of claim 1, wherein the cover is removably connected to the base.

4. The device of claim 3, wherein the cover includes a tongue and the base includes a bar about which the tongue is pivotable.

5. The device of claim 4 further comprising a restraining arm on the base, wherein the tongue includes a tab for engaging the restraining arm when the cover is in an open position to substantially prevent the cover from separating from the base.

6. The device of claim 1 further comprising a plurality of upwardly extending teeth in the receiving area for engaging the catheter.

7. The device of claim 1 wherein the base includes an angled surface for maintaining the catheter at an intended angle.

8. The device of claim 1 further comprising:
a plurality of restraining elements attached to an upper surface of the base and extending over the opening in the base;
a support plate attached to a bottom surface of the base or press fit into the opening in the base;
wherein the retention plate is movably retained between the support plate and the restraining elements.

9. The device of claim 1, wherein the locating elements and the receiving area are located on the retention plate.

10. The device of claim 9 wherein the locating elements comprise a plurality of upwardly extending walls.

11. A device for securing a catheter on a patient, comprising:
a base including a receiving area;
a fixed restraining wall on the base located on one side of the receiving area;
a movable restraining wall on the base located on a substantially opposing side of the receiving area;
wherein the movable restraining wall is movable between an open position in which a catheter may be received in the receiving area, and a closed position in which the fixed restraining wall and the movable restraining wall secure the catheter between them in the receiving area.

12. The device of claim 11 further comprising a tab located on the base for holding the movable restraining wall in the closed position.

13. The device of claim 11 further comprising at least one receptacle in the receiving area for receiving an extension on the catheter.

14. A device for securing a catheter on a patient, comprising:
a clasp including a first section having a first engagement end and a second section having a second engagement end, with the first section pivotable about a joint relative to the second section between an open position and a closed position, wherein the clasp is configured to fit around a catheter when in the closed position;
a first flange extending from the first section;
a second flange extending from the second section;
wherein the first and second flanges are disposed on opposite sides of the joint at least when in the closed position and are movable toward each other to move the clasp into the open position.

15. The device of claim 14 wherein the first section includes a ridge that is engageable with an opening in the second section to hold the clasp in the closed position.

16. A device for securing a catheter on a patient, comprising:
a base including a receiving area;
a first track positioned on a first side of the receiving area;
a first clamp movable along the first track; and
a second clamp positioned on a second side of the receiving area, with the second clamp engageable with the first clamp to secure a catheter within the receiving area.

17. The device of claim 16 further comprising a second track on the second side of the receiving area, with the second clamp movable along the second track.

18. The device of claim 16 further comprising a plurality of teeth on at least one of the first clamp and the second clamp for engaging the catheter.

19. The device of claim 16 wherein at least the first clamp includes a fixed tab and a push tab that, when moved toward each other, free the first clamp to be movable along the first track.

* * * * *